US010174170B2

(12) United States Patent
Maeshima et al.

(10) Patent No.: US 10,174,170 B2
(45) Date of Patent: Jan. 8, 2019

(54) METHOD FOR PRODUCING LIQUID HIGH-PURITY POLYHYDRIC ALCOHOL DERIVATIVE-MODIFIED SILICONE OR COMPOSITION THEREOF

(71) Applicant: Dow Corning Toray Co., Ltd., Tokyo (JP)

(72) Inventors: Hideko Maeshima, Chiba (JP); Seiki Tamura, Chiba (JP)

(73) Assignee: Dow Corning Toray Co., Ltd., Tokyo (JP)

( * ) Notice: Subject to any disclaimer, the term of this patent is extended or adjusted under 35 U.S.C. 154(b) by 0 days.

(21) Appl. No.: 15/310,255

(22) PCT Filed: Apr. 20, 2015

(86) PCT No.: PCT/JP2015/002154
§ 371 (c)(1),
(2) Date: Dec. 25, 2016

(87) PCT Pub. No.: WO2015/162906
PCT Pub. Date: Oct. 29, 2015

(65) Prior Publication Data
US 2017/0218130 A1    Aug. 3, 2017

(30) Foreign Application Priority Data
Apr. 21, 2014  (JP) .................... 2014-087712

(51) Int. Cl.
C08G 77/34 (2006.01)
A61Q 1/02 (2006.01)
A61Q 19/00 (2006.01)
A61K 8/892 (2006.01)
C08G 77/14 (2006.01)
A61Q 17/04 (2006.01)
B01D 15/00 (2006.01)
B01D 29/01 (2006.01)
B01J 20/14 (2006.01)
C08G 77/38 (2006.01)
A61Q 19/08 (2006.01)
C08G 77/00 (2006.01)

(52) U.S. Cl.
CPC .............. *C08G 77/34* (2013.01); *A61K 8/892* (2013.01); *A61Q 1/02* (2013.01); *A61Q 17/04* (2013.01); *A61Q 19/00* (2013.01); *B01D 15/00* (2013.01); *B01D 29/016* (2013.01); *B01J 20/14* (2013.01); *C08G 77/14* (2013.01); *C08G 77/38* (2013.01); *A61K 2800/10* (2013.01); *A61Q 19/08* (2013.01); *C08G 77/70* (2013.01)

(58) Field of Classification Search
CPC ........ C08G 77/34; C08G 77/38; A61K 8/892; A61Q 1/02; A61Q 17/04; A61Q 19/00; B01D 15/00; B01D 29/016; B01J 20/14

USPC ........................................................ 556/434
See application file for complete search history.

(56) References Cited

U.S. PATENT DOCUMENTS

| | | |
|---|---|---|
| 4,431,789 A | 2/1984 | Okazaki et al. |
| 4,963,093 A | 10/1990 | Dragan |
| 5,144,054 A | 9/1992 | Shioya et al. |
| 5,243,218 A | 9/1993 | Zenitani et al. |
| 5,306,838 A | 4/1994 | Shioya et al. |
| 5,466,849 A | 11/1995 | Shioya et al. |
| 2003/0158363 A1 | 8/2003 | Nakanishi |
| 2004/0146472 A1 | 7/2004 | Nakanishi |
| 2005/0008600 A1 | 1/2005 | Nakanishi et al. |
| 2005/0084467 A1 | 4/2005 | Miyanaga |
| 2008/0210129 A1 | 9/2008 | Nienstedt et al. |
| 2011/0051068 A1 | 3/2011 | Kamon et al. |
| 2012/0269747 A1 | 10/2012 | Iimura et al. |
| 2012/0269748 A1 | 10/2012 | Tamura et al. |
| 2012/0269875 A1 | 10/2012 | Tamura et al. |
| 2012/0328539 A1 | 12/2012 | Tamura et al. |
| 2013/0102686 A1 | 4/2013 | Tamura et al. |
| 2013/0142748 A1 | 6/2013 | Tamura et al. |
| 2013/0177516 A1 | 7/2013 | Tamura et al. |
| 2013/0210930 A1 | 8/2013 | Souda et al. |
| 2013/0221218 A1 | 8/2013 | Lee et al. |

(Continued)

FOREIGN PATENT DOCUMENTS

| | | |
|---|---|---|
| EP | 0523738 A1 | 1/1993 |
| EP | 2940063 A1 | 11/2015 |

(Continued)

OTHER PUBLICATIONS

PCT/JP2015/002154 International Search Report dated Jun. 23, 2015, 2 pages.

(Continued)

*Primary Examiner* — Clinton A Brooks
*Assistant Examiner* — Kofi Adzamli
(74) *Attorney, Agent, or Firm* — Warner Norcross & Judd LLP

(57) ABSTRACT

A production method of a liquid high-purity polyhydric alcohol derivative-modified silicone or a composition thereof is disclosed. The method comprises: a capturing step 1) of bringing into an impurity-containing composition containing a liquid polyhydric alcohol derivative-modified silicone and hydrophilic impurities originating from a polyhydric alcohol derivative, the polyhydric alcohol derivative being a hydrophilic modifier of the polyhydric alcohol derivative-modified silicone, into contact with solid particles capable of capturing the hydrophilic impurities, and then capturing the hydrophilic impurities with the solid particles; and a separating step 2) of separating the polyhydric alcohol derivative-modified silicone and the solid particles. The method is useful for production of the liquid high-purity polyhydric alcohol derivative-modified silicone and the composition thereof on a commercial scale.

14 Claims, No Drawings

(56) References Cited

U.S. PATENT DOCUMENTS

| | | | |
|---|---|---|---|
| 2014/0161758 A1* | 6/2014 | Tamura | C08G 77/46 424/78.02 |
| 2014/0187649 A1 | 7/2014 | Tamura et al. | |
| 2014/0193353 A1 | 7/2014 | Tamura et al. | |
| 2014/0194532 A1 | 7/2014 | Tamura et al. | |
| 2014/0323590 A1 | 10/2014 | Iimura et al. | |
| 2014/0364394 A1 | 12/2014 | Tamura et al. | |
| 2014/0371330 A1 | 12/2014 | Hayashi et al. | |
| 2015/0004107 A1 | 1/2015 | Sawayama et al. | |
| 2015/0011656 A1 | 1/2015 | Tamura et al. | |
| 2015/0080480 A1 | 3/2015 | Tamura et al. | |

FOREIGN PATENT DOCUMENTS

| | | |
|---|---|---|
| JP | S57149290 A | 9/1982 |
| JP | S62195389 A | 8/1987 |
| JP | S63202629 A | 8/1988 |
| JP | H02228958 A | 9/1990 |
| JP | H0689147 A | 1/1992 |
| JP | H04108795 A | 4/1992 |
| JP | H04188795 A | 7/1992 |
| JP | H05156019 A | 6/1993 |
| JP | H05186596 A | 7/1993 |
| JP | H09194594 A | 7/1997 |
| JP | 2002179798 A | 6/2002 |
| JP | 2004339244 A | 12/2004 |
| JP | 2005042097 A | 2/2005 |
| JP | 2005089494 A | 4/2005 |
| JP | 3976226 B2 | 6/2007 |
| JP | 2011126854 A | 6/2011 |
| JP | 2011246704 A | 12/2011 |
| JP | 2011246705 A | 12/2011 |
| JP | 2011246706 A | 12/2011 |
| JP | 201246508 A | 3/2012 |
| JP | 2012046507 A | 3/2012 |
| JP | 2012246445 A | 12/2012 |
| JP | 2012246446 A | 12/2012 |
| JP | 2013010744 A | 1/2013 |
| JP | 2013010934 A | 1/2013 |
| JP | 2013010935 A | 1/2013 |
| JP | 2013151656 A | 8/2013 |
| JP | 2013151657 A | 8/2013 |
| JP | 2013151658 A | 8/2013 |
| JP | 2013151659 A | 8/2013 |
| JP | 2013151660 A | 8/2013 |
| WO | WO02055588 A1 | 7/2002 |
| WO | WO2011049246 A1 | 4/2011 |
| WO | WO2011049247 A1 | 4/2011 |
| WO | WO2011049248 A1 | 4/2011 |

OTHER PUBLICATIONS

English language abstract and machine translation for JPS62195389 (A) extracted from https://www.j-platpat.inpit.go.jp database on Jan. 12, 2017, 7 pages.

English language abstract and machine translation for JPS63202629 (A) extracted from https://www.j-platpat.inpit.go.jp database on Jan. 12, 2017, 8 pages.

English language abstract and machine translation for JPH05156019 (A) extracted from http://worldwide.espacenet.com database on Jan. 3, 2017, 11 pages.

English language abstract and machine translation for JPH05186596 (A) extracted from http://worldwide.espacenet.com database on Jan. 3, 2017, 27 pages.

English language abstract and machine translation for JPH0689147 (A) extracted from http://worldwide.espacenet.com database on Feb. 10, 2017, 12 pages.

English language abstract and machine translation for JP2005089494 (A) extracted from http://worldwide.espacenet.com database on Jan. 11, 2017, 24 pages.

English language abstract and machine translation for JP2012246445 (A) extracted from http://worldwide.espacenet.com database on Dec. 22, 2016, 129 pages.

English language abstract and machine translation for JPH09194594 (A) extracted from http://worldwide.espacenet.com database on Feb. 10, 2017, 25 pages.

\* cited by examiner

METHOD FOR PRODUCING LIQUID HIGH-PURITY POLYHYDRIC ALCOHOL DERIVATIVE-MODIFIED SILICONE OR COMPOSITION THEREOF

CROSS-REFERENCE TO RELATED APPLICATIONS

This application is the National Stage of International Application No. PCT/JP2015/002154 filed on 20 Apr. 2015, which claims priority to and all advantages of Japanese Patent Application No. 2014-087712 filed on 21 Apr. 2014, the content of which is hereby incorporated by reference.

TECHNICAL FIELD

The present invention relates to a production method of a liquid high-purity polyhydric alcohol derivative-modified silicone or a composition thereof. Furthermore, the present invention relates to the use of the liquid high-purity polyhydric alcohol derivative-modified silicone or its composition in external use preparations, cosmetics, and various industrial materials.

BACKGROUND ART

Among the silicones modified by a polyhydric alcohol derivative, it is possible to indicate a glycerin derivative-modified silicone as an example of a typical material other than a sugar derivative-modified silicone.

Commonly known examples of silicones modified by a glycerin derivative include the compounds disclosed in Patent Documents 1 to 9, and the reaction schemes of such compounds are also well known. Generally, since there are almost no cases in which the introduction reaction of a glycerin derivative to a silicone skeleton proceeds by the chemical equivalent (mole equivalent), the introduction reaction is commonly completed by supplying the glycerin derivative in excess. Therefore, in addition to a glycerin derivative-modified silicone copolymer, which is the product, an unreacted modifier (a glycerin derivative) remains as a residual in the reaction system, resulting in turbidity. Since the glycerin derivative has a high boiling point in most cases, and polyglycerin is a high molecular compound, as such, purification by stripping is not effective. Therefore, it was difficult to obtain a high-purity glycerin derivative-modified silicone on a commercial scale. This is due to not only the fact that stripping at an excessively high temperature causes the degeneration of the product or undesirable side reactions, but also the fact that a technique of stripping impurities having a high boiling point at an even higher temperature is inefficient in an actual production process.

Another technique for increasing the purity of an organo-modified silicone containing a residual organic modifier as an impurity is, for example, an extraction (or precipitation/re-precipitation) separation method utilizing the difference in solubility between impurities and the main component. For example, when the organic modifier is a hydrophilic compound, in an extraction separation method, most of the impurities are first extracted and removed with a hydrophilic solvent (alternatively, the main component is conversely extracted with a lipophilic solvent). However, phase separation in the extraction step ordinarily takes time, and this does not yield clean separation. This results in an increase in waste and a decrease in yield and productivity. In addition, in the case of the glycerin derivative-modified silicone, there are many cases in which the entire system enters an emulsified state and cannot be separated, which leads to poor versatility.

On the other hand, a precipitation and re-precipitation method is a technique of dissolving an organo-modified silicone containing a residual organic modifier in an organic solvent with solubility in both, and precipitating and separating the organo-modified silicone by gradually adding water, for example. Patent Document 10 discloses a high-purity polypropylene glycol-modified organosiloxane polymer obtained by a precipitation and re-precipitation method. However, the total amounts of the organic solvent and water that are used in this method are ten times the amount of the organo-modified silicone each time re-precipitation is performed, and this is repeated three times to obtain a high-purity organo-modified silicone with no impurities. Accordingly, taking into consideration problems such as the low productivity in relation to the number of reactions and the large amount of waste water treatment, application to mass production on a commercial scale is difficult. In addition, when the organic modifier is a polyethylene glycol derivative or a glycerin derivative, the hydrophilicity and surface activity of the corresponding organo-modified silicone are increased, so separation and purification are often difficult with this method.

Patent Document 11 discloses an organosiloxane derivative having a sugar residue but not containing an unreacted starting material, which is obtained by a membrane separation method using a dialysis tube. However, a dialysis time of three days is required to obtain 10 g of a high-purity organo-modified silicone, so this method cannot be considered suitable for mass production on a commercial scale from the perspective of efficiency. In addition, in Patent Document 11, it is stated that the purification of the organopolysiloxane derivative is also possible by column chromatography. Patent Document 4 discloses a glyceryl ether-modified silicone purified by a silica gel column. However, column chromatography requires the circulation of a large amount of a solvent in order to obtain a high-purity organo-modified silicone, and there are many problems with production on a commercial scale, such as the apparatus design, the recovery of the waste solvent, the removal of the solvent from the recovered solution, and low productivity.

Patent Document 12 discloses a purification method for an alkyl glyceryl polysiloxane derivative by means of ultrafiltration utilizing a diafiltration method. However, since the pore diameter of ultrafiltration is small and the film tends to become obstructed in a short amount of time, ultrafiltration must be performed after diluting an organo-modified silicone containing an organic modifier around ten times with a volatile solvent such as hexane. Therefore, there are problems such as the removal of the solvent from the filtrate, low productivity, and operator safety.

Patent Document 7 proposes a method for producing a branched polyglycerol-modified silicone obtained by adding/graft polymerizing a silicone having at least one functional group selected from the group consisting of hydroxy groups, carboxy groups, amino groups, imino groups, mercapto groups, and epoxy groups, with 2,3-epoxy-1-propanol in the presence of an acidic or basic catalyst. With this method, however, the siloxane backbone breaks during graft polymerization, and as a result, at least two components having different properties tend to be produced as copolymers, and there are many problems from the perspectives of quality and the purification step, and thus, it is difficult to obtain a high-purity polyglycerin-modified silicone in a stable manner on a commercial scale.

In addition, Patent Document 13 discloses a hydrogenation treatment for the glycerin-modified polysiloxane, and an acid treatment following the hydrogenation treatment, in Example 5, as a purification method of a modified silicone compound having a branched polymer made of a hydrophilic group. However, this technique is a deodorizing technique by which the unsaturated group portion of the residual organic modifier, which is the source of odorization of the modified silicone composition, is stabilized by hydrolysis and the hydrogenation treatment, and a high-purity glycerin-modified silicone is not obtained. In this technique, the excess glycerin derivative changes the structure thereof and continues to remain in the composition.

Recently, Patent Document 8 has proposed a novel alternating copolymer of organopolysiloxane with glycerin derivative, and suggests that a high molecular weight polyglycerin-modified silicone can be obtained without the problem of white turbidness, and the like, caused by the unreacted starting material. However, it is clear from the chemical structure that this compound has a hydrophilic group portion incorporated on its backbone. As a result, this copolymer has properties completely different than those of conventional general-use hydrophilic silicones such as polyether-modified silicone and the like and, therefore, a high level of technical skill is necessary to stably compound this copolymer in delicate formulations such as cosmetic products and the like, leading to the problem of the field of use being limited.

In such a situation, in Patent Document 14, the present inventors disclose a novel organopolysiloxane containing a hydrophilic group, which is easy to produce and incurs almost no phase separation or sedimentation of unreacted starting material and the like after production, and is chemically stable and has excellent practicality, and a method for producing the same. In particular, they propose that this organopolysiloxane be used as a surfactant, powder treatment agent, and surface treatment agent that can be advantageously used in the field of cosmetics. Moreover, in Patent Document 15, the present inventors disclose a novel liquid organopolysiloxane having flowability at least at 100° C., having a silicon-bonded glycerin derivative group, and also having a crosslinked structure including a carbon-silicon bond in the crosslinking part, and a method for producing the same. At the same time, they propose an external use preparation or cosmetics having an excellent emulsion stability without the inclusion of a compound containing a polyoxyethylene structure, which conforms to the worldwide trend of improving the overall configuration of a product for the end consumer, such as cosmetic products, etc. including the liquid organopolysiloxane, to a PEG-FREE formulation. In addition, the present inventors examine the usage, structure, functions, etc. of these novel materials, and disclose the details in Patent Documents 16 to 23.

In Patent Documents 14 to 23, a production example of not only the glycerin derivative-modified silicone invented by the present inventors, but also of the glycerin derivative-modified silicone based on the prior techniques has been reported as a comparison product. However, most of the compositions containing the glycerin derivative-modified silicone at the point of time when the reaction step ended, except for those for which the hydrogenation treatment is performed, have a milky white to grayish brown opaque appearance. Moreover, there are also case examples of attempts made to reduce the residual glycerin derivative, which is the cause of turbidity, by filtering the opaque composition, however, there are cases in which a translucent appearance is obtained, or conversely, there are also cases in which the turbidity is not removed at all, and as such there has been no known technique of increasing the purity of a glycerin derivative-modified silicone composition that is practical and clear, and is effective for a wide range of design structures.

For example, in Examples 2 to 7 of Patent Document 22, it has been reported that the glycerin derivative co-modified organopolysiloxane that has a low viscosity and a low HLB is obtained as a transparent liquid by performing the filtration process after removing the low-boiling components following the hydrosilylation reaction. Since these glycerin derivative-modified silicones have an extremely low HLB and low viscosity, the affinity of the residual glycerin derivative starting material in the reaction mixture and the glycerin derivative-modified silicone, which is the product, is extremely poor, and when allowed to stand for a period of one day up to a few days at laboratory scale, two-layer separation occurs, and the residual starting material undergoes sedimentation. Hence, by sampling and filtering out only the phase of the glycerin derivative-modified silicone, which is a supernatant, excellent transparency can be obtained. Therefore, there were problems that the yield was low and certain amount of time was required for production, as well as that the applicable range of the structure was narrow. In addition, there was the problem that since the bulk (height) of the reaction mixture increases during production of a large amount on a commercial scale, the time taken until two-layer separation increases significantly as compared to the laboratory scale, which makes it difficult to filter only the supernatant liquid.

As described above, until now, there has been almost no known effective method for producing a liquid high-purity glycerin derivative-modified silicone or a composition containing the same in a stable manner on a commercial scale. Further, there has also been no known technique of increasing the purity of a liquid glycerin derivative-modified silicone which can be applied regardless of the type of the glycerin modifier and can reasonably cope with production on a commercial scale. Therefore, there has been a demand for the development of a high-purity glycerin derivative-modified silicone having low turbidity that is stable while being in liquid form, or a composition thereof, which is easy to produce and incurs almost no phase separation or sedimentation of unreacted starting material or the like after production, and a method for producing the same.

CITATION LIST

Patent Literature

Patent Document 1: Japanese Examined Patent Application Publication No. S62-34039A Patent Document 2: Japanese Unexamined Patent Application Publication No. S62-195389A (Japanese Patent No. 2583412B)

Patent Document 3: Japanese Examined Patent Application Publication No. H06-089147

Patent Document 4: Japanese Patent No. 2613124B (Japanese Unexamined Patent Application Publication No. H04-188795A)

Patent Document 5: Japanese Patent No. 2844453B (Japanese Unexamined Patent Application Publication No. H02-228958A)

Patent Document 6: Japanese Patent No. 3976226B (Japanese Unexamined Patent Application Publication No. 2002-179798A)

Patent Document 7: Japanese Patent No. 4485134B (Japanese Unexamined Patent Application Publication No. 2004-339244A)

Patent Document 8: Japanese Patent No. 5037782B (Japanese Unexamined Patent Application Publication No. 2005-042097A)

Patent Document 9: Japanese Patent No. 4357909B (Japanese Unexamined Patent Application Publication No. 2005-089494A)

Patent Document 10: Japanese Unexamined Patent Application Publication No. S63-202629A Patent Document 11: Japanese Patent No. 3172787B (Japanese Unexamined Patent Application Publication No. H05-186596A)

Patent Document 12: Japanese Unexamined Patent Application Publication No. H05-156019A Patent Document 13: WO/2002/055588

Patent Document 14: WO/2011/049248

Patent Document 15: Japanese Unexamined Patent Application Publication No. 2013-151660A Patent Document 16: WO/2011/049247

Patent Document 17: WO/2011/049246

Patent Document 18: Japanese Unexamined Patent Application Publication No. 2011-126854A Patent Document 19: Japanese Unexamined Patent Application Publication No. 2012-046507A Patent Document 20: Japanese Unexamined Patent Application Publication No. 2013-151659A Patent Document 21: Japanese Unexamined Patent Application Publication No. 2013-151658A Patent Document 22: Japanese Unexamined Patent Application Publication No. 2013-151657A Patent Document 23: Japanese Unexamined Patent Application Publication No. 2013-151656A Patent Document 24: Japanese Unexamined Patent Application Publication No. 2011-246704A Patent Document 25: Japanese Unexamined Patent Application Publication No. 2011-246705A Patent Document 26: Japanese Unexamined Patent Application Publication No. 2011-246706A Patent Document 27: Japanese Unexamined Patent Application Publication No. 2012-246445A Patent Document 28: Japanese Unexamined Patent Application Publication No. 2012-246446A Patent Document 29: Japanese Unexamined Patent Application Publication No. 2012-046508A

SUMMARY OF INVENTION

Technical Problem

The present invention has been achieved to solve the above problems, and an object thereof is to provide a production method of a liquid high-purity polyhydric alcohol derivative-modified silicone or a composition thereof useful for production on a commercial scale.

Particularly, the present invention can be applied regardless of the type of the polyhydric alcohol modifier, and an object thereof is to provide a technique of increasing the purity of a liquid polyhydric alcohol derivative-modified silicone which can easily cope with the production on a commercial scale.

Moreover, an object of the present invention is to provide a liquid high-purity polyhydric alcohol derivative-modified silicone or a composition thereof whose appearance is transparent or translucent since a large amount of hydrophilic impurities are removed.

Particularly, an object of the present invention is to provide a high-purity polyhydric alcohol derivative-modified silicone or its composition that has a high transparency, the high transparency being maintained even after the temperature history has elapsed or after storage over a long period of time, and that is in liquid form and almost free from the concern of giving rise to problems of separation and sedimentation, etc.

A further object of the present invention is to use such a liquid high-purity polyhydric alcohol derivative-modified silicone or its composition in an external use preparation, cosmetics, or various industrial materials.

Solution to Problem

The object of the present invention is achieved by a production method of a liquid high-purity polyhydric alcohol derivative-modified silicone or a composition thereof, the method comprising: a capturing step of bringing an impurity-containing composition containing a liquid polyhydric alcohol derivative-modified silicone and hydrophilic impurities originating from a polyhydric alcohol derivative, the polyhydric alcohol derivative being a hydrophilic modifier of the polyhydric alcohol derivative-modified silicone, into contact with solid particles capable of capturing the hydrophilic impurities, and then capturing the hydrophilic impurities with the solid particles; and a separating step of separating the polyhydric alcohol derivative-modified silicone and the solid particles.

The polyhydric alcohol derivative-modified silicone is preferably a polyhydric alcohol derivative-modified silicone other than a sugar derivative-modified silicone.

The solid particles preferably include at least one substance selected from a low molecular organic compound not containing a silicon atom, an uncrosslinked hydrophilic high molecular organic compound not containing a silicon atom, a crosslinked hydrophilic high molecular organic compound not containing a silicon atom, salts, materials derived from minerals, and activated carbon.

The solid particles preferably include a crosslinked hydrophilic high molecular organic compound not containing a silicon atom. It is particularly preferable that the crosslinked hydrophilic high molecular organic compound is at least one selected from a crosslinked polyacrylate such as a carboxyvinyl polymer (Carbomer) or its salts or partially neutralized substances, an alkyl-modified crosslinked polyacrylate such as an alkyl-modified carboxyvinyl polymer (acrylate/C10-30 alkyl acrylate crosspolymer) or its salts or partially neutralized substances, a crosslinked polyacrylamide, a crosslinked poly (2-acrylamide-2-methylpropanesulfonic acid) polymer, and the like.

The solid particles are preferably porous.

The solid particles preferably include silicon dioxide.

The solid particles preferably include at least one hydrogen bond-forming substance and/or at least one ionic bond-forming substance and/or a hydrate thereof.

The separating step preferably includes a filtering step using a filtering material (filter).

The impurity-containing composition is preferably brought into contact with the solid particles in the capturing step after diluting with a solvent, the solvent being a good solvent of the polyhydric alcohol derivative-modified silicone and a poor solvent of the hydrophilic impurities. In such a case, the production method of the present invention preferably comprises a step of removing the solvent by heating and/or decompressing the composition after the separating step.

The polyhydric alcohol derivative-modified silicone is preferably a polyhydric alcohol derivative-modified silicone represented by the following general formula (1):

[Chemical Formula 1]

(in the formula (1), $R^1$ represents a monovalent organic group (however, excluding $R^2$, L, and Q), a hydrogen atom or a hydroxyl group; $R^2$ represents a substituted or unsubstituted, straight or branched monovalent hydrocarbon group having from 9 to 60 carbons, or a chain organosiloxane group represented by the following general formula (2-1):

[Chemical Formula 2]

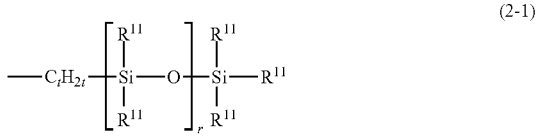

(in the formula (2-1), $R^{11}$ are each independently a substituted or unsubstituted monovalent hydrocarbon group having from 1 to 30 carbons, hydroxyl groups, or hydrogen atoms and at least one of the $R^{11}$ moieties is the monovalent hydrocarbon group; t is a number in a range of 2 to 10; and r is a number in a range of 1 to 500), or the following general formula (2-2):

[Chemical Formula 3]

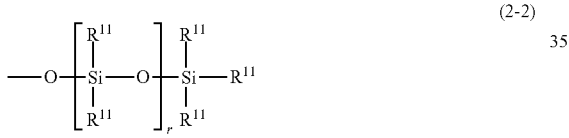

(in the formula (2-2), $R^{11}$ and r are synonymous with those described above); $L^1$ represents a silylalkyl group having a siloxane dendron structure represented by the following general formula (3) when i=1:

[Chemical Formula 4]

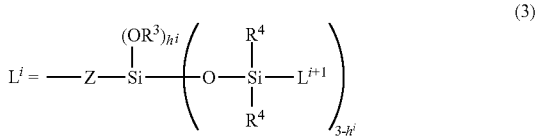

(in the formula (3), $R^3$ each independently represent a substituted or unsubstituted, straight or branched monovalent hydrocarbon group having from 1 to 30 carbons; $R^4$ moieties each independently represent an alkyl group or phenyl group having from 1 to 6 carbons; Z represents a divalent organic group; i represents a generation of the silylalkyl group represented by $L^i$ and is an integer of 1 to k when k is the number of generations that is a number of repetitions of the silylalkyl group; the number of generations k is an integer of 1 to 10; $L^{i+1}$ is the silylalkyl group when i is less than k, and $R^4$ when i=k; and $h^i$ is a number in a range of 0 to 3); Q represents a polyhydric alcohol derivative group; and a, b, c, and d are numbers in the ranges of $1.0 \leq a \leq 2.5$, $0 \leq b \leq 1.5$, $0 \leq c \leq 1.5$, and $0.0001 \leq d \leq 1.5$, respectively).

The polyhydric alcohol derivative group is preferably a glycerin derivative group.

The polyhydric alcohol derivative group is preferably bonded to a silicon atom via a divalent linking group and is preferably a glycerin derivative group comprising at least one unit having an average number of repetitions in a range of 1 to 10, the unit being selected from hydrophilic units represented by the following structural formulae (4-1) to (4-3):

[Chemical Formula 5]

(wherein, W represents a hydrogen atom or an alkyl group having from 1 to 20 carbons)

[Chemical Formula 6]

(wherein, W represents a group synonymous with the group described above)

[Chemical Formula 7]

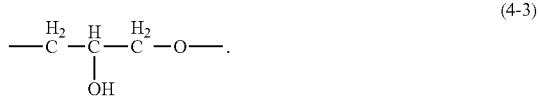

The polyhydric alcohol derivative group preferably does not have an oxyalkylene structure having an average value of the number of repetitions of oxyalkylene units of at least two as a hydrophilic group, and have only a glycerin derivative group having an average value of the number of repetitions of glycerin units in a range of 1 to 5, and does not have other hydrophilic groups.

The polyhydric alcohol derivative group is preferably a diglycerin derivative group represented by the following general formula (5-1):

[Chemical Formula 8]

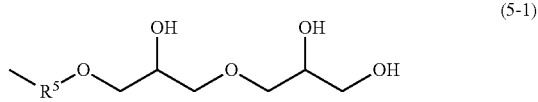

(wherein, $R^5$ represents a divalent organic group not having an oxyalkylene structure with an average value of a number of repetitions of oxyalkylene unit of at least 2) or general formula (5-2):

[Chemical Formula 9]

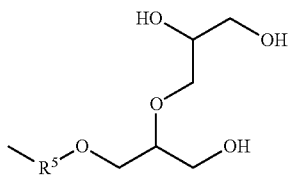

(5-2)

(wherein, $R^5$ is synonymous with that described above).

The polyhydric alcohol derivative-modified silicone may be a polyhydric alcohol derivative-modified crosslinked silicone.

The present invention also relates to a transparent or translucent liquid high-purity polyhydric alcohol derivative-modified silicone or a composition thereof obtained by the production method of the present invention.

The objects of the present invention are also achieved by an external use preparation, a cosmetic, or an industrial material containing a transparent or translucent liquid high-purity polyhydric alcohol derivative-modified silicone or its composition obtained by the production method of the present invention.

Advantageous Effects of Invention

The production method of the present invention is useful in the production of a liquid high-purity polyhydric alcohol derivative-modified silicone or a composition containing the same on a commercial scale.

Particularly, the present invention can be applied regardless of the type of the polyhydric alcohol modifier, and can easily cope with the production of a liquid high-purity polyhydric alcohol derivative-modified silicone or a composition containing the same on a commercial scale.

For example, the present invention enables the production of a liquid high-purity polyhydric alcohol derivative-modified silicone or a composition containing the same in a stable manner on a commercial scale even when the boiling point of the polyhydric alcohol derivative modifier (for example, a glycerin derivative) is high, making it difficult to be purified by distillation, or when the polyhydric alcohol derivative modifier (for example, a glycerin derivative) is a high-molecular compound.

When the composition contains a solvent of the polyhydric alcohol derivative-modified silicone, a solution of a high-purity polyhydric alcohol derivative-modified silicone can be produced easily, and the production of this solution has excellent yield and productivity, so the method is also suitable for production on a commercial scale.

Moreover, it is possible for the production method of the present invention to provide a liquid high-purity polyhydric alcohol derivative-modified silicone or a composition containing the same whose appearance is suitably transparent or translucent since a large amount of hydrophilic impurities are removed.

Also, since the impurities, particularly, the impurities originating from the hydrophilic polyhydric alcohol derivative modifier have been removed from the high-purity polyhydric alcohol derivative-modified silicone or a composition containing the same obtained by the production method of the present invention, phase separation, precipitation of the unreacted starting material, and the like are not likely to occur after production. Therefore, the composition is chemically and physically stable.

Therefore, it is possible for the production method of the present invention to provide a high-purity polyhydric alcohol derivative-modified silicone or a composition containing the same that has a high transparency, the transparency being maintained even after the temperature history has elapsed or after storage over a long period of time, and that is in liquid form and does not tend to give rise to separation and sedimentation, and the like.

In addition, the high-purity polyhydric alcohol derivative-modified silicone produced by the present invention or a solvent containing the same can be suitably used in external use preparations or cosmetics and can further be used widely in various industrial materials.

DESCRIPTION OF EMBODIMENTS

The first aspect of the present invention is a production method of a liquid high-purity polyhydric alcohol derivative-modified silicone or a composition thereof, the method comprising:

a capturing step of bringing an impurity-containing composition containing a liquid polyhydric alcohol derivative-modified silicone and hydrophilic impurities originating from a polyhydric alcohol derivative, the polyhydric alcohol derivative being a hydrophilic modifier of the polyhydric alcohol derivative-modified silicone, into contact with solid particles capable of capturing the hydrophilic impurities, and then capturing the hydrophilic impurities with the solid particles; and a separating step of separating the polyhydric alcohol derivative-modified silicone and the solid particles.

In the present invention, the polyhydric alcohol derivative-modified silicone is preferably a polyhydric alcohol derivative-modified silicone other than a sugar derivative-modified silicone, and more preferably, a glycerin derivative-modified silicone.

According to the first aspect of the present invention, when producing a liquid high-purity polyhydric alcohol derivative-modified silicone or a composition thereof, a mixture containing a liquid polyhydric alcohol derivative-modified silicone and hydrophilic impurities is brought into contact with solid particles capable of capturing the hydrophilic impurities, and then selectively capturing the hydrophilic impurities with the solid particles to separate the liquid polyhydric alcohol derivative-modified silicone and the hydrophilic impurities. The solid particles may be of one solid particle, or at least two solid particles may be combined and used.

The above-described "solid" means that the particle is in the solid state in an environment when brought into contact with the impurities, and is in the solid state preferably in the range of 20 to 100° C., more preferably in the range of 20 to 80° C., and even more preferably in the range of room temperature (25° C.) to 60° C.

The form of the above-described "contact" is not limited, and the mixture can be brought into contact with the solid particles in any form, for example, the form may be such that the mixture passes through a layer of the solid particles, or the form may be such that the mixture and the solid particles are mixed and stirred.

The principle of the first aspect of the present invention is that hydrophilic impurities contained in a mixture containing a liquid polyhydric alcohol derivative-modified silicone and the hydrophilic impurities are processed by solid particles capable of capturing the hydrophilic impurities, and thus, the hydrophilic impurities, which are the cause of turbidity of the mixture, are captured effectively with the solid particles, incorporated into the group of solid particles, or absorbed or retained in the group of solid particles, then solidified so as to enable solid-liquid separation from a main component (high-purity polyhydric alcohol derivative-modified silicone) that is a liquid. That is, the solid particles selectively gel or solidify the hydrophilic impurities. The solidified hydrophilic impurities can be separated from the liquid polyhydric alcohol derivative-modified silicone by the normal solid-liquid separation. Therefore, the high-purity liquid polyhydric alcohol derivative-modified silicone can be obtained easily.

The above-described "capturing" means that the hydrophilic impurities bond with the solid particles in any form, which includes, for example, adherence of the hydrophilic impurities with the surface of the solid particles, absorption of the hydrophilic impurities inside the solid particles, and incorporation into a network formed by the group of solid particles. The bond may refer to either a physical or chemical bond. For example, the hydrophilic impurities may physically bond with the solid particles by an intermolecular force such as Van der Waals force, or may chemically bond with the solid particles by an electrostatic interaction such as an ionic bond or covalent bonding, or may bond with the solid particles by the intermolecular force on the basis of polarization, such as hydrogen bonding. That is, the solid particles can have an interaction with the impurities. It is noted that when the hydrophilic impurities are dissolved in the liquid or mixture, the hydrophilic impurities themselves are preferably solidified and integrated with the solid particles through gelling and the like, by being incorporated into the network formed by the group of the solid particles.

For example, by adding hydrophilic or ionic crystal particles as the solid particles in a mixture containing a polyhydric alcohol derivative-modified silicone and hydrophilic impurities, the hydrophilic impurities get coagulated with the hydrophilic or ionic crystal particles as the core and the crystal particles grow massively, as a result, the hydrophilic impurities are solidified and can be easily separated from the polyhydric alcohol derivative-modified silicone.

Moreover, by adding crosslinked hydrophilic high-molecular solid particles as the solid particles in a mixture containing a polyhydric alcohol derivative-modified silicone and hydrophilic impurities, the impurities are absorbed and retained either in the high-molecular three-dimensional network structure or a network formed by a group of the solid particles, as a result, the hydrophilic impurities are solidified as a solid or gel, and can be easily separated from the polyhydric alcohol derivative-modified silicone.

Moreover, by adding uncrosslinked hydrophilic high-molecular solid particles as the solid particles in a mixture containing a polyhydric alcohol derivative-modified silicone and hydrophilic impurities, for example, the impurities either dissolve into the high-molecular structure, are absorbed and retained, or the impurities are trapped in a coagulated network by a high-molecular intermolecular interaction, as a result, the hydrophilic impurities are solidified and can be easily separated from the polyhydric alcohol derivative-modified silicone.

In addition, by adding porous solid particles as the solid particles in a mixture containing a polyhydric alcohol derivative-modified silicone and hydrophilic impurities, the hydrophilic impurities are incorporated and retained either in the fine pores or the gaps between particles due to the capillary phenomenon and the like, as a result, the hydrophilic impurities are solidified and are easily separated from the polyhydric alcohol derivative-modified silicone liquid.

While the solid particles is capable of capturing the hydrophilic impurities, they do not capture the liquid polyhydric alcohol derivative-modified silicone. Therefore, since only the hydrophilic impurities are captured with the solid particles by bringing the mixture into contact with the solid particles, the hydrophilic impurities can be separated from the liquid polyhydric alcohol derivative-modified silicone.

The constituent material of the solid particles is not particularly limited as long as it is capable of capturing the hydrophilic impurities, and can be configured from various inorganic substances, organic substances, or a mixture thereof. The solid particles may be a surface-treated one or a surface-untreated one, but when surface processing is performed, a hydrophilization treatment is preferred. The constituent material of the solid particles preferably has a chemical structure and/or a physical form by which the constituent material can bond with the hydrophilic impurities via the intermolecular force, electrostatic interaction, or covalent bonding. A hydrophilic high-molecular organic compound is particularly preferable as a constituent material of the solid particles, and from the viewpoint of the magnitude of the effect of increasing the purity, a crosslinked hydrophilic high-molecular organic compound is most preferable. While the hydrophilic high-molecular organic compounds may contain a silicon atom, it is preferable that a silicon atom is not contained in the structure. Moreover, the shape of the solid particles is not limited, and the particles may have a spheroidal shape, cubical shape, rod shape, needle shape, plate shape, pillar shape, flake shape, granular form, porous form, irregular shape, spindle shape, cocoon shape, fibrous form, lump form, dendritic shape, spongiform, angular shape, bow shape, round shape, or the solid particles may be coagulated in clusters and the like. The inorganic substances include inorganic elements such as carbon, silicon, and the like as well as metal oxides such as silicon dioxide, titanium oxide, zirconium oxide, magnesium oxide, calcium oxide, zinc oxide, and alumina, and the like. The inorganic substance is preferably a metal oxide, and more preferably silicon dioxide.

The solid particles preferably include at least one substance selected from a low molecular organic compound not containing a silicon atom, an uncrosslinked hydrophilic high molecular organic compound not containing a silicon atom, a crosslinked hydrophilic high molecular organic compound not containing a silicon atom, salts, materials derived from minerals, and activated carbon. The low molecular organic compound not containing a silicon atom includes, for example, organic acids such as divalent or higher carboxylic acid and hydroxy acid, monosaccharides, disaccharides, oligosaccharides, polyphenols having a low molecular weight, flavonoids having a phenolic hydroxyl group, gallic acid and its esters, nucleic acid bases, and their derivatives, and the like. The uncrosslinked hydrophilic high molecular compound not containing a silicon atom may have a chain structure or a branched-chain structure, and includes, for example, water-soluble organic polymers, such as polysaccharides, polyvinyl alcohol, polyethylene oxide, polyethylene glycol, polyacrylic acid, polyacrylamide, and their derivatives thereof. The crosslinked hydrophilic high molecular compound not containing a silicon atom includes, but is not limited to, for example, a crosslinked polyacrylate such as a carboxyvinyl polymer (Carbomer) or its salts or partially neutralized substances, an alkyl-modified crosslinked polyacrylate such as an alkyl-modified carboxyvinyl polymer (acrylate/C10-30 alkyl acrylate crosspolymer) or its salts or partially neutralized substances, a crosslinked polyacrylamide, a crosslinked poly (2-acrylamide-2-methylpropanesulfonic acid) polymer, and the like. The salts include inorganic salts such as sulfates, etc., organic salts such as carboxylic acid salt, various amine salts, and the like. Materials derived from minerals include, for example, a layered clay mineral, diatomaceous earth, pearlite, and the like. Particularly, a crosslinked hydrophilic organic polymer, such as a carboxyvinyl polymer (Carbomer) is preferable. The solid particles are preferably particulate at room temperature.

Solid particles containing a low-molecular organic compound can favorably capture impurities having a low molecular weight, and solid particles containing a high-molecular organic compound can favorably capture impurities having a high molecular weight. Solid particles containing a high-molecular organic compound can also favorably capture impurities having a low molecular weight, but it is difficult for solid particles containing a low-molecular organic compound to capture impurities having a high molecular weight.

The solid particles are preferably porous. The porous inorganic substances include, for example, activated carbon, zeolite, diatomaceous earth, perlite, and the like. The porous organic substances include, for example, starch-acrylic acid graft-based, polyacrylic acid salt-based, polyvinyl alcohol-based, acetic acid vinyl-acrylic acid salt-based, and isobutylene-maleic acid-based, and poly N-vinyl acetamide-based porous bodies of water-absorbing resins. The solid particles preferably include porous inorganic substances, and particularly, diatomaceous earth is preferred. The solid particles preferably include porous organic substances, and particularly, a polyacrylic acid salt-based highly water-absorbing resin is preferred.

The solid particles preferably include at least one hydrogen bond-forming substance and/or at least one ionic bond-forming substance and/or a hydrate thereof. Most of the hydrophilic impurities are hydrophilic, therefore having a hydrogen bond-forming property and/or an ionic bond-forming property, and thus, when the solid particles contain a hydrogen bond-forming substance and/or an ionic-bond-forming substance, the hydrophilic impurities can be captured effectively through hydrogen bonding and/or ionic bonding. Moreover, hydrates can interact with hydrophilic impurities, and particularly, capture the moisture in the mixture or environment, and the moisture can bond with the hydrophilic impurities by mediating the hydrogen bond. However, from the viewpoint of affinity with the hydrophilic impurities, the solid particles preferably include at least one hydrogen bond-forming substance and/or at least one ionic bond-forming substance. Moreover, the hydrogen bond-forming substance or the ionic bond-forming substance may have a form of a hydrate having at least one hydration water molecule in the composition formula.

The hydrogen bond-forming substance is not particularly limited as long as it is a solid that can form a hydrogen bond, and includes hydrophilic low molecular organic compounds not containing a silicon atom, uncrosslinked hydrophilic high molecular organic compounds not containing a silicon atom, crosslinked hydrophilic high molecular organic compounds not containing a silicon atom, and the like. Particularly, a hydrophilic hydrogen bond-forming substance is preferred, and a hydrogen bond-forming substance that can form at least two hydrogen bonds between molecules is preferable.

The hydrogen bond-forming substance preferably has a functional group that enables hydrogen bonding, such as a hydroxyl group, carboxyl group, aldehyde group, carbonyl group, amino group, amide group, ether group, and the like. The hydrogen bond-forming substance can be selected from, for example, sugars, sugar alcohols, polysaccharides, hydroxyl group-containing polymers, phenols, aldehydes, ketones, carboxylic acids, esters, ethers, amino acid, amines, amides, or their salts or mixtures. The hydrogen bond-forming substance is preferably a solid particulate at room temperature (25° C.) to 60° C.

Sugars include, for example, monosaccharides such as glucose, fructose, galactose, mannose, talose, sorbose, xylose, lyxose, fucose, arabinose, rhamnose, ribose, ribulose, xylulose, or sorbitol; disaccharides such as maltose, lactose, cellobiose, trehalose, sucrose, and the like; trisaccharides such as maltotriose; and galactooligosaccharide, fructo-oligosaccharide, mannan oligosaccharide, and the like.

Sugar alcohols include, for example, erythritol, threitol, arabinitol, xylitol, mannitol, and the like.

Polysaccharides include, for example, starches such as corn starch, and the like or its derivatives, alginic acid, cellulose, dextrin, glucan, inulin, chitosan, hyaluronic acid, chondroitin sulfate, and the like. As for a polysaccharide, it is preferable to use a polysaccharide having low crystallinity. Moreover, when the hydrophilic impurities exhibit acidity, it is preferable to use a basic polysaccharide such as chitosan, and when the hydrophilic impurities exhibit basicity, it is preferable to use an acidic polysaccharide such as alginic acid, hyaluronic acid, chondroitin sulfate, and the like from the viewpoint of the effectiveness of increasing the purity.

The hydroxyl group-containing polymers include, for example, glycols such as polyethylene glycol, polyethylene oxide, polyethylene glycol/polypropylene glycol copolymer, polyethylene oxide/polypropylene oxide copolymer, and the like, as well as polymers or copolymers of polyvinyl alcohol, hydroxyethyl acrylate, and the like.

Phenols include, for example, phenol, catechol, resorcinol, hydroquinone, pyrogallol, and the like; however, from the viewpoint of safety, it is preferable to use polyphenols such as gallic acid, catechin, flavonoids, quercetin, anthocyanin, ellagic acid, and the like. As for these (poly)phenols, when the hydrophilic impurities exhibit basicity, the effect of increasing the purity is particularly good.

Aldehydes include, for example, glyceraldehyde, and the like.

Ketones include, for example, dihydroxyacetone, polyvinylpyrrolidone, and the like.

Carboxylic acids include, for example, saturated monofatty acids such as capric acid, myristic acid, lauric acid, palmitic acid, stearic acid, and the like; non-saturated monofatty acids such as trans-crotonic acid; hydroxylic acids such as lactic acid, malic acid, glycolic acid, tartaric acid, citric acid, and the like; aromatic carboxylic acids such as benzoic acid, phthalic acid, salicylic acid, gallic acid, and the like; dicarboxylic acids such as oxalic acid, malonic acid, succinic acid, glutaric acid, adipic acid, fumaric acid, maleic acid, and the like; polycarboxylic acids such as poly (meta) acrylic acid, polyglutamic acid, polyaspartic acid, uncrosslinked poly (meta)acrylic acid, and the like; crosslinked polyacrylate such as Carbomer, and the like; alkyl-modified crosslinked polyacrylate such as alkyl-modified carboxyvinyl polymer (acrylate/C10-30 alkyl acrylate crosspolymer), as well as their anhydrides.

Esters include, for example, hydrophilic or water-soluble polyester polymers, (meta)acrylic acid/(meta)acrylic ester copolymer, crosslinked (meta)acrylic acid/(meta)acrylic ester copolymer, glycolic acid polymer and copolymer, and the like.

Ethers include, for example, glycols such as epoxy resins, polyethylene glycol, polyethylene oxide, polyethylene glycol/polypropylene glycol copolymer, polyethylene oxide/polypropylene oxide copolymer, and the like. Among these, the epoxy resin powder has an excellent effect of trapping the impurities through the reaction of epoxy-amine when the hydrophilic impurities have an amino group, and through the reaction of epoxy-carboxylic acid when the hydrophilic impurities have a carboxylic acid group, and is useful in the purification-increasing treatment according to the present invention.

Amino acids include alanine, arginine, asparagine, aspartic acid, cysteine, glutamine, glutamic acid, glycine, histidine, leucine, isoleucine, lysin, phenylalanine, proline, serine, threonine, tryptophan, tyrosine, valine, aspartame, pyrrolidone carboxylic acid, and the like. When the hydrophilic impurities exhibit acidity, it is preferable to use a basic amino acid such as lysin, arginine, hystidine, tryptophan, ornithine, and the like, and when the hydrophilic impurities exhibit basicity, it is preferable to use an acidic amino acid such as glutamic acid, aspartic acid, and the like from the viewpoint of the effectiveness of increasing the purity.

Amines include purine bases such as adenine, guanine, and the like; pyrimidine bases such as cytosine, and the like, various amino resins, amino group-containing polymers, and the like. As for the amines described above, when the hydrophilic impurities exhibit acidity, the effect of increasing the purity is particularly good.

Amides include polyamides, polyacrylamides, crosslinked polyacrylamides, polyoxazoline, nylon powder, and the like.

While the hydrogen bond-forming substance is preferably in the form of a crystal, it is not limited thereto. Moreover, as described above, the hydrogen bond-forming substance may have a form of a hydrate having a hydration water molecule in the composition formula.

The ionic bond-forming substance is not particularly limited as long as it is a solid that can form an ionic bond, and is preferably selected from hydrophilic low molecular organic compounds not containing a silicon atom, uncrosslinked hydrophilic high molecular organic compounds not containing a silicon atom, and crosslinked hydrophilic high molecular organic compounds not containing a silicon atom, and the like. Moreover, as described above, the ionic bond-forming substance may have a form of a hydrate having a hydration water molecule in the composition formula.

The ionic bond-forming substance preferably has a functional group that enables ionic bonding such as a carboxyl group, amino group, carboxylic acid anionic group, sulfonic acid anionic group, quaternary ammonium cationic group, and the like, and may be salts made of metallic elements (mainly cations) and non-metallic elements (mainly anions), salts made of metallic elements (mainly cations) and non-metallic polyatomic ions (mainly anions), and salts made of non-metallic polyatomic ions (mainly cations) and non-metallic elements (mainly anions). The ionic bond-forming substance can be selected from, for example, inorganic salts, organic acid salts, quaternary ammonium salts, betaine compounds, polyacrylate-based polymers, vinyl acetate-acrylate-based polymer, isobutylene-maleic acid-based polymer, acrylamide/(meta)acrylate-based polymer, quaternary ammonium polymer of acrylamide/dimethyl aminoethyl (meta)acrylate copolymer, the salts and partially neutralized substances of a crosslinked polyacrylate such as a carboxyvinyl polymer (Carbomer), the salts and partially neutralized substances of an alkyl-modified crosslinked polyacrylate such as an alkyl-modified carboxyvinyl polymer (acrylate/C10-30 alkyl acrylate crosspolymer), the salts and partially neutralized substances of a crosslinked poly (2-acrylamide-2-methylpropanesulfonic acid) polymer, and the like. The ionic bond-forming substance is preferably a solid particulate at room temperature.

The hydrate of the hydrogen bond-forming substance or the ionic bond-forming substance is a substance containing a water molecule in the structure, and can be suitably used as the solid particles of the present invention. Specifically, the substance may be an organic compound or an inorganic compound, for example, trehalose dihydrate, gallic acid monohydrate, trisodium citrate dihydrate, catechin hydrate, ellagic acid dihydrate, and the like are preferred examples. In addition, for example, hydrated inorganic salt is also preferable. The hydrated inorganic salt is an inorganic salt having a hydration function, and may take the form of an anhydrous salt or may take the form of a hydrated salt. The hydrated inorganic salt includes, for example, sulfates, such as sodium sulfate, calcium sulfate, copper sulfate, and the like; carbonates such as sodium carbonate and the like; nitrates such as nickel nitrate, and the like; phosphates such as calcium phosphate, and the like; and chlorides such as calcium chloride, magnesium chloride, and the like. The inorganic salt may be water soluble or may be water insoluble, as long as the inorganic salt is a solid in an environment where the organic salt is in contact with the hydrophilic impurities.

The diameter of the solid particles is not particularly limited. This is because the form of most of the particles cannot be expressed in a simple and quantitative manner like a sphere or cube, but the form is complex and irregular, due to which the particle diameter cannot be defined directly, and therefore, when the measurement principle varies, the definition of the particle diameter, that is, the scale itself that acts as the measurement standard varies, and thus, generally, the particle size distribution of the solid particles depends on the measurement principle. Moreover, depending on the type and property of the solid particle used, there may be a difference in the appropriate particle diameter. While publicly known techniques, such as the image analysis method, Coulter method, centrifugal sedimentation method, and laser diffraction/scattering method can be used as the principle of particle size distribution measurement of solid particles, when the particle size of 50% of the integrated value of the cumulative percentage by weight is considered to be the median particle size (median diameter), the median particle size is preferably within the range of greater than or equal to 1 μm and less than or equal to 1 mm, as a standard. Specifically, the median particle size of the solid particles is preferably in the range of 1 to 500 μm, more preferably from 5 to 200 μm, and even more preferably from 10 to 100 μm. In the case of large particles (group) with the median grain size exceeding 1 mm, the total surface area of a particle per unit mass reduces, and thus, the capacity of removing the hydrophilic impurities declines. Conversely, in the case of a group of fine particles of which the median particle size does not reach 1 μm, the total surface area becomes extremely large, and thus, clogging tends to occur even though the particles have an excellent capacity of removing hydrophilic impurities, and because a lot of time, cost, and additional efforts are required for filtering from the polyhydric alcohol derivative-modified silicone, the appeal from the viewpoint of large-size production on the commercial scale declines. It is noted that the median particle size here means the median diameter in the volume (weight) particle size distribution measured using a laser diffraction/scattering type particle size distribution measurement instrument.

As an example of the solid particles, a preferable diameter of diatomaceous earth that is one mineral derived material is described. While dried products, burned products, flux-fired products, or their acid-treated purified products can be preferably used as diatomaceous earth, solid particles with a large median particle size have almost no effect on the purification-increasing treatment of the present invention, and are not applicable as solid particles in the present invention. For example, while the group of solid particles of diatomaceous earth exceeding the median particle size of 40 µm have almost no effect, the group of solid particles of diatomaceous earth having a median particle size of approximately 30 µm show an effect of increasing the purity according to the present invention. Also, the group of solid particles of diatomaceous earth having a median particle size of approximately 20 to 10 µm have an excellent effect of increasing the purity. Therefore, diatomaceous earth preferably has a median particle size of 1 to 35 µm, more preferably a median particle size of 5 to 30 µm, and most preferably a median particle size of 10 to 20 µm.

The solid particles preferably finally have a layer form. The layer of the solid particles can be formed by, for example, mixing and stirring a mixture containing a liquid polyhydric alcohol derivative-modified silicone and hydrophilic impurities with the solid particles, allowing the product to stand for a predetermined time, and then precipitating the solid particles. As a result, the solid particles can effectively capture the hydrophilic impurities, and the hydrophilic impurities, which are the cause of turbidity of the mixture, can either be incorporated in the layer, or can be absorbed and retained in the layer. Moreover, capturing of the hydrophilic impurities by the solid particles is also possible by a method of filling the solid particles beforehand into a casing having an exit and an entry, setting a filter at the exit and the entry so that there is no leakage, and repeatedly passing the mixture containing the liquid polyhydric alcohol derivative-modified silicone and hydrophilic impurities through the casing. In such a case, the layer of the solid particles is formed beforehand in the casing.

The solid particles that have captured the hydrophilic impurities are preferably separated from the liquid polyhydric alcohol derivative-modified silicone by an appropriate means. While the solid particles are solid, the polyhydric alcohol derivative-modified silicone is liquid, and therefore, a publicly known solid-liquid separation means, such as filtering, centrifugal separation, and the like. can be used as the separation means. Filtering is preferable for implementation on a commercial scale. Therefore, as a step of separating the polyhydric alcohol derivative-modified silicone and the hydrophilic impurities according to the present invention, a filtering step including a filtering material is preferred, and filtering the solid particles by the filtering material to separate from the liquid polyhydric alcohol derivative-modified silicone is more preferable.

For example, when the solid particles have a particle size distribution in the range of greater than or equal to 0.5 µm, the liquid polyhydric alcohol derivative-modified silicone and the solid particles can be separated by a filtering material that can remove particles having a size of greater than or equal to 0.5 µm. Specifically, by filtering the solid particles using the filtering material after bringing the mixture into contact with the solid particles, the solid particles can be separated from the mixture. Since the hydrophilic impurities are captured with the solid particles, the hydrophilic impurities can thus be separated from the mixture.

The filtering material for separating the solid particles from the polyhydric alcohol derivative-modified silicone is not particularly limited, and includes for example, a filter paper, woven fabric, nonwoven fabric, and the like configured by natural fibers such as cellulose, synthetic fibers such as nylon, polypropylene, polyethersulfone, cellulose acetate, PTFE, polyethylene terephthalate, and the like, stainless steel, glass fibers, and various fibers made of or their mixtures, or various filters made of the porous inorganic substances or porous inorganic substances.

In the above filtering step, it is preferable to further use a filtering aid. The filtering aid is preferably in powder form or fibrous form, and it is more preferable to use at least one filtering aid selected from activated carbon, diatomaceous earth, perlite, glass (particles or fibers), cellulose (powder or fibers), and their derivatives. It is noted that the solid particles can also be used as the filtering aid.

When the filtering aid is in powder form, the median particle size is preferably greater than or equal to 5 µm. Specifically, the median particle size of the filtering aid is preferably in the range of 5 to 100 µm, more preferably from 10 to 60 µm, and even more preferably from 20 to 50 µm. The median particle size can be measured by a publicly known measurement instrument by using the image analysis method, Coulter method, centrifugal sedimentation, and laser diffraction/scattering method. It is noted that the median particle size here means the median diameter in the volume (weight) particle size distribution measured using a laser diffraction/scattering type particle size distribution measurement instrument.

The separating step is preferably implemented within a range of 0 to 100° C., more preferably within a range of 15 to 80° C., and even more preferably within a range of 25 to 60° C.

In the present invention, in the above-described first aspect, it is preferred to bring the mixture of the liquid polyhydric alcohol derivative-modified silicone and the hydrophilic impurities into contact with the solid particles in the capturing step after diluting with a solvent, which is a good solvent of the polyhydric alcohol derivative-modified silicone and a poor solvent of the hydrophilic impurities.

The solvent can be selected from those that are a good solvent of the liquid polyhydric alcohol derivative-modified silicone and a poor solvent of the hydrophilic impurities, and may be, for example, a hydrophobic solvent. Due to the dilution of the mixture containing the liquid polyhydric alcohol derivative-modified silicone and hydrophilic impurities by the solvent, the hydrophilic impurities coagulate with each other so that the size increases, which makes it easier to be captured with the solid particles, and also making it easier to be separated from the liquid polyhydric alcohol derivative-modified silicone. Moreover, by diluting the liquid polyhydric alcohol derivative-modified silicone with the solvent, the viscosity of the polyhydric alcohol derivative-modified silicone that is extremely viscous in the undiluted state can be effectively reduced, which also simplifies the solid-liquid separation operation.

As for the solvent that is a good solvent of the liquid polyhydric alcohol derivative-modified silicone and a poor solvent of the hydrophilic impurities, a hydrophobic solvent is preferred, which includes, for example, aliphatic hydrocarbons such as pentane, heptane, and the like; aromatic hydrocarbons such as benzene, toluene, and the like; and silicones such as dimethyl polysiloxane, methylphenyl polysiloxane, cyclic silicones, caprylyl methicone, and the like. The solvent is preferably volatile.

When dilution is performed by a solvent, the solution of a high-purity polyhydric alcohol derivative-modified silicone can be produced easily, and the method is suitable for the production of a composition of the high-purity polyhydric alcohol derivative-modified silicone on a commercial scale.

On the other hand, the production method of the present invention may include a step of removing the solvent by heating and/or decompressing the mixture liquid after the separating step. The heating temperature is not particularly limited, for example, the heating temperature may be set to 40 to 120° C. Also, the degree of decompression is not particularly limited, for example, the degree of decompression may be set to 0.01 to 0.8 atmospheric pressure. Further, the heating time and decompression time are not particularly limited and, for example, can be set to 10 minutes to 24 hours.

When the solvent is removed, the high-purity polyhydric alcohol derivative-modified silicone can be produced easily, and the method is suitable for the production of a high-purity polyhydric alcohol derivative-modified silicone on a commercial scale.

The first aspect of the present invention can be implemented, for example, by filtering a composition obtained by mixing the solid particles in an impurity-containing composition (mixture) containing a liquid polyhydric alcohol derivative-modified silicone and hydrophilic impurities, and then removing the solid particles from the composition. Thus, the liquid polyhydric alcohol derivative-modified silicone and hydrophilic impurities can be separated.

The hydrophilic impurities are not particularly limited as long as the impurities are hydrophilic, and are typically, a polyhydric alcohol derivative (polyhydric alcohol modifier), which is one of the raw materials of producing a polyhydric alcohol derivative-modified silicone, or a substance originating therefrom. The polyhydric alcohol derivative includes, for example, a polyhydric alcohol derivative having one reactive unsaturated group of a polyhydric alcohol derivative, and the like, having a carbon-carbon double bond at a terminal of the molecular chain per molecule, as described later, and preferably a mono unsaturated ether compound of a polyhydric alcohol. Moreover, substances originating from the polyhydric alcohol derivative include polyhydric alcohols. For example, when the polyhydric alcohol modifier is a monoallyl etherified polyhydric alcohol, after the synthesis reaction of the polyhydric alcohol derivative-modified silicone, the majority of the excess amount of the modifier is isomerized into monopropenyl etherified polyhydric alcohol, and since this is a source of generation of odorization, it is preferable to implement the acid treatment step described later after the synthesis step to perform hydrolysis of the propenylether, and thus converting the monopropenyl etherified polygydric alcohol into polyhydric alcohol. Therefore, after the acid treatment step, the polyhydric alcohol itself is included in the hydrophilic impurity. Since the polyhydric alcohol itself has a low affinity to the polyhydric alcohol derivative-modified silicone as compared to the mono unsaturated ether compound of the polyhydric alcohol, the polyhydric alcohol hardly get dissolved in the modified silicone. Therefore, by implementing the step of increasing the purity by the solid particles of the present invention, after the acid treatment step, the hydrophilic impurities can be captured and removed more effectively, and a further increase in the purity can be achieved.

Hereinafter, the liquid polyhydric alcohol derivative-modified silicone, which is the target of the present invention, will be described.

Polyhydric Alcohol Derivative-Modified Silicone

The polyhydric alcohol derivative-modified silicone to which the present invention is applicable is a silicone compound modified with a polyhydric alcohol derivative (preferably not a sugar derivative), is a liquid composition, and is preferably a liquid at least at a temperature of 100° C. The chemical structure or the like is not particularly limited as long as the composition satisfies this condition.

In the present invention, a "liquid form" or a "liquid" means that after the liquid surface of an organopolysiloxane in a prescribed container is placed horizontally and the vessel is then inclined, the liquid surface can once again become horizontal after one hour, preferably after 30 minutes, and more preferably after 10 minutes. Here, "horizontal" means to form a plane that intersects the direction of gravitational force at a right angle. The polyhydric alcohol derivative-modified silicone is preferably a liquid at least at 100° C. but more preferably also exhibits liquidity in a range of lower than or equal to 100° C. to room temperature. Specifically, the polyhydric alcohol derivative-modified silicone is preferably a liquid at 80° C., more preferably a liquid at 40° C., and even more preferably a liquid at room temperature (25° C.). Compositions that are in the liquid state at a temperature of higher than or equal to 100° C. are, of course, included in the scope of the liquid polyhydric alcohol derivative-modified silicone, but a polyhydric alcohol derivative-modified silicones that demonstrate liquidity when heated to, for example, 100° C. even if they are in a semi-gelatinous form or a soft solid form without fluidity at room temperature (25° C.) or lower are also included.

The polyhydric alcohol derivative-modified silicone can be a polyhydric alcohol derivative-modified silicone represented by the following general formula (1):

[Chemical Formula 10]

$$R^1_a R^2_b L^1_c Q_d SiO_{(4-a-b-c-d)/2} \quad (1)$$

(wherein, $R^1$ represents a monovalent organic group (however, excluding $R^2$, L, and Q), a hydrogen atom or a hydroxyl group; $R^2$ represents a substituted or unsubstituted, straight or branched monovalent hydrocarbon group having from 9 to 60 carbons, or a chain organosiloxane group represented by the following general formula (2-1):

[Chemical Formula 11]

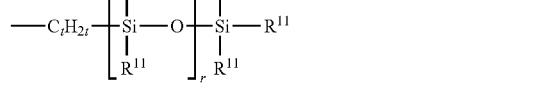

(2-1)

(wherein, $R^{11}$ are each independently a substituted or unsubstituted monovalent hydrocarbon group having from 1 to 30 carbons, a hydroxyl group, or a hydrogen atom, and at least one of $R^{11}$ is the monovalent hydrocarbon group; t is a number in a range of 2 to 10; and r is a number in a range of 1 to 500), or the following general formula (2-2):

[Chemical Formula 12]

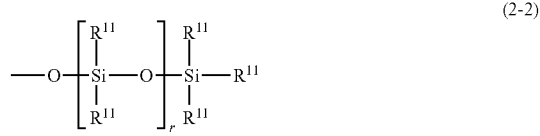

(2-2)

(wherein, $R^{11}$ and r are synonymous with those described above); $L^1$ represents a silylalkyl group having a siloxane dendron structure represented by the following general formula (3) when i=1:

[Chemical Formula 13]

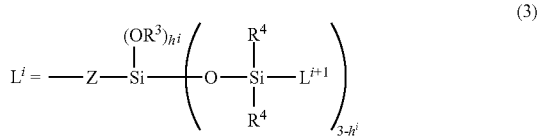

(3)

(wherein, $R^3$ each independently represent a substituted or unsubstituted, straight or branched monovalent hydrocarbon group having from 1 to 30 carbons; $R^4$ each independently represent an alkyl group or phenyl group having from 1 to 6 carbons; Z represents a divalent organic group; i represents a generation of the silylalkyl group represented by $L^i$ and is an integer of 1 to k when k is the number of generations that is the number of repetitions of the silylalkyl group; the number of generations k is an integer from 1 to 10; $L^{i+1}$ is the silylalkyl group when i is less than k, and $R^4$ when i=k; and $h^i$ is a number in a range of 0 to 3); Q represents a polyhydric alcohol derivative group; and a, b, c, and d are numbers in the ranges of $1.0 \leq a \leq 2.5$, $0 \leq b \leq 1.5$, $0 \leq c \leq 1.5$, and $0.0001 \leq d \leq 1.5$, respectively).

Here, when the polyhydric alcohol derivative-modified silicone represented by general formula (1) has the long chain organic group or the chain organosiloxane group represented by $R^2$, b is a number greater than 0, preferably $0.0001 \leq b \leq 1.5$, and more preferably $0.001 \leq b \leq 1.5$. Similarly, when the polyhydric alcohol derivative-modified silicone represented by general formula (1) has a silylalkyl group having the siloxane dendron structure represented by $L^1$, c is a number greater than 0, preferably $0.0001 \leq c \leq 1.5$, and more preferably $0.001 \leq c \leq 1.5$.

The polyhydric alcohol derivative-modified silicone preferably has a long chain organic group or chain organosiloxane group represented by $R^2$ or a siloxane dendron structure represented by $L^1$ together with the polyhydric alcohol derivative group serving as Q.

At this time, the suitable values of b and c are represented as follows by essential functional groups.

(1) When there is a group represented by $R^2$: $0.001 \leq b \leq 1.5$ and $0 \leq c \leq 1.5$.

(2) When there is a group represented by $L^1$: $0 \leq b \leq 1.5$ and $0.001 \leq c \leq 1.5$.

(3) When there are both a group represented by $R^2$ and a group represented by $L^1$: $0.001 \leq b \leq 1.5$ and $0.001 \leq c \leq 1.5$ The monovalent organic groups represented by $R^1$ in general formula (1) can be the same or different and are not particularly limited as long as the groups are not the functional groups of $R^2$, $L^1$, and Q. However, the groups are preferably a substituted or unsubstituted, straight-chain or branched monovalent hydrocarbon group having from 1 to 8 carbon atoms, a (poly)oxyalkylene group represented by —$R^{5'}O(AO)_nR^6$ (in the formula, AO represents an oxyalkylene group having from 2 to 4 carbons; $R^{5'}$ represents a substituted or unsubstituted, straight-chain or branched divalent hydrocarbon group having from 3 to 5 carbons; $R^6$ represents a substituted or unsubstituted, straight-chain or branched monovalent hydrocarbon group having from 1 to 24 carbons and hydrogen atoms or a substituted or unsubstituted, straight-chain or branched acyl group having from 2 to 24 carbons; and n is from 1 to 100), an alkoxy group, a hydroxyl group, or a hydrogen atom. However, not all of the $R^1$ are hydroxyl groups, hydrogen atoms, alkoxy groups, or (poly)oxyalkylene groups.

Examples of a monovalent hydrocarbon group having from 1 to 8 carbons include, for example, alkyl groups such as a methyl group, ethyl group, propyl group, butyl group, pentyl group, hexyl group, heptyl group, octyl group, and the like; cycloalkyl groups such as a cyclopentyl group, cyclohexyl group, and the like; alkenyl groups such as a vinyl group, allyl group, butenyl group, and the like; aryl groups such as a phenyl group, tolyl group, and the like; aralkyl groups such as a benzyl group; and groups wherein the hydrogen atoms bonded to the carbon atoms of these groups are substituted at least partially by fluorine or a similar halogen atom, or an organic group having an epoxy group, a glycidyl group, an acyl group, a carboxyl group, an amino group, a (meth)acryl group, a mercapto group, or the like (however, the total number of carbons is from 1 to 8). The monovalent hydrocarbon group is preferably a group other than an alkenyl group, and is particularly preferably a methyl group, an ethyl group, or a phenyl group. Additionally, examples of the alkoxy group include a methoxy group, an ethoxy group, an isopropoxy group, a butoxy group, and similar lower alkoxy groups; a lauryl alkoxy group, a myristyl alkoxy group, a palmityl alkoxy group, an oleyl alkoxy group, a stearyl alkoxy group, a behenyl alkoxy group, and similar higher alkoxy groups; and the like.

Particularly, the $R^1$ moieties are preferably monovalent hydrocarbon groups having from 1 to 8 carbons and that are free of unsaturated aliphatic bonds or monovalent fluorinated hydrocarbon groups. Examples of the monovalent hydrocarbon group not having unsaturated aliphatic bonds belonging to the $R^1$ moiety include alkyl groups such as methyl groups, ethyl groups, propyl groups, butyl groups, pentyl groups, and hexyl groups; aryl groups such as phenyl groups, tolyl groups, and xylyl groups; and aralkyl groups such as benzyl groups. Examples of the monovalent fluorinated hydrocarbon group include perfluoroalkyl groups such as trifluoropropyl groups, and pentafluoroethyl groups. From an industrial perspective, $R^1$ is preferably a methyl group, an ethyl group, or a phenyl group, and more preferably from 90 mol % to 100 mol % of all the $R^1$ moieties are selected from methyl groups, ethyl groups, or phenyl groups.

The polyhydric alcohol derivative-modified silicone aims at imparting additional functionality, and it is possible to introduce or design a modified group other than a hydrophilic group (-Q), particularly a short chain or medium chain hydrocarbon based group, as $R^1$. Specifically, when $R^1$ is a substituted monovalent hydrocarbon group, a substituent can be preferably selected in accordance with desired characteristics and uses. For example, when using the polyhydric alcohol derivative-modified silicone as a cosmetic composition or a fiber treating agent starting material, it is possible to introduce an amino group, amide group, aminoethyl aminopropyl group, carboxyl group, and the like, as the substituted group of a monovalent hydrocarbon group, for the purpose of improving the sensation during use, feeling to touch, persistence, and the like.

The substituted or unsubstituted, straight or branched monovalent hydrocarbon group having from 9 to 60 carbons of $R^2$ of general formula (1) is a long chain hydrocarbon group or a chain organosiloxane group represented by general formula (2-1) or (2-2). By introducing this group at the main chain and/or side chain of polysiloxane, it is possible to further improve the affinity, emulsifiability, and dispersibility, and further, the sensation during use of various components such as an oil agent, powder, or the like incorporated in an external use preparation or a cosmetic composition. Furthermore, because the monovalent long chain hydrocarbon group or chain organopolysiloxane group is a hydrophobic functional group, the compounding stability and the compatibility with organic oils having a high content of alkyl groups are further improved. $R^2$ may be all the monovalent long chain hydrocarbon group or all the chain organopolysiloxane group, or may be a functional group of both of these groups. In the polyhydric alcohol derivative-modified silicone, it is particularly preferable that part or all of $R^2$ is a monovalent long chain hydrocarbon group, and by having such a monovalent long chain hydrocarbon group in a molecule, the polyhydric alcohol derivative-modified silicone exhibits superior compatibility not only with silicone oil, but with non-silicone oil with a high alkyl group content as well. For example, it is possible to obtain an emulsion and a dispersion with superior stability over time and thermal stability, which are made of non-silicone oil.

Substituted or unsubstituted, straight or branched monovalent hydrocarbon groups that are represented by $R^2$ of general formula (1), that are bonded to silicon atoms, and that have from 9 to 60 carbons, may be the same or different. Furthermore, the structure thereof is selected from among straight chain, branched, and partially branched. In the present invention, an unsubstituted straight chain monovalent hydrocarbon group is particularly preferably used. An unsubstituted monovalent hydrocarbon group can be, for example, an alkyl group, aryl group, or aralkyl group having from 9 to 60 carbons, preferably from 9 to 30 carbons, and more preferably from 10 to 25 carbons. On the other hand, examples of the substituted monovalent hydrocarbon group include perfluoroalkyl groups, aminoalkyl groups, amide alkyl groups, and ester groups having from 9 to 30 carbons, preferably from 10 to 24 carbons. Additionally, the carbon atoms of the monovalent hydrocarbon groups may be partially substituted with alkoxy groups, and examples of the alkoxy groups include methoxy groups, ethoxy groups, and propoxy groups. This type of monovalent hydrocarbon group is particularly preferably an alkyl group having from 9 to 30 carbons, and an example thereof is a group represented by the general formula —$(CH_2)_{v'}$—$CH_3$ ($v'$ is a number in a range of 8 to 29). An alkyl group having from 10 to 24 carbons is particularly preferable.

The chain organosiloxane group in general formula (2-1) or (2-2) has a straight chain polysiloxane chain structure, unlike a silylalkyl group, which has a siloxane dendron structure. In general formula (2-1) or (2-2), $R^{11}$ are each independently a substituted or unsubstituted monovalent hydrocarbon group having from 1 to 30 carbons, a hydroxyl group, or a hydrogen atom. The substituted or unsubstituted monovalent hydrocarbon group having from 1 to 30 carbons is preferably an alkyl group having from 1 to 30 carbons, an aryl group having from 6 to 30 carbons, an aralkyl group having from 6 to 30 carbons, or a cycloalkyl group having from 6 to 30 carbons, and is exemplified by an alkyl group such as a methyl group, ethyl group, propyl group, butyl group, pentyl group, hexyl group, heptyl group, octyl group, and decyl group; a cycloalkyl group such as a cyclopentyl group, and cyclohexyl group; and an aryl group such as a phenyl group, and tolyl group. The hydrogen atoms bonded to the carbon atoms of these groups may be substituted at least partially by fluorine or a similar halogen atom, or an organic group containing an epoxy group, acyl group, carboxyl group, amino group, methacryl group, mercapto group, or the like. A methyl group, a phenyl group, or a hydroxyl group is particularly preferable as $R^{11}$. A configuration in which a part of $R^{11}$ is a methyl group and another part of $R^{11}$ is a long chain alkyl group having from 8 to 30 carbons is also preferable.

In general formula (2-1) or (2-2), t is a number in a range of 2 to 10; r is a number in a range of 1 to 500; and r preferably is a number in a range of 2 to 500. Such a straight chain organosiloxane group is hydrophobic. From the perspective of compatibility with various oil agents, r preferably is a number in a range of 1 to 100, and particularly preferably is a number in a range of 2 to 30.

A silylalkyl group having a siloxane dendron structure shown by general formula (3) is a functional group that includes a structure wherein a carbosiloxane unit spreads in a dendrimer shape and that exhibits high water repellence. The silylalkyl group is well-balanced when combined with hydrophilic groups, and when an external use preparation or cosmetic composition that incorporates the polyhydric alcohol derivative-modified silicone is used, the silylalkyl group inhibits an unpleasant sticky feeling, and provides a refreshingly natural feeling to the touch. Additionally, the silylalkyl group having a siloxane dendron structure is chemically stable, and for this reason, the silylalkyl group is a functional group providing advantageous properties such as usability in combination with a wide range of components.

Examples of the substituted or unsubstituted, straight or branched monovalent hydrocarbon group having from 1 to 30 carbons (the $R^3$ moieties in general formula (3)) include alkyl groups such as methyl groups, ethyl groups, propyl groups, butyl groups, pentyl groups, hexyl groups, heptyl groups, and octyl groups; cycloalkyl groups such as cyclopentyl groups, and cyclohexyl groups; alkenyl groups such as vinyl groups, allyl groups, and butenyl groups; aryl groups such as phenyl groups, and tolyl groups; aralkyl groups such as benzyl groups; and groups wherein the hydrogen atoms bonded to the carbon atoms of these groups are substituted at least partially by fluorine or a similar halogen atom, or an organic group containing an epoxy group, a glycidyl group, an acyl group, a carboxyl group, an amino group, a methacryl group, a mercapto group, or the like (provided that the total number of carbon atoms is from 1 to 30).

Among the phenyl group or the alkyl group having from 1 to 6 carbons represented by $R^4$ in general formula (3), examples of the alkyl group having from 1 to 6 carbons include straight, branched, or cyclic alkyl groups such as methyl, ethyl, n-propyl, i-propyl, n-butyl, i-butyl, s-butyl, pentyl, neopentyl, cyclopentyl, and hexyl groups.

In the general formula (3), when i=k, $R^4$ is preferably a methyl group or a phenyl group. In particular, $R^4$ is preferably a methyl group when i=k.

From an industrial standpoint, the number of generations k is preferably an integer of 1 to 3, and more preferably is 1 or 2. In each of the number of generations, the group represented by $L^1$ is represented as follows. In the formulae, $R^3$, $R^4$, and Z are the same groups as described above.

When the number of generations is k=1, $L^1$ is represented by the following general formula (3-1).

[Chemical Formula 14]

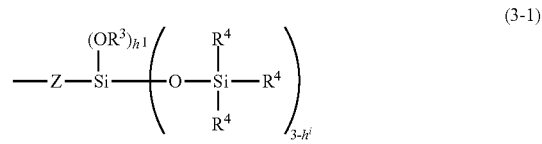

(3-1)

When the number of generations is k=2, $L^1$ is represented by the following general formula (3-2).

[Chemical Formula 15]

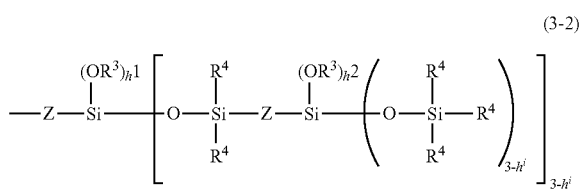

(3-2)

When the number of generations is k=3, $L^1$ is represented by the following general formula (3-3).

[Chemical Formula 16]

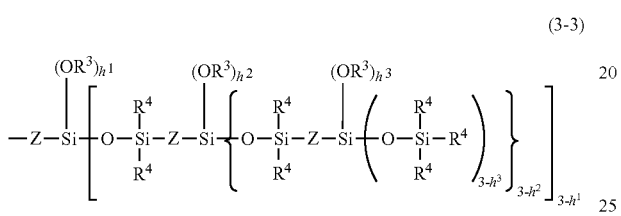

(3-3)

In the structures represented by the general formulae (3-1) to (3-3) when the number of generations is from 1 to 3, each of $h^1$, $h^2$ and $h^3$ moieties is independently a number in a range of 0 to 3. These $h^i$ moieties are, in particular, preferably a number in a range of 0 to 1, and $h^i$ moieties are particularly preferably 0.

In general formulae (3) and (3-1) to (3-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not limited to the functional groups described above. Preferably, Z are each independently a group selected from divalent organic groups represented by the following general formula:

—$R^7$—

—$R^7$—CO—

—$R^7$—COO—$R^8$—

—CO—$R^7$—

—$R^7$—OCO—$R^8$—

—$R^7$—CONH—$R^8$—

—$R^7$—$R^8$—.                [Chemical Formula 17]

Of these, Z in $L^1$ is preferably a divalent organic group expressed by general formula —$R^7$— that is introduced by a reaction between a silicon-bonded hydrogen atom and an alkenyl group. Likewise, Z is preferably a divalent organic group expressed by general formula —$R^7$—COO—$R^8$— that is introduced by a reaction between a silicon-bonded hydrogen atom and an unsaturated carboxylic ester group.

On the other hand, in the silylalkyl group represented by $L^i$, in which the number of generations k is at least 2, and $L^i$ is $L^2$ to $L^k$, Z is preferably an alkylene group having from 2 to 10 carbons or a divalent organic group represented by —$R^7$—COO—$R^8$— and is particularly preferably a group selected from an ethylene group, a propylene group, a methylethylene group, a hexylene group, and —$CH_2C(CH_3)COO$—$C_3H_6$—.

In the general formula described above, $R^7$ moieties are each independently a substituted or unsubstituted straight or branched chain alkylene group or alkenylene group having from 2 to 22 carbons or an arylene group having from 6 to 22 carbons. More specifically, examples of $R^7$ include straight alkylene groups such as an ethylene group, a propylene group, a butylene group, and a hexylene group; and branched alkylene groups such as a methylmethylene group, a methylethylene group, a 1-methylpentylene group, and a 1,4-dimethylbutylene group. $R^8$ is preferably a group selected from an ethylene group, a propylene group, a methylethylene group, and a hexylene group.

In the general formula described above, $R^8$ is preferably a group selected from divalent organic groups expressed by the following formula.

[Chemical Formula 18]

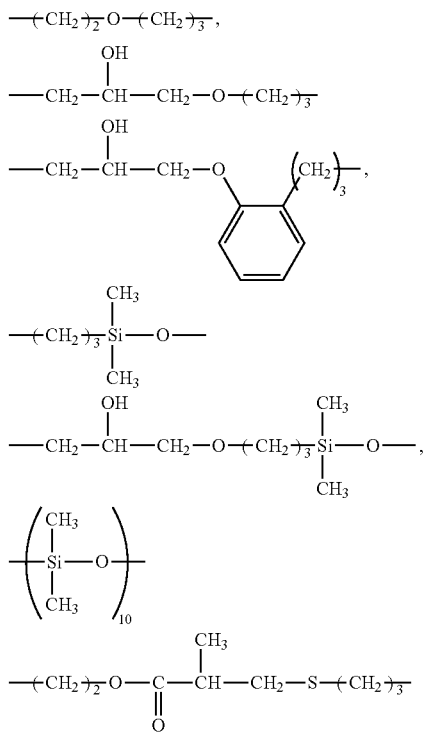

In general formula (1), Q is a polyhydric alcohol derivative group, and forms the hydrophilic site of the polyhydric alcohol derivative-modified silicone. The structure of Q is not limited provided that the structure has a polyhydric alcohol derivative site, but the polyhydric alcohol derivative residue is preferably bonded to the silicon atom via a divalent organic group.

The polyhydric alcohol derivative group is preferably a group derived from at least one glycerin (a glycerin derivative group). In such a case, the polyhydric derivative-modified silicone according to the present invention is modified by at least one glycerin derivative units.

Here, "glycerin derivative group" refers to a hydrophilic group having a (poly)glycerin structure, and refers to a hydrophilic group having a monoglycerin, a diglycerin, a triglycerin, a tetraglycerin, and at least a pentaglycerin structure. Additionally, the terminal hydroxyl group may be partially capped with an alkyl group. Furthermore, the (poly)glycerin structure may be straight or branched, and may be a structure that is branched in a dendritic manner as well.

The glycerin derivative group (Q) described above is preferably bonded to a silicon atom via a linking group that is at least divalent, and is preferably a glycerin derivative group comprising at least one hydrophilic unit having an average number of repetitions in the range of 1 to 10, the hydrophilic unit being selected from hydrophilic units represented by the following structural formulae (4-1) to (4-3).

[Chemical Formula 19]

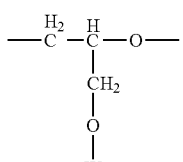
(4-1)

[Chemical Formula 20]

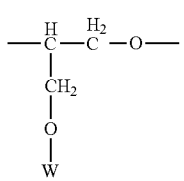
(4-2)

[Chemical Formula 21]

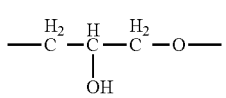
(4-3)

In formulae (4-1) and (4-2), W is a hydrogen atom or an alkyl group having from 1 to 20 carbons, and preferably is a hydrogen atom. Particularly, when W is a hydrogen atom, oxidation in air does not occur easily, and aldehydes such as formaldehyde and the like, and antigenic compounds such as formate esters and the like, are not easily produced over time while in storage. Therefore, when W is a hydrogen atom, there is a benefit of high environmental compatibility.

The hydrophilic units represented by structural formulae (4-1) to (4-3) are hydrophilic units included in a hydrophilic group derived from a hydrophilic compound selected principally from polyhydric alcohols include glycerin, polyglycerin (also called "polyglycerol"), and polyglycidyl ethers or compounds in which terminal hydroxyl groups thereof are partially capped by hydrocarbon groups. Furthermore, note that the glycerin derivative group (Q) may be a hydrophilic group that optionally comprises a hydrophilic structure (polyether structure) consisting of an oxyalkylene unit (for example, oxyethylene unit or oxypropylene unit) represented by the structural formula (4-4):

$$—C_{r'}H_{2r'}—O— \quad (4\text{-}4)$$

(r' is a number in the range of 1 to 6). However, to achieve a PEG-FREE formulation (a formulation not containing a compound having a polyoxyethylene (PEG) structure) as the overall formulation of a cosmetic or an external use preparation, it is preferable that the molecule does not contain an oxyalkylene structure containing at least two oxyalkylene units.

In the general formula (1), Q may be, for example, a hydrophilic group that does not have a branched structure such as a monoglycerin-modified group or a diglycerin-modified group, and may also be a hydrophilic group that has a partial branched structure in the functional group such as a polyglycerol group or a polyglycidylether group.

More specifically, Q may be a glycerin derivative group bonded to a silicon atom via a linking group that is at least divalent, comprising at least one linearly bonded hydrophilic unit selected from hydrophilic units represented by the above structural formulae (4-1) to (4-4) (however, the hydrophilic units constituting Q do not consist of only the structural formula (4-4)). Similarly, Q may be a glycerin derivative group that is bonded to a silicon atom via a linking group that is at least divalent, the glycerin derivative group containing at least two hydrophilic units of at least one selected from hydrophilic units represented by the above structural formulae (4-1) to (4-4) and having a branched unit selected from groups represented by the following structural formulae (4-5) to (4-7).

[Chemical Formula 22]

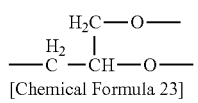
(4-5)

[Chemical Formula 23]

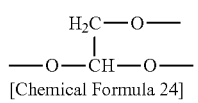
(4-6)

[Chemical Formula 24]

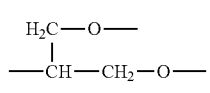
(4-7)

The at least one hydrophilic unit selected from the hydrophilic units represented by the above general formulae (4-1) to (4-4) are each independently bonded to the two oxygen atoms of the above structural formulae (4-5) to (4-7). The hydrophilic unit may further be bonded to a branch unit selected from groups represented by structural formulae (4-5) to (4-7). Moreover, the hydrophilic unit may be formed so as to have a dendroid-shape polyether structure, a polyglycerol structure, or a polyglycidyl ether structure obtained by branching into multiple generations. For example, the structure of a hydrophilic group Q which has one branch unit represented by structural formula (4-5) and two branch units represented by structural formula (4-7) and which is branched in a dendritic manner is shown below, but it goes without saying that dendroid-shape polyglycerol structures are not limited to this example.

[Chemical Formula 25]

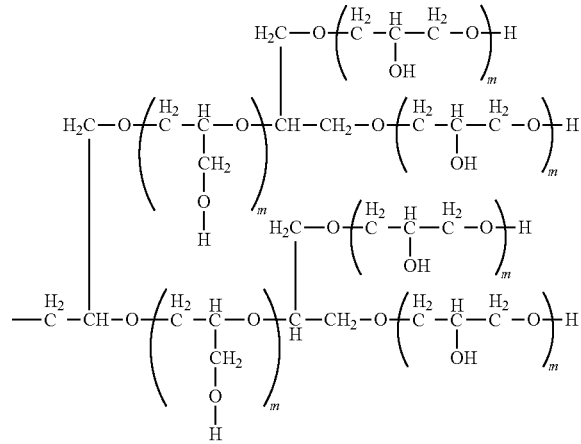

(In the formula, m is a number in a range of 0 to 50, provided that not all of the m moieties are 0).

The linking group that is at least divalent is a bonding site with respect to the silicon atom included in the hydrophilic group Q, and a structure thereof is not particularly limited. Examples thereof include, alkylene groups such as ethylene groups, propylene groups, butylene groups, and hexylene groups; alkylene phenylene groups such as ethylene phenylene groups, and propylene phenylene groups; alkylene aralkylene groups such as ethylene benzylene groups; alkyleneoxy phenylene groups such as ethyleneoxy phenylene groups, and propyleneoxy phenylene groups; alkyleneoxy benzylene groups such as methyleneoxy benzylene groups, ethyleneoxy benzylene groups, and propyleneoxy benzylene groups; and, furthermore, groups described below. Note that there are preferably from 0 to 3 and more preferably 0 or 1 ether bonds in the linking group that is at least divalent.

[Chemical Formula 26]

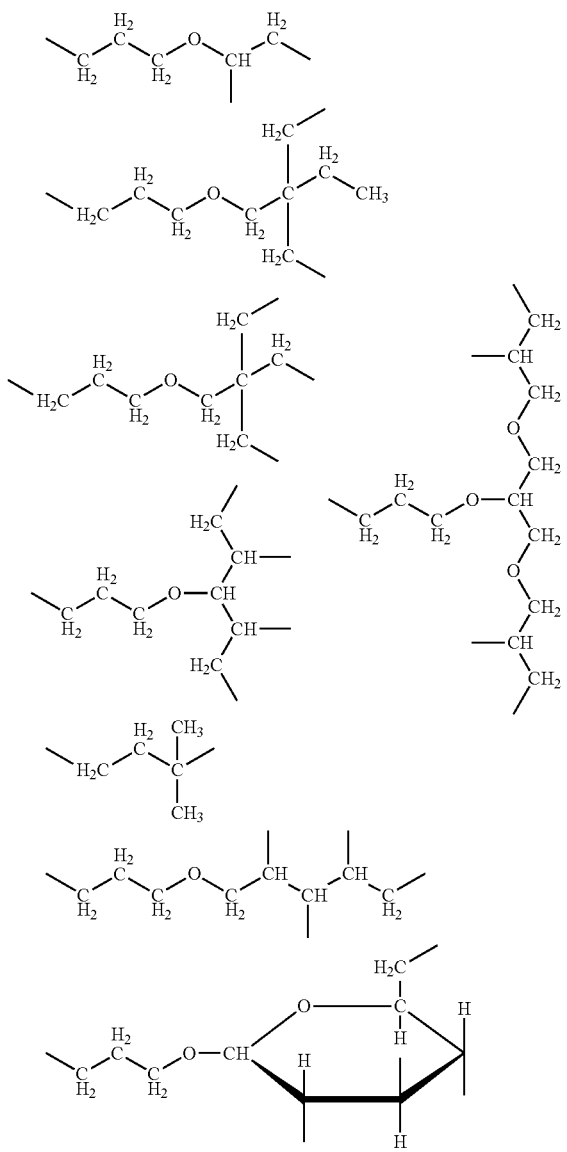

More preferably, Q is a hydrophilic group represented by the following structural formulae (4-8) to (4-11), and these are generally hydrophilic groups derived from polyglycerin-based compounds.

[Chemical Formula 27]

 (4-8)

 (4-9)

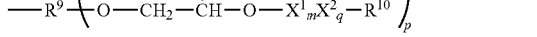 (4-10)

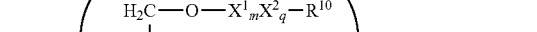 (4-11)

In formulae (4-8) to (4-11), $R^9$ is an organic group having (p+1) valence, and p is a number that is greater than or equal to 1 and less than or equal to 3. As the $R^9$, the same groups as the linking group that is at least divalent may be exemplified.

It is particularly preferable that p is 1, and as suitable $R^9$, a group selected from divalent organic groups represented by the following general formulae can be exemplified.

[Chemical Formula 28]

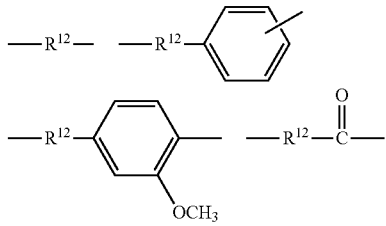

(In the formulae $R^{12}$ each independently may have a substituent, and are a straight or branched chain alkylene group or alkenylene group having from 2 to 22 carbons, or an arylene group having from 6 to 22 carbons.)

$X^1$ are each independently at least one hydrophilic unit selected from the hydrophilic units represented by the following general formulae (4-1-1) to (4-3), and in the above structural formulae (4-8) to (4-11), m is a number in a range of 1 to 5, and is particularly preferably a number in a range of 1 to 4.

[Chemical Formula 29]

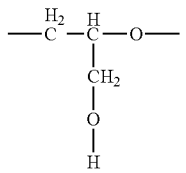 (4-1-1)

[Chemical Formula 30]

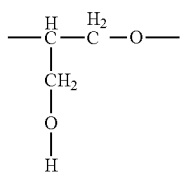 (4-2-1)

-continued

[Chemical Formula 31]

(4-3)

$X^2$ is any (poly)oxyethylene unit that Q may contain, and q is a number in the range 0 to 100. q is preferably a number in a range of 0 to 50 and preferably a range of 0 to 30. Note that $X^2$ may, in addition to a (poly)oxyethylene unit, also include a (poly)oxypropylene unit and/or (poly)oxybutylene unit. In this case, $X^2$ may be contained in Q as a (poly)oxyalkylene unit represented by the unit represented by the formula: $-(C_2H_4O)_{t1}(C_3H_6O)_{t2}(C_4H_8O)_{t3}-$ (wherein, t1, t2 and t3 are numbers satisfying $0 \le t1 \le 100$, $0 \le t2 \le 100$, and $0 \le t3 \le 50$, preferably numbers satisfying $0 \le t1 \le 50$, $0 \le t2 \le 50$, and $0 \le t3 \le 30$, and more preferably numbers satisfying $0 \le t1 \le 30$, $0 \le t2 \le 30$, and $0 \le t3 \le 10$). However, to achieve a PEG-FREE formulation as the overall formulation of a cosmetic or an external use preparation, it is preferable to not have an oxyalkylene structure in which the average number of repetitions of the oxyalkylene unit is at least 2, in the molecule.

Here, the manner in which $X^1$ and $X^2$ are bonded can be block or random. That is, the hydrophilic group Q may be a hydrophilic group in which hydrophilic segments, which are obtained by bonding hydrophilic units expressed by general formulae (4-2-1) to (4-3) above in a block manner, are bonded to hydrophilic segments comprising (poly)oxyalkylene units, and may be a hydrophilic group in which these constituent units are bonded in a random manner. For example, $X^1$ and $X^2$ may be bonded in a manner such as $-(X^2)_{m1}-X^1-(X^2)_{m2}-X^1-$ (wherein, $X^1$ and $X^2$ are synonymous with those described above, m1 and m2 are each independently a number in a range of 1 to 5, and particularly preferably, in a range of 1 to 4).

$R^{10}$ is a hydrogen atom or a group selected from the group consisting of glycidyl groups, acyl groups, and alkyl groups having from 1 to 20 carbons.

From the perspectives of gel formability and the thickening effect with respect to the oil agent component of the polyhydric alcohol derivative-modified silicone of the present invention and the perspective of the surface activity such as the emulsion and dispersion stability, a preferable hydrophilic group Q is a hydrophilic group derived from (poly)glycerin represented by the following structural formula (4-8-1).

[Chemical Formula 32]

(4-8-1)

In the formula, $R^{9'}$ is a divalent organic group, and can be a group synonymous with the group described above. $X^1$ and $R^{10}$ are synonymous with the groups described above, and in the formula (4-8-1), m is a number in a range of 1 to 5.

In the polyhydric alcohol derivative-modified silicone of the present invention, from the perspectives of thickening effect and gel formability with respect to the oil agent component, use as a surfactant (emulsifier), a moisturizer, or various treatment agents (powder dispersing agent or surface treatment agent), and particularly use as a powder treatment agent and a cosmetic composition starting material, the hydrophilic group Q is a hydrophilic group derived from a (poly)glycerin-based compound and is most preferably a hydrophilic group derived from (poly)glycerin. Specifically, the hydrophilic group Q is a (poly)glycerin monoallyl ether or a (poly)glyceryl eugenol, which are examples of hydrophilic groups derived from (poly)glycerin-based compounds having a monoglycerin, diglycerin, triglycerin, or tetraglycerin structure.

Furthermore, in the liquid organopolysiloxane according to the present invention, the glycerin derivative group is particularly preferably a diglycerin derivative group from the viewpoints of superior emulsification characteristics and superior powder dispersion characteristics, which enable the realization of a PEG-FREE formulation and affinity to oil agents.

A particularly preferred hydrophilic group Q is one in which the average number of repetitions m of glycerin units in the above structural formula (4-8-1) is in a range of 1.1 to 2.9, preferably in a range of 1.5 to 2.4, more preferably in a range of 1.8 to 2.2, and most preferably 2. At this time, in the formula, $R^{9'}$ is a divalent organic group, and can be a group synonymous with the group described above. $X^1$ and $R^{10}$ are also synonymous with the group described above. When the average number of repetitions of the hydrophilic unit is in the above range, there is the advantage that a water-in-oil emulsion composition that is stable over a long period in a wide range of oil agent systems and has small emulsified particle diameter can be obtained.

A diglycerin derivative group in which the number of glycerin unit repetitions, on average, is 2 is preferably contained in an amount exceeding 25 mass % of the total, relative to other glycerin derivative groups, more preferably greater than or equal to 50 mass %, and particularly preferably greater than or equal to 80 mass %. Most preferably, it is a pure product in which the purity of the diglycerin derivative groups exceeds 98 mass %. Furthermore, when the target is a PEG-FREE formulation, there must not be an oxyalkylene structure in which the average number of repetitions of the oxyalkylene unit in the same functional group is at least 2.

The polyhydric alcohol derivative group is more preferably a diglycerin derivative group represented by the following structural formula (5):

(5).

In the formula, $R^{27}$ is a divalent organic group, and is exemplified by the same divalent linking groups as described above. $R^{27}$ is preferably a divalent linking group not containing an oxyalkylene structure in which the average number of oxyalkylene unit repetitions is at least 2. X is at least one glycerin unit selected from hydrophilic units represented by the above structural formulae (4-1-1), (4-2-1), and (4-3). In the above structural formula (5), m is the number of glycerin unit repetitions, and on an average, is a number in a range of 1 to 4, and preferably in a range of 1.5 to 2.4. The preferred ranges of the number of glycerin unit repetitions are the same as described above.

Most preferably, the polyhydric alcohol derivative group is a diglycerin derivative group represented by the following general formula (5-1):

[Chemical Formula 33]

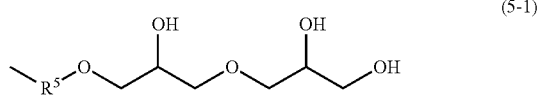

(5-1)

(wherein, $R^5$ represents a divalent organic group not having an oxyalkylene structure with an average value of a number of repetitions of oxyalkylene unit of at least 2) or general formula (5-2):

[Chemical Formula 34]

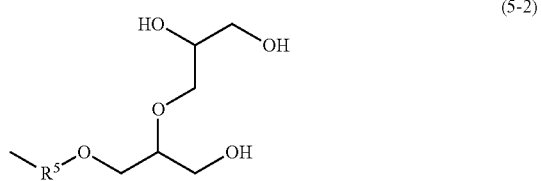

(5-2)

(In the formula, $R^5$ is synonymous with that described above.).

In the liquid organopolysiloxane according to the present invention, the diglycerin derivative group is preferably a hydrophilic group derived from diglycerin monoallyl ether or diglyceryl eugenol.

The bond position of the polyhydric alcohol derivative group (-Q) may be either the terminal or side chain of the polysiloxane that is the main chain; and the structure may have at least two polyhydric alcohol derivative groups per molecule of polyhydric alcohol derivative-modified silicone. Furthermore, the at least two polyhydric alcohol derivative groups can be the same or different polyhydric alcohol derivative groups. These at least two polyhydric alcohol derivative groups can be structured such that bonding occurs only in a side chain of the polysiloxane that is the main chain, only at a terminal, or in a side chain and at a terminal.

The polyhydric alcohol derivative-modified silicone having a polyhydric alcohol derivative group (-Q) represented by general formula (1) is preferably a liquid at a temperature of at least 100° C. In addition, the polysiloxane main chain may be a straight chain, a branched chain, or reticulated (including slightly crosslinked and elastomeric). With the production method of the present invention, it is possible to easily improve the opaque appearance of a composition and stabilize the composition as a translucent or transparent uniform liquid, not only in the case of a low-viscosity polyhydric alcohol derivative-modified silicone, but also in the case of a polyhydric alcohol derivative-modified silicone which has high viscosity and is in a solid form at room temperature (including gummy compositions having plasticity and poor fluidity).

The polyhydric alcohol derivative-modified silicone of the present invention particularly preferably is a polyhydric alcohol derivative-modified silicone having a straight chain polysiloxane structure represented by the following structural formula (1-1):

[Chemical Formula 35]

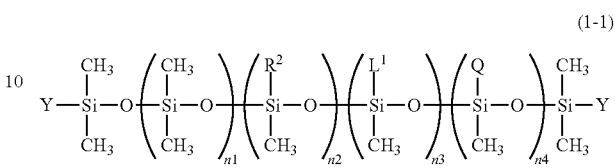

(1-1)

In the formula,
$R^2$, $L^1$, and Q are each independently synonymous with those described above;
Y is a group selected from the group consisting of a methyl group, $R^2$, $L^1$, and Q;
n1, n2, n3, and n4 are each independently a number in a range of 0 to 2,000, and n1+n2+n3+n4 is a number in a range of 0 to 2,000; however, when n4=0, at least one Y is Q.).

In formula (1-1), (n1+n2+n3+n4) preferably is a number in a range of 10 to 2,000, more preferably is in a range of 25 to 1500, and particularly preferably is a number in a range of 50 to 1000. n1 preferably is a number in a range of 10 to 2,000, more preferably is in a range of 25 to 1500, and particularly preferably is in a range of 50 to 1000. n2 preferably is a number in a range of 0 to 250, more preferably in a range of 0 to 150.

When $R^2$ is the long chain alkyl group, n2>1 is particularly preferable from the viewpoint of compatibility with oil agents other than silicone and powder dispersion stability. n3 preferably is a number in a range of 0 to 250, and it is particularly preferable that n3>1, and that it has at least one silylalkyl group (-$L^1$) having a siloxane dendron structure in a side chain portion from the viewpoint of powder dispersion stability and usage, as well as compatibility with silicone oil agents. n4 is a number in a range of 0 to 100, and preferably is in a range of 0 to 50. However, when n4=0, at least one Y needs to be Q. From the viewpoint of surface activity (emulsifiability) and powder dispersion ability, as well as powder surface treatment ability, it is particularly preferable to have at least one polyhydric alcohol derivative group Q in a molecule.

In the above structural formula (1-1), it is preferable that Q are each independently a glycerin derivative group represented by any of the above general formulae (4-8) to (4-11). In the polyhydric alcohol derivative-modified silicone, all Qs can be one glycerin derivative group that is represented by any of general formulae (4-8) to (4-11). Some of the Qs in a molecule can be glycerin derivative groups represented by any of the above general formulae (4-8) to (4-11). The remaining Qs may be another glycerin derivative group.

Furthermore, the polyhydric alcohol derivative-modified silicone can be a mixture of one or at least two polyhydric alcohol derivative-modified silicones represented by the above general formula (1). More specifically, the polyhydric alcohol derivative-modified silicone can be a mixture of at least two polyhydric alcohol derivative-modified silicones, with different types of modified groups, modification rate, and degree of polymerization of the siloxane main chain.

As the polyhydric alcohol derivative-modified silicone, the glycerin derivative-modified silicone represented by the following structural formula (1-1-1):

[Chemical Formula 36]

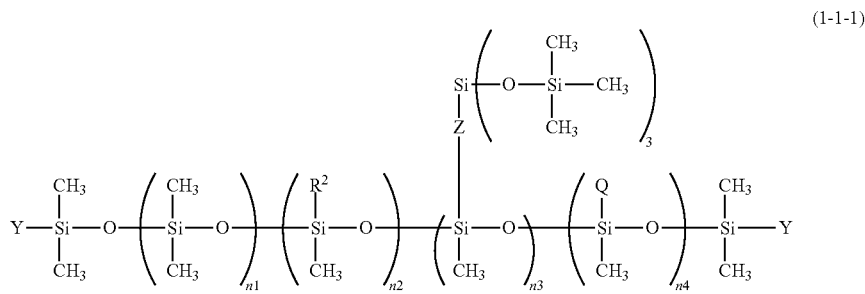

(1-1-1)

(wherein, $R^2$, Q, Y, Z, n1, n2, n3, and n4 are synonymous with those described above), or the following structural formula (1-1-2):

[Chemical Formula 37]

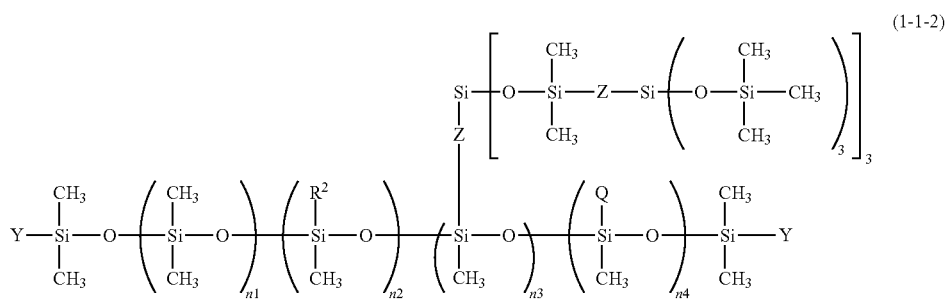

(1-1-2)

(wherein, $R^2$, Q, Y, Z, n1, n2, n3, and n4 are synonymous with those described above) is more preferable.

The modification rate of organopolysiloxane by the polyhydric alcohol derivative group, such as the glycerin derivative group, is preferably in a range of 0.001 to 50 mol %, more preferably in a range of 0.01 to 30 mol %, and even more preferably in a range of 0.1 to 10 mol %, of all functional groups bonded to the polysiloxane that is the main chain. Furthermore, in the polyhydric alcohol derivative-modified silicone represented by the structural formula (1-1), the modification rate (mol %) by the polyhydric alcohol derivative group is represented by the following formula: Modification rate (mol %)=(number of polyhydric alcohol derivative groups bonded to silicone atoms per molecule)/[6+2×(n1+n2+n3+n4)]×100. For example, in the case of a polyhydric alcohol derivative-modified silicone comprising dodecylsiloxane having 10 polyhydric alcohol derivative groups, of the 26 silicone atom bonded functional groups, 10 are modified with the polyhydric alcohol derivative group, so the modification rate by the glycerin derivative group is 38.5 mol %.

The uncrosslinked polyhydric alcohol derivative-modified silicone can be obtained by, for example, reacting, in the presence of a hydrosilylation reaction catalyst, (a) a polyhydric alcohol derivative having one reactive unsaturated group per molecule, (b) organopolysiloxane having silicon atom bonded hydrogen atoms, and (c) an organic compound having one reactive unsaturated group per molecule, and if necessary, (d) a siloxane dendron compound having one reactive unsaturated group per molecule, and/or (e) a long chain hydrocarbon compound or a chain organopolysiloxane compound having one reactive unsaturated group per molecule. The above-described reactive unsaturated group preferably is an unsaturated functional group having a carbon-carbon double bond, and is exemplified by an alkenyl group or unsaturated fatty acid ester group. The above-described —$R^1$ is introduced by component (c), the above-described -$L^1$ is introduced by component (d), and the above-described —$R^2$ is introduced by component (e).

The (a) polyhydric alcohol derivative having one reactive unsaturated group per molecule is a modifier of the organopolysiloxane, and could be the hydrophilic impurities in the present invention.

More specifically, the polyhydric alcohol derivative-modified silicone can be obtained as below, for example.

The polyhydric alcohol derivative-modified silicone can be obtained by addition reacting with organopolysiloxane having a silicon-hydrogen bond, an unsaturated organic compound having a carbon-carbon double bond at one terminal of the molecular chain, and an unsaturated ether compound of a polyhydric alcohol derivative having a carbon-carbon double bond in the molecule. Noted that, a siloxane dendron compound having a carbon-carbon double bond at one terminal of the molecular chain, and/or an unsaturated long chain hydrocarbon compound having a carbon-carbon double bond at one terminal of the molecular chain, or a chain organopolysiloxane having a carbon-carbon double bond at one terminal of the molecular chain can be further addition reacted.

In the above case, the polyhydric alcohol derivative-modified silicone can be obtained as the product of a hydrosilylation reaction between the unsaturated organic compound and the polyhydric alcohol derivative unsaturated ether compound, and optionally the siloxane dendron compound and/or an unsaturated long chain hydrocarbon compound, or a chain organopolysiloxane having a carbon-carbon double bond at one terminal of the molecular chain; and a SiH group-containing organopolysiloxane. This enables the introduction of an organic group and a polyhydric alcohol derivative group, and optionally a silylalkyl group having a siloxane dendron structure and/or a long chain hydrocarbon group or a chain organopolysiloxane group into the polysiloxane chain. This reaction can be performed as a batch or can take the form of successive reactions. However, successive reactions are preferable from the perspectives of safety and quality control.

For example, the polyhydric alcohol derivative-modified silicone can be obtained by at least reacting, in the presence of a hydrosilylation reaction catalyst, the (b1) organohydrogenpolysiloxane represented by the following general formula (1'):

[Chemical Formula 38]

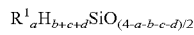
(1')

(wherein, $R^1$, a, b, c and d are synonymous with those described above) and (a) a polyhydric alcohol derivative having one reactive unsaturated group per molecule. It is preferable to further react (d) a siloxane dendron compound having one reactive unsaturated group per molecule, and/or (e) a hydrocarbon compound having one reactive unsaturated group per molecule, or chain organopolysiloxane having one reactive unsaturated group per molecule.

The polyhydric alcohol derivative-modified silicone can be preferably produced, in the state where (a) a polyhydric alcohol derivative having one reactive unsaturated group per molecule, and optionally (d) a siloxane dendron compound having one reactive unsaturated group per molecule, and/or (e) a hydrocarbon compound having one reactive unsaturated group per molecule or a chain organopolysiloxane having one reactive unsaturated group per molecule coexist, by reacting together the component (a), the component (d) and/or the component (e), as well as the (b1) organohydrogenpolysiloxane, or by successively addition reacting the (b1) organohydrogenpolysiloxane and optionally the component (d), and/or the component (e), and further addition reacting the component (a).

The (b) organopolysiloxane having silicon atom bonded hydrogen atoms, which is used in the synthesis of the polyhydric alcohol derivative-modified silicone is preferably, for example, an (b2) organohydrogenpolysiloxane represented by the following structural formula (1-1)':

[Chemical Formula 39]

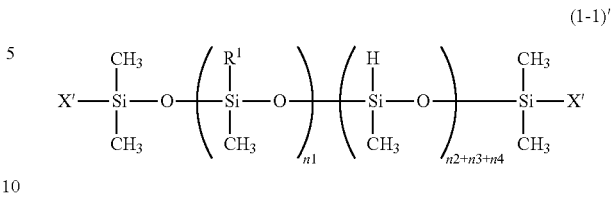
(1-1)'

(wherein,
$R^1$ are each independently synonymous with those described above,
X' is a group selected from $R^1$ or a hydrogen atom, and
n1, n2, n3, and n4 are synonymous with those described above. However, when n2+n3+n4=0, at least one X' is a hydrogen atom).

The polyhydric alcohol derivative-modified silicone is preferably synthesized by subjecting to a hydrosilylation reaction of (a) a polyhydric alcohol derivative having a carbon-carbon double bond at a terminal of the molecular chain and (b2) an organohydrogenpolysiloxane; and the organohydrogensiloxane (component (b2)) is preferably an organohydrogensiloxane obtained by successively addition reacting the component (d) and/or the component (e). In this case, the organohydrogensiloxane immediately prior to reaction with component (a) (after successive reactions with other components) is preferably represented by the following structural formula (1-1A):

[Chemical Formula 40]

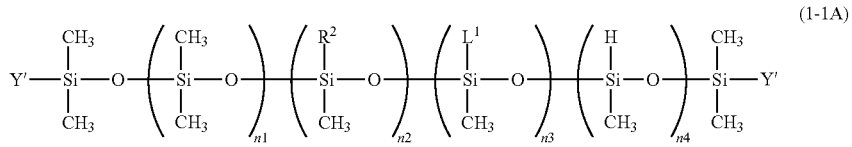
(1-1A)

(wherein,
$R^2$ and $L^1$ are each independently synonymous with those described above,
Y' is a group selected from the group consisting of a methyl group, $R^2$, $L^1$, and a hydrogen atom (H),
n1, n2, n3, and n4 are each independently a number in a range of 0 to 2,000, and n1+n2+n3+n4 is a number in a range of 0 to 2,000. However, when n4=0, at least one Y' is a hydrogen atom.).

The polyhydric alcohol derivative having one reactive unsaturated group per molecule, which is used in the synthesis of the polyhydric alcohol derivative-modified silicone, is preferably (a1) a polyhydric alcohol derivative having a carbon-carbon double bond at the terminal of the molecular chain, and more preferably a glycerin derivative having a carbon-carbon double bond at the terminal of the molecular chain. This is a (poly)glycerin derivative having an allyl(poly)glycerin, allyl polyglycidyl ether, (poly)glycerin monoallyl ether, or similar reactive functional group having an alkenyl group or the like at the molecular chain terminal, and can be synthesized according to a publicly known method.

The (a) polyhydric alcohol derivative having one reactive unsaturated group per molecule, for example, the (a1) polyhydric alcohol derivative having a carbon-carbon double bond at the terminal of the molecular chain is a modifier of the organopolysiloxane, and could be the hydrophilic impurities in the present invention.

In the polyhydric alcohol derivative-modified silicone according to the present invention, from the perspectives of thickening effect and gel formability with respect to an oil agent, use as a surfactant (emulsifier), and various treatment agents (powder dispersing agents or surface treatment agents), specifically, component (a) is preferably a (poly) glycerin compounds having a monoglycerin, a diglycerin, a triglycerin, or a tetraglycerin structure such as a (poly) glycerin monoallyl ether and a (poly)glyceryl eugenol.

Such a component (a) can be exemplified by a glycerin derivative having a carbon-carbon double bond at the terminals of the molecular chain expressed by the following structural formulae (4-8') through (4-11'). $X^1$, $X^2$, and $R^{10}$ in the formulae are groups synonymous with the groups described above, and m and q are numbers synonymous with the numbers described above. R' is an unsaturated organic group having a carbon-carbon double bond at the terminal, and is preferably a substituted or unsubstituted, straight or branched unsaturated hydrocarbon group having from 3 to 5 carbons. Examples of the unsaturated hydrocarbon group having from 3 to 5 carbons include alkenyl groups such as allyl groups, butenyl groups, and methallyl groups; and the unsaturated hydrocarbon group is preferably an allyl group.

[Chemical Formula 41]

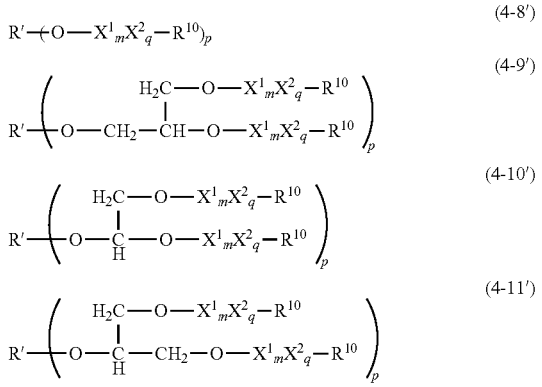

The (d) siloxane dendron compound having one reactive unsaturated group per molecule, which is used in the synthesis of a glycerin derivative-modified silicone according to the present invention, is preferably a compound having a siloxane dendron structure with one carbon-carbon double bond at a molecular chain terminal, and is represented by the following general formula (3'):

[Chemical Formula 42]

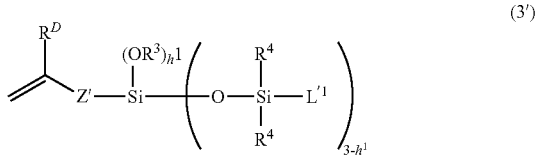

(wherein,
$R^3$ and $R^4$ are synonymous with those described above,
$R^D$ is a hydrogen atom or a methyl group;
Z' represents a divalent organic group same as Z;
$h^1$ is a number in a range of 0 to 3;

$L'^1$ represents $R^4$ moiety or, when j=1, a silylalkyl group represented by the following general formula (3"):

[Chemical Formula 43]

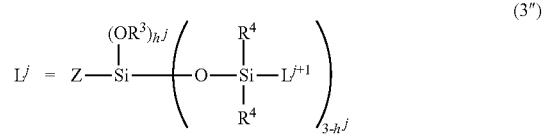

(wherein, $R^3$ and $R^4$ are synonymous with those described above;

Z represents a divalent organic group;

j represents the generations of the silylalkyl group expressed by $L^j$, when the number of generations (the number of repetitions) of the silylalkyl group is k', j is an integer of 1 to k', and the number of generations k' is an integer from 1 to 9; $L^{j+1}$ is the silylalkyl group when j is less than k' and is the $R^4$ moiety when j=k'; and $h^j$ is a number in a range of 0 to 3).

The (e) hydrocarbon compound having one reactive unsaturated group per molecule or chain organopolysiloxane having one reactive unsaturated group per molecule, which is used in the synthesis of a polyhydric alcohol derivative-modified silicone according to the present invention, is preferably a mono unsaturated organic compound represented by the following general formula (2'):

[Chemical Formula 44]

(wherein, R' represents an unsaturated organic group;

$R^{2'}$ represents a substituted or unsubstituted, straight or branched monovalent hydrocarbon group having from 7 to 58 carbons) or the following general formula (2'-1):

[Chemcial Formula 45]

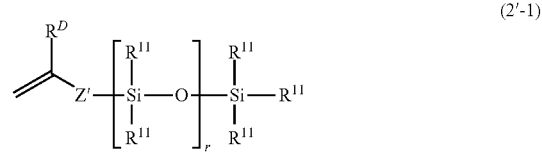

(wherein, $R^D$, Z', $R^{11}$, and r are synonymous with those described above).

The (e) hydrocarbon compound having one reactive unsaturated group per molecule is preferably a mono unsaturated hydrocarbon having from 9 to 30 carbons and is more preferably a 1-alkene. Examples of the 1-alkene include 1-nonene, 1-decene, 1-undecene, 1-dodecene, 1-tridecene, 1-tetradecene, 1-hexadecene, 1-octadecene and the like. Examples of the chain organopolysiloxane having one reactive unsaturated group per molecule include a dimethylpolysiloxane capped at one molecular terminal with a vinyl group, a methylphenylpolysiloxane capped at one molecular terminal with a vinyl group, and the like.

The hydrosilylation reaction used to synthesize the polyhydric alcohol derivative-modified silicone or the composition containing the same can be carried out in accordance with a publicly known method in the presence or absence of a solvent. Here, examples of the reaction solvent include alcohol-based solvents such as ethanol and isopropyl alcohol; aromatic hydrocarbon-based solvents such as toluene and xylene; ether-based solvents such as dioxane and THF; aliphatic hydrocarbon-based solvents such as n-hexane, cyclohexane, n-heptane, cycloheptane, and methylcyclohexane; chlorinated hydrocarbon-based organic solvents such as carbon tetrachloride; and various oil agents (such as silicone oil, hydrocarbon oil, ester, oil, etc.) that can also be used as the oil agents described later.

The hydrosilylation reaction may be performed in the absence of a catalyst, but preferably is performed in the presence of a catalyst because the reaction can be carried out at a low temperature and in a shorter period of time. Examples of the catalyst include compounds such as platinum, ruthenium, rhodium, palladium, osmium, iridium, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, or the like; and a platinum complex such as platinum-vinylsiloxane complex, platinum-phosphine complex, platinum-phosphite complex, platinum alcoholate catalyst, or the like. When a platinum catalyst is used, the usage quantity of the catalyst is, as platinum metal, approximately 0.0001 to 0.1 mass %, and preferably 0.0005 to 0.05 mass %, but is not limited thereto.

A reaction temperature of the hydrosilylation reaction is typically from 30 to 120° C., and a reaction time is typically from 10 minutes to 24 hours and preferably from 1 to 10 hours.

When the hydrosilylation reaction is performed, the ratio [amount of substance of carbon-carbon double bonds in polyhydric alcohol derivative group-containing compound/amount of substance of silicon-bonded hydrogen atoms to be added to the carbon-carbon double bonds of the polyhydric alcohol derivative group-containing compound in the organohydrogenpolysiloxane] is preferably in a range of 0.8 to 1.5, and more preferably in a range of 1.0 to 1.3. That is, when synthesizing the polyhydric alcohol derivative-modified silicone or a composition containing the same according to the present invention, it is more preferable to use a slight excess of the polyhydric alcohol derivative group-containing compound. Although processing in which the above-described ratio is greater than 1.5 is also possible, the proportion of residual starting material increases, so it is not economical. Noted that, during the hydrosilylation reaction, the terminal carbon-carbon double bonds in the polyhydric alcohol derivative group-containing compound transition internally so that a deactivating side-reaction occurs simultaneously. Therefore, when the ratio described above is from 0.8 to 1.0, the silicon-bonded hydrogen atoms consumed by the hydrosilylation reaction settle to within a slightly lower range than the range of theoretical values from 0.8 to 1.0, consequently silicon-bonded hydrogen atoms remain at a slightly greater ratio than 0 to 0.2. However, it is also possible to cause dehydrogenation reactions with hydroxyl groups contained in the polyhydric alcohol derivative group and alcoholic hydroxyl groups of the reaction solvent, which can consume the remaining silicon-bonded hydrogen atoms, depending on the reaction conditions.

On the other hand, when the above-described ratio is less than 0.8, there is a risk that unreacted organohydrogenpolysiloxane will remain. When such a polyhydric alcohol derivative-modified silicone or a composition containing the same is used as the raw material for an external use preparation or a cosmetic composition, remaining organohydrogenpolysiloxane might react with the other raw materials, and generate hydrogen gas. This might cause undesirable effects such as alteration of the external use preparation or the cosmetic composition at the incorporation destination, fire, container expansion, and the like. In addition, when an attempt is made to consume the remaining silicon-bonded hydrogen atoms by using a dehydrogenation reaction when the above-described ratio is less than 0.8, the proportion of Si—O—C crosslinked bonds increases, which increases the tendency to cause gelation during production. Therefore, to enable the complete and safe consumption of organohydrogenpolysiloxane, it is preferable that the above-described ratio exceeds 0.8, i.e., that 0.8 equivalent weight or more of the polyhydric alcohol derivative group-containing compound is reacted.

Moreover, the polyhydric alcohol derivative-modified silicone to which the present invention is applicable can be a liquid polyhydric alcohol derivative-modified crosslinked silicone. The liquid polyhydric alcohol derivative-modified silicone is preferably an organo-modified silicone having a silicon-bonded polyhydric alcohol derivative group and having a crosslinked structure including a Si—C bond in a crosslinking part, which is obtained by reacting (A) an organohydrogenpolysiloxane, (B) a polyhydric alcohol derivative group-containing organic compound having at least one reactive unsaturated group per molecule, as well as (C) at least one organic compound selected from a group consisting of (C1) an organic compound having the number of reactive unsaturated groups greater than 1 on average per molecule and (C2) an organic compound having at least one reactive unsaturated group and at least one epoxy group per molecule (however, the use of the component (B) is optional when the component (C) contains a polyhydric alcohol derivative group).

The (A) organohydrogenpolysiloxane is not particularly limited as long as it has silicon atom bonded hydrogen atoms, but preferably have on average more than one (preferably from 1.01 to 100, more preferably from 1.1 to 50, even more preferably from 1.2 to 25, and particularly preferably from 1.3 to 10) silicon atom bonded hydrogen atoms per molecule, and a straight-chain, branched, or reticulated organopolysiloxane may be used. The positions of the silicon atom bonded hydrogen atoms in the organohydrogenpolysiloxane is not limited, and can be on the main chain or at the terminals. However, from the viewpoint of reducing the degree of crosslinking, the silicon atom bonded hydrogen atoms are preferably positioned at the terminals. As for the component (A), one or at least two organohydrogenpolysiloxanes may be used.

Examples of the component (A) include 1,1,3,3-tetramethyldisiloxane, 1,3,5,7-tetramethylcyclotetrasiloxane, methylhydrogenpolysiloxane capped at both terminals with trimethylsiloxy groups, dimethylsiloxane-methylhydrogensiloxane copolymers capped at both terminals with trimethylsiloxy groups, dimethylsiloxane capped at both terminals with dimethylhydrogensiloxy groups, dimethylpolysiloxane capped at both terminals with dimethylhydrogensiloxy groups, dimethylsiloxane-methylhydrogensiloxane copolymers capped at both terminals with dimethylhydrogensiloxy groups, methylhydrogensiloxane-diphenylsiloxane copolymers capped at both terminals with trimethylsiloxy groups, methylhydrogensiloxane-diphenylsiloxane-dimethylsiloxane copolymers capped at both terminals with trimethylsiloxy groups, copolymers comprising $(CH_3)_2HSiO_{1/2}$ units and $SiO_{4/2}$ units, and copolymers comprising $(CH_3)_2HSiO_{1/2}$ units, $SiO_{4/2}$ units, and $(C_6H_5)SiO_{3/2}$ units.

The component (A) is preferably represented by the average composition formula (11):

$$R^1{}_a H_b SiO_{(4-a-b)/2} \quad (11)$$

(in the average composition formula (11), $R^1$ moieties are each independently a monovalent organic group; $1.0 \leq a \leq 3.0$, and $0.001 \leq b \leq 1.5$).

The molecular structure of the (A) organohydrogenpolysiloxane is not limited, examples thereof include straight-chain, partially branching straight-chain, branched-chain, cyclic, and dendritic structures, and straight-chain is preferable. Also, the molecular weight is not particularly limited, and products having a low molecular weight to products having a high molecular weight can be used. Specifically, the number-average molecular weight is preferably in a range of 100 to 1,000,000 and more preferably in a range of 300 to 500,000.

Examples of such organohydrogenpolysiloxanes include those represented by the following structural formulae:

$$R^1{}_3SiO(R^1{}_2SiO)_v(R^1SiHO)_wSiR^1{}_3 \quad (i)$$

$$HR^1{}_2SiO(R^1{}_2SiO)_v(R^1SiHO)_zSiR^1{}_3 \quad (ii)$$

$$HR^1{}_2SiO(R^1{}_2SiO)_v(R^1SiHO)_zSiR^1{}_2H \quad (iii)$$

(in the structural formulae (i) to (iii), $R^1$ is synonymous with that described above; v is 0 or a positive integer; w is a positive integer; and z is 0 or a positive integer). These organohydrogenpolysiloxanes are straight-chain organohydrogenpolysiloxanes having a silicon atom bonded hydrogen atom on (i) only the side chain, (ii) the side chain or one terminal of the molecular chain, or (iii) the side chain or both terminals of the molecular chain.

The monovalent organic group is not particularly limited but is preferably selected from the following (D1) to (D10):

(D1) a substituted or unsubstituted, straight-chain or branched monovalent hydrocarbon group having from 1 to 60 carbons;

(D2) a polyoxyalkylene group expressed by $-R^{28}O(AO)_{z1}R^{29}$ (wherein, AO represents an oxyalkylene group having from 2 to 4 carbons; $R^{28}$ represents a substituted or unsubstituted, straight-chain or branched divalent hydrocarbon group having from 3 to 5 carbons; $R^{29}$ represents a hydrogen atom, a substituted or unsubstituted, straight-chain or branched monovalent hydrocarbon group having from 1 to 24 carbons, or a substituted or unsubstituted, straight-chain or branched acyl group having from 2 to 24 carbons; and z1=1 to 100);

(D3) a substituted or unsubstituted, straight-chain or branched alkoxy group having from 1 to 30 carbons;

(D4) a hydroxyl group;

(D5) an ester group expressed by $-R^{30}-COOR^{31}$ (wherein, $R^{30}$ represents a substituted or unsubstituted, straight-chain or branched divalent hydrocarbon group having from 2 to 20 carbons, and $R^{31}$ represents a substituted or unsubstituted, straight-chain or branched monovalent hydrocarbon group having from 1 to 30 carbons);

(D6) an ester group expressed by $-R^{17}-OCOR^{18}$ (wherein, $R^{17}$ represents a substituted or unsubstituted, straight-chain or branched divalent hydrocarbon group having from 2 to 20 carbons, and $R^{18}$ represents a substituted or unsubstituted, straight-chain or branched monovalent hydrocarbon group having from 1 to 30 carbons);

(D7) $L^1$ here, $L^1$ is a silylalkyl group having a siloxane dendron structure and, when i=1, is expressed by the following general formula (33):

[Chemical Formula 46]

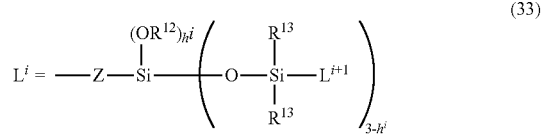

(33)

(in the general formula (33), $R^{12}$ represents a substituted or unsubstituted, straight-chain or branched monovalent hydrocarbon group having from 1 to 30 carbons; $R^{13}$ moieties each independently represent an alkyl group or phenyl group having from 1 to 6 carbons; Z represents a divalent organic group; i represents a generation of a silylalkyl group represented by $L^i$ and is an integer of 1 to k when k is the number of generations that is the number of repetitions of the silylalkyl group; the number of generations k is an integer from 1 to 10; $L^{i+1}$ is the silylalkyl group when i is less than k, and $R^{13}$ when i=k; and $h^i$ is a number in a range of 0 to 3);

(D8) an alkyl group substituted by a chain polysiloxane structure expressed by the following general formula (44):

[Chemical Formula 47]

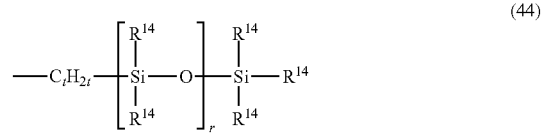

(44)

(in the general formula (44), $R^{14}$ moieties are each independently a substituted or unsubstituted, straight-chain or branched monovalent hydrocarbon group having from 1 to 30 carbons, a hydroxyl group, or a hydrogen atom, and at least one of the $R^{14}$ moieties is the monovalent hydrocarbon group; t is a number in a range of 2 to 10; and r is a number in a range of 1 to 500);

(D9) an epoxy group expressed by the following general formula (55):

[Chemical Formula 48]

(55)

(in the general formula (55), $R^{15}$ is a substituted or unsubstituted, straight-chain or branched divalent hydrocarbon group having from 2 to 20 carbons); and (D10) an alicyclic epoxy group expressed by the following general formula (66):

[Chemical Formula 49]

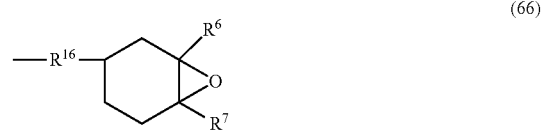

(66)

(in the general formula (66), $R^{16}$ represents a substituted or unsubstituted, straight-chain or branched divalent hydrocarbon group having from 2 to 20 carbons; and $R^6$ and $R^7$ are hydrogen atoms or methyl groups).

Examples of the substituted or unsubstituted, straight-chain or branched monovalent hydrocarbon group in (D1), (D2), and (D5) to (D8) include alkyl groups such as methyl groups, ethyl groups, propyl groups, butyl groups, pentyl groups, hexyl groups, heptyl groups, and octyl groups; cycloalkyl groups such as cyclopentyl groups and cyclohexyl groups; alkenyl groups such as vinyl groups, allyl groups, and butenyl groups; aryl groups such as phenyl groups and tolyl groups; aralkyl groups such as benzyl groups; and groups in which the hydrogen atoms bonded to the carbon atoms of these groups are substituted at least partially by halogen atoms such as fluorine atoms or organic groups such as epoxy groups, glycidyl groups, acyl groups, carboxyl groups, amino groups, methacryl groups, and mercapto groups. The monovalent hydrocarbon group is preferably a group other than an alkenyl group, and is particularly preferably a methyl group, an ethyl group, or a phenyl group.

The substituted or unsubstituted, straight-chain or branched divalent hydrocarbon groups in (D2), (D5), (D6), (D9), and (D10) are as described earlier.

Examples of the substituted or unsubstituted, straight-chain or branched alkoxy group in (D3) include lower alkoxy groups such as methoxy groups, ethoxy groups, isopropoxy groups, and butoxy groups and higher alkoxy groups such as lauryl alkoxy groups, myristyl alkoxy groups, palmityl alkoxy groups, oleyl alkoxy groups, stearyl alkoxy groups, and behenyl alkoxy groups.

Among the phenyl group or the alkyl group having from 1 to 6 carbons in (D7), examples of the alkyl group having from 1 to 6 carbons include straight-chain, branched, or cyclic alkyl groups such as methyl, ethyl, n-propyl, i-propyl, n-butyl, i-butyl, s-butyl, pentyl, neopentyl, cyclopentyl, and hexyl groups.

In the general formula (33), when i=k, $R^{13}$ is preferably a methyl group or a phenyl group. In particular, $R^{13}$ is preferably a methyl group when i=k.

From an industrial standpoint, the number of generations k is preferably an integer of 1 to 3, and more preferably is 1 or 2. In each of the number of generations, the group represented by $L^1$ is represented as follows. In the formulae, $R^{12}$, $R^{13}$, and Z are the same groups as described above.

When the number of generations is k=1, $L^1$ is represented by the following general formula (33-1).

[Chemical Formula 50]

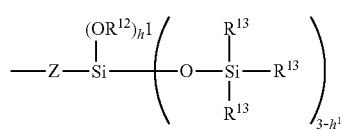

(3-1)

When the number of generations is k=2, $L^1$ is represented by the following general formula (33-2).

[Chemical Formula 51]

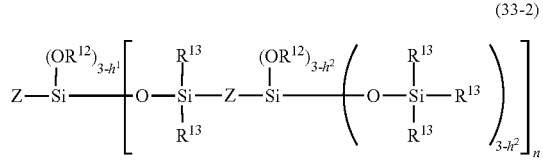

(33-2)

When the number of generations is k=3, $L^1$ is represented by the following general formula (33-3).

[Chemical Formula 52]

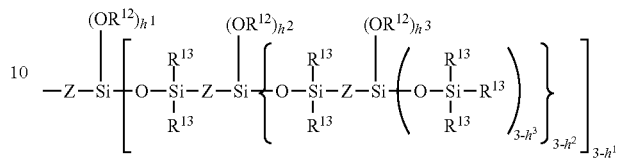

(33-3)

In the structures expressed by the general formulae (33-1) to (33-3) when the number of generations is from 1 to 3, each of $h^1$, $h^2$ and $h^3$ moieties is independently a number in a range of 0 to 3. These $h^i$ moieties are, in particular, preferably a number in a range of 0 to 1, and $h^i$ moieties are particularly preferably 0.

In the general formulae (33) and (33-1) to (33-3), Z are each independently a divalent organic group, and specific examples thereof include a divalent organic group formed by addition reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not limited to the functional groups described above. Preferably, Z are each independently a group selected from divalent organic groups represented by the following general formula:

—$R^{19}$—

—$R^{19}$—CO—

—$R^{19}$—COO—$R^{20}$—

—CO—$R^{19}$—

—$R^{19}$—COO—$R^{20}$—

—$R^{19}$—CONH—$R^{20}$—

—$R^{19}$—$R^{20}$—                    [Chemical Formula 53]

Of these, Z in $L^1$ is preferably a divalent organic group expressed by general formula —$R^{19}$— that is introduced by a reaction between a silicon-bonded hydrogen atom and an alkenyl group. Likewise, Z is preferably a divalent organic group expressed by general formula —$R^{19}$—COO—$R^{20}$— that is introduced by a reaction between a silicon-bonded hydrogen atom and an unsaturated carboxylic ester group. On the other hand, in the silylalkyl group represented by $L^i$, in which the number of generations k is at least 2, and $L^i$ is $L^2$ to $L^k$, Z is preferably an alkylene group having from 2 to 10 carbons, and in particular, is preferably a group selected from an ethylene group, a propylene group, a methylethylene group or a hexylene group, and most preferably is an ethylene group.

In the above-described general formula, $R^{19}$ moieties each independently represent a substituted or unsubstituted, straight-chain or branched-chain alkylene group or alkenylene group having from 2 to 22 carbons or an arylene group having from 6 to 22 carbons. More specifically, examples of $R^{19}$ include straight-chain alkylene groups such as an ethylene group, a propylene group, a butylene group, and a hexylene group; and branched alkylene groups such as a methylmethylene group, a methylethylene group, a 1-methylpentylene group, and a 1,4-dimethylbutylene group. $R^{20}$ is preferably a group selected from an ethylene group, a propylene group, a methylethylene group, and a hexylene group.

In the above-described general formula, $R^{20}$ is preferably a group selected from divalent organic groups expressed by the following formula.

[Chemical Formula 54]

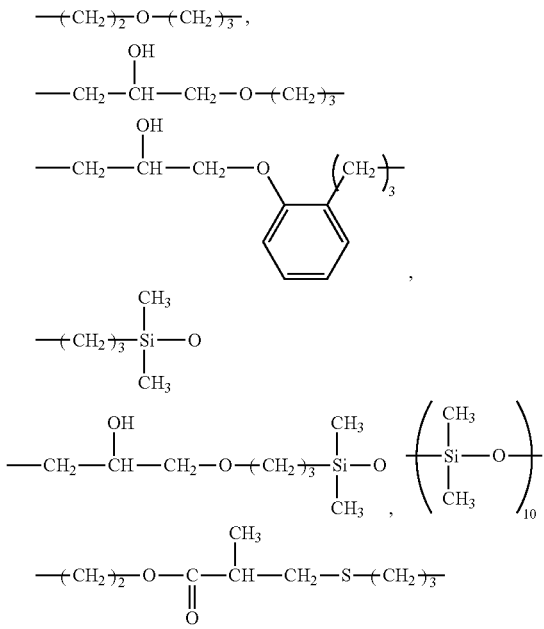

The (B) polyhydric alcohol derivative group-containing organic compound having a reactive unsaturated group is not particularly limited as long as it has at least one of each of the reactive unsaturated group and the polyhydric alcohol derivative group per molecule, but a polyhydric alcohol derivative having a carbon-carbon double bond at the terminal of the molecular chain is preferable, and a glycerin derivative having a carbon-carbon double bond at the terminal of the molecular chain is more preferable, and a mono-, di-, tri-, or tetra-glycerin derivative having a carbon-carbon double bond at the terminal of the molecular chain is even more preferable. These are glycerin derivatives having reactive functional groups such as alkenyl groups at the terminals of the molecular chains of allyl monoglycerols (monoglycerin monoallyl ether), allyl diglycerols (diglycerin monoallyl ether), triglycerin monoallyl ethers, triglycerin diallyl ethers, tetraglycerin monoallyl ethers, or the like, and can be synthesized by a publicly known method.

The (B) polyhydric alcohol derivative group-containing organic compound having a reactive unsaturated group could be the hydrophilic impurities in the present invention.

There are no particular limitations regarding the structure of the (C1) organic compound having the number of unsaturated bonds greater than 1 on average per molecule that is serving as the component (C), as long as the compound has on average more than 1 (preferably from 1.01 to 10, more preferably from 1.2 to 8, even more preferably from 1.5 to 6, and particularly preferably from 2.0 to 4.5) unsaturated bonds and preferably carbon-carbon double bonds per molecule, straight-chain, branched, or reticulated organic compounds may be used. An organopolysiloxane or an unsaturated aliphatic hydrocarbon is preferable as an organic compound. The position of the unsaturated bonds on the organic compound is not limited and preferably the organopolysiloxane or the unsaturated aliphatic hydrocarbon, and the component may be positioned on the main chain or on a terminal. However, from the perspective of the ease of controlling the crosslinking density, it is preferable to use a compound of high purity having two unsaturated groups in one molecule, each of which is positioned at either terminal, for example.

An unsaturated bond is preferably present in an unsaturated aliphatic hydrocarbon group. The unsaturated aliphatic hydrocarbon group preferably has from 2 to 30 carbons and more preferably has from 2 to 20 carbons. Examples of the monovalent unsaturated aliphatic hydrocarbon group having from 2 to 30 carbons include straight-chain or branched alkenyl groups such as vinyl groups, 1-propenyl groups, allyl groups, isopropenyl groups, 1-butenyl, 2-butenyl groups, pentenyl groups, and hexenyl groups; cycloalkenyl groups such as cyclopentenyl groups and cyclohexenyl groups; cycloalkenylalkyl groups such as cyclopentenylethyl groups, cyclohexenylethyl groups, and cyclohexenylpropyl groups; and alkynyl groups such as ethynyl groups and propargyl groups. Alkenyl groups are preferred, and the vinyl groups and hexenyl groups are particularly preferred.

When the component (C1) is an organopolysiloxane, the unsaturated aliphatic hydrocarbon group containing an unsaturated bond is preferably bonded to a silicon atom. In addition, when the component (C1) is an organopolysiloxane, the group bonding to silicon atoms other than the unsaturated aliphatic hydrocarbon may be a substituted or unsubstituted monovalent hydrocarbon group or a monovalent organic group having a reactive functional group.

Substituted or unsubstituted monovalent hydrocarbon groups are typically substituted or unsubstituted, straight-chain or branched monovalent saturated hydrocarbon groups having from 1 to 30 carbons, preferably from 1 to 10 carbons, and more preferably from 1 to 4 carbons; and substituted or unsubstituted, straight-chain or branched monovalent aromatic hydrocarbon groups having from 6 to 30 carbons, and more preferably from 6 to 12 carbons. Noted that, the component (C1) may have, as a monovalent organic group, a hydroxyl group or an alkoxy group having from 1 to 12 carbons such as a methoxy group, an ethoxy group, a propoxy group and a butoxy group.

Examples of the monovalent saturated hydrocarbon group having from 1 to 30 carbons include straight-chain or branched alkyl groups such as methyl groups, ethyl groups, n-propyl groups, isopropyl groups, n-butyl groups, isobutyl groups, sec-butyl groups, tert-butyl groups, pentyl groups, hexyl groups, heptyl groups, octyl groups, nonyl groups, decyl groups, and the like; and cycloalkyl groups such as cyclopentyl groups, cyclohexyl groups, cycloheptyl groups, cyclooctyl groups, and the like.

Examples of the monovalent aromatic hydrocarbon group having from 6 to 30 carbons include aryl groups such as phenyl groups, tolyl groups, xylyl groups, mesityl groups, and the like. Of these, the phenyl group is preferable. Note that, in the present specification, "aromatic hydrocarbon group" also includes groups in which an aromatic hydrocarbon and a saturated aliphatic hydrocarbon are conjugated in addition to groups formed only from an aromatic hydrocarbon. Examples of groups in which an aromatic hydrocarbon and a saturated hydrocarbon are conjugated include aralkyl groups such as benzyl groups, phenethyl groups, and the like.

Hydrogen atoms in the above-described monovalent hydrocarbon groups may be substituted by at least one substituted groups, and the substituted groups is selected from the group consisting of, for example, a halogen atom (a fluorine atom, a chlorine atom, a bromine atom, or an iodine atom), a hydroxyl group, an amide group, an ester group, a carboxyl group and an isocyanate group. A monovalent saturated or aromatic hydrocarbon group having at least one of the above-described substituted groups is preferred. Specifically, it is possible to use a 3,3,3-trifluoropropyl group, a 3-chloropropyl group, a 3-hydroxypropyl group, a 3-(2-hydroxyethoxy)propyl group, a 3-carboxypropyl group, a 10-carboxydecyl group, a 3-isocyanatopropyl group and the like.

Examples of monovalent organic groups having reactive functional groups include monovalent saturated or aromatic hydrocarbon groups having reactive functional groups selected from the group consisting of, for example, hydroxyl groups, mercapto groups, epoxy groups, amino groups, amide groups, ester groups, carboxyl groups and isocyanate groups. One or a plurality of reactive functional groups may exist in the monovalent organic group. A preferable $R^1$ is a monovalent saturated or aromatic hydrocarbon group having at least one of the above-described reactive functional groups. Specific examples of the reactive functional group include 3-hydroxypropyl groups, 3-(2-hydroxyethoxy)propyl groups, 3-mercaptopropyl groups, 2,3-epoxypropyl groups, 3,4-epoxybutyl groups, 4,5-epoxypentyl groups, 2-glycidoxyethyl groups, 3-glycidoxypropyl groups, 4-glycidoxybutyl groups, 2-(3,4-epoxycyclohexyl) ethyl groups, 3-(3,4-epoxycyclohexyl)propyl groups, aminopropyl groups, N-methylaminopropyl groups, N-butylaminopropyl groups, N,N-dibutylaminopropyl groups, 3-(2-aminoethoxy)propyl groups, 3-(2-aminoethylamino)propyl groups, 3-carboxypropyl groups, 10-carboxydecyl groups, 3-isocyanate propyl groups, and the like.

A straight-chain, cyclic, or branched polysiloxane is preferable as the component (C1). A straight-chain component (C1) is preferably a polymer including a diorganosiloxane unit and a triorganosiloxane unit, examples of which include dimethylpolysiloxanes capped at both molecular chain terminals with dimethylvinylsiloxy groups, copolymers of dimethylsiloxane and methylphenylsiloxane capped at both molecular chain terminals with dimethylvinylsiloxy groups, copolymers of dimethylsiloxane and methylvinylsiloxane capped at both molecular chain terminals with dimethylvinylsiloxy groups, copolymers of dimethylsiloxane and methylvinylsiloxane capped at both molecular chain terminals with trimethylsiloxy groups, copolymers of dimethylsiloxane, methylvinylsiloxane and methylphenylsiloxane capped at both molecular chain terminals with trimethylsiloxy groups, copolymers of dimethylsiloxane and methylvinylsiloxane capped at both molecular chain terminals with silanol groups, polymers in which some of the methyl groups in these polymers are substituted by alkyl groups other than methyl groups such as ethyl groups or propyl groups, or halogenated alkyl groups such as 3,3,3-trifluoropropyl groups, and mixtures of at least two of these polymers. In particular, a straight-chain diorganopolysiloxane having unsaturated aliphatic hydrocarbon groups, especially alkenyl groups, only at both molecular chain terminals is preferable.

As for the branched chain component (C1), a polymer containing a diorganosiloxane unit, an organosilsesquioxane unit and a triorganosiloxy unit is particularly preferable. Silicon atom bonded organic groups in these units are preferably monovalent hydrocarbon groups including alkyl groups such as methyl groups, ethyl groups and propyl groups; alkenyl groups such as vinyl groups, allyl groups, butenyl groups and hexenyl groups; aryl groups such as phenyl groups and tolyl groups; and halogenated alkyl groups such as 3,3,3-trifluoropropyl groups, and may contain extremely small quantities of hydroxyl groups and alkoxy groups such as methoxy groups, but at least two silicon atom bonded organic groups in this polymer must be unsaturated aliphatic hydrocarbon groups, especially alkenyl groups. In addition, the proportions of these units are not limited, but in this polymer, it is preferable for diorganosiloxane units to be in an amount in the range of 80.00 to 99.65 mol % and organosilsesquioxane units to be in an amount in the range of 0.10 to 10.00 mol %, with the balance comprising triorganosiloxy units.

Examples of the component (C1) that is a cyclic polysiloxane include methylvinylcyclosiloxane, methylhexenylcyclosiloxane, and the like.

Examples of the component (C1) include (C1-5) unsaturated group-containing silicone compounds expressed by the average composition formula (22):

$$R^{32}{}_{p}R^{33}{}_{q}SiO_{(4-p-q)/2} \tag{22}$$

(In the formula (22), $R^{32}$ may be independent to each other and represents a monovalent organic group different from $R^{33}$; $R^{33}$ each independently represent monovalent unsaturated aliphatic hydrocarbon groups having from 2 to 30 carbons; $1.0 \leq p \leq 2.5$, and $0.001 \leq q \leq 1.5$). The monovalent unsaturated aliphatic hydrocarbon group having from 2 to 30 carbons is as described earlier.

In the average composition formula (22), the monovalent organic group represented by $R^{32}$ is not particularly limited, but is preferably selected from the following (E1) to (E6):

(E1) a substituted or unsubstituted, straight-chain or branched monovalent hydrocarbon group having from 1 to 60 carbons (excluding monovalent hydrocarbon groups having from 2 to 20 carbons and an aliphatic unsaturated group);

(E2) a hydroxyl group;

(E3) an ester group expressed by —$R^{30}$—$COOR^{31}$ (wherein, $R^{30}$ and $R^{31}$ are synonymous with those described above);

(E4) an ester group expressed by —$R^{17}$—$OCOR^{18}$ (wherein, $R^{17}$ and $R^{18}$ are synonymous with those described above);

(E5) an amide group expressed by —$R^{21}$—$NR^{22}COR^{23}$ (wherein, $R^{21}$ represents a substituted or unsubstituted, straight-chain or branched divalent hydrocarbon group having from 2 to 20 carbons; $R^{22}$ represents a hydrogen atom, or a substituted or unsubstituted, straight-chain or branched monovalent hydrocarbon group having from 1 to 20 carbons; and $R^{23}$ represents a substituted or unsubstituted, straight-chain or branched monovalent hydrocarbon group having from 1 to 30 carbons); and (E6) an amide group expressed by —$R^{24}$—$CONR^{25}R^{26}$ (wherein, $R^{24}$ represents a substituted or unsubstituted, straight-chain or branched divalent hydrocarbon group having from 2 to 20 carbons; and $R^{25}$ and $R^{26}$ are each independently represent a hydrogen atom or a substituted or unsubstituted, straight-chain or branched monovalent hydrocarbon group having from 1 to 20 carbons). The definitions, types, and the like of the substituted or unsubstituted, straight-chain or branched monovalent hydrocarbon groups or divalent hydrocarbon groups are as described earlier.

On the other hand, the component (C1) may be an unsaturated aliphatic hydrocarbon. Examples of unsaturated aliphatic hydrocarbons include various dienes, diynes, enynes and similar products having at least two unsaturated bonds. In view of crosslinking, dienes, diynes, and enynes are preferable. Dienes, diynes, and enynes are compounds having a structure in which at least two unsaturated bonds are separated by at least one single bond, and preferably at least two single bonds in a molecule. The unsaturated aliphatic hydrocarbon groups may be present at the terminal of the molecular chain, or as a pendant group in the molecular chain.

Examples of unsaturated aliphatic hydrocarbons serving as the component (C1) include α,ω-unsaturated alkenes and alkynes having from 2 to 30 carbons. Examples of the component (C1) include a (C1-1) α,ω-diene expressed by the general formula (22-1):

$$CH_2=CH(CH_2)_xCH=CH_2 \quad (22\text{-}1)$$

(in the general formula (22-1), $1 \leq x \leq 20$); a (C1-2) α,ω-diyne expressed by the general formula (C22-2):

$$CH\equiv C(CH_2)_xC\equiv CH \quad (22\text{-}2)$$

(in the general formula (C22-2), $1 \leq x \leq 20$); a (C1-3) α,ω-ene-yne expressed by the general formula (22-3):

$$CH_2=CH(CH_2)_xC\equiv CH \quad (22\text{-}3)$$

(in the general formula (22-3), $1 \leq x \leq 20$); a (C1-4) bis alkenyl polyether compound expressed by the general formula (22-4):

$$C_{m'}H_{2m'-1}O(C_{n'}H_{2n'}O)_yC_{m'}H_{2m'-1} \quad (22\text{-}4)$$

(in the general formula (22-4), $2 \leq m' \leq 20$; $2 \leq n' \leq 4$; y is the total value of the number of repetitions of the oxyethylene unit, oxypropylene unit, and oxybutylene unit; $1 \leq y \leq 180$).

Specific examples of unsaturated aliphatic hydrocarbons serving as the component (C1) include 1,4-pentadiene, 1,5-hexadiene, 1,6-heptadiene, 1,7-octadiene, 1,8-nonadiene, 1,9-decadiene, 1,11-dodecadiene, 1,13-tetradecadiene, 1,19-eicosadiene, 1,3-butadiene, 1,5-hexadiyne, and 1-hexene-5-yne.

The component (C1) may be a single component, but may also be a mixture of at least two components having different structures. That is, the component (C1) may be a mixture of at least one organopolysiloxane and at least one unsaturated aliphatic hydrocarbon. Therefore, "having the number of unsaturated bonds greater than 1 on average" here means having more than one unsaturated bonds per molecule on average when at least two organopolysiloxanes and/or unsaturated aliphatic hydrocarbons are used.

The (C2) organic compound having at least one unsaturated bond and at least one epoxy group per molecule serving as the component (C) is not structurally limited as long as the compound has at least two, in total, (preferably from 2 to 10, more preferably from 2 to 7, even more preferably from 2 to 5, and particularly preferably from 2 to 4) unsaturated bonds and epoxy groups per molecule, and straight-chain, branched, or reticulated organic compounds can be used. An organopolysiloxane or an unsaturated aliphatic hydrocarbon is preferable as an organic compound. The position of the unsaturated bonds on the organic compound is not limited, preferably the organopolysiloxane or the unsaturated aliphatic hydrocarbon, and the component may be positioned on the main chain or on a terminal. However, from the perspective of the ease of controlling the crosslinking density, it is preferable to use a compound of high purity in which the total of unsaturated groups and epoxy groups in the molecule is two.

An unsaturated bond is preferably present in an unsaturated aliphatic hydrocarbon group. Examples of unsaturated aliphatic hydrocarbon groups are as described earlier.

When the component (C2) is an organopolysiloxane, the unsaturated aliphatic hydrocarbon group containing an unsaturated bond and/or the epoxy group is preferably bonded to a silicon atom. In addition, when the component (C2) is an organopolysiloxane, the group bonding to silicon atoms other than the unsaturated aliphatic hydrocarbon or the epoxy group may be a substituted or unsubstituted monovalent hydrocarbon group or a monovalent organic group having a reactive functional group, as described earlier.

The component (C2) is preferably an epoxy group-containing unsaturated aliphatic hydrocarbon having at least one epoxy group. Examples of the unsaturated aliphatic hydrocarbon include compounds having the unsaturated aliphatic hydrocarbon groups described earlier. A compound having a monovalent unsaturated aliphatic hydrocarbon group is preferable.

Examples of the component (C2) include a (C2-1) unsaturated epoxy compound expressed by the general formula (22-6):

[Chemical Formula 55]

(22-6)

(in the general formula (22-6), $R^4$ has one unsaturated bond and represents a substituted or unsubstituted, straight-chain or branched monovalent hydrocarbon group having from 2 to 20 carbons); and a (C2-2) unsaturated group-containing alicyclic epoxy compound expressed by the general formula (22-7):

[Chemical Formula 56]

(22-7)

(in the general formula (22-7), $R^5$ has one unsaturated bond and represents a substituted or unsubstituted, straight-chain or branched monovalent hydrocarbon group having from 2 to 20 carbons; $R^6$ represents a hydrogen atom or a methyl group; and $R^7$ represents a hydrogen atom or a methyl group). The definitions, types, and the like of the unsaturated bonds and the substituted or unsubstituted, straight-chain or branched monovalent hydrocarbon groups in the above-described general formulae are as described earlier.

Specific examples of the epoxy group-containing unsaturated aliphatic hydrocarbons serving as the component (C2) include an allylglycidylether, methallylglycidylether, 1-methyl-4-isopropenylcyclohexene oxide, 1,4-dimethylcyclohexene oxide, 4-vinylcyclohexene oxide, vinylnorbornene monooxide, dicyclopentadiene monooxide, butadiene monooxide, 1,2-epoxy-5-hexene, 1,2-epoxy-9-decene, and 2,6-dimethyl-2,3-epoxy-7-octene. Among these, 4-vinyl cyclohexane oxide is preferable. Moreover, the examples of an unsaturated aliphatic hydrocarbons having a cyclic structure include dicyclopentadiene, divinylbenzene, cyclohexadiene, cyclooctadiene, cyclopentadiene, and the like.

The component (C2) may be a single component, but may also be a mixture of at least two components having different structures.

The reaction for producing the polyhydric alcohol derivative-modified crosslinked silicone described above can be performed in accordance with a publicly known method in the presence or absence of a reaction solvent. The reaction between the unsaturated group and the Si—H group is a hydrosilylation reaction. In addition, when crosslinking is performed using an epoxide of (C2) the organic compound having at least one reactive unsaturated group and at least one epoxy group per molecule, bonding caused by the reaction of the unsaturated group and the Si—H group and ether bond generation caused by the self-ring-opening polymerization of the epoxy groups (cationic polymerization reaction that occurs in the presence of a Si—H group and a platinum catalyst) both occur, resulting in crosslinking. In order to accelerate this reaction, irradiation using high energy beams such as ultraviolet light can be applied, or a common cation polymerization catalyst can be further added.

The reaction solvent is not particularly limited as long as the solvent is non-reactive, and examples thereof include alcohol-based solvents such as ethanol and isopropyl alcohol; aromatic hydrocarbon-based solvents such as toluene and xylene; ether-based solvents such as dioxane and THF; aliphatic hydrocarbon-based solvents such as n-hexane, cyclohexane, n-heptane, cycloheptane, and methylcyclohexane; and chlorinated hydrocarbon-based organic solvents such as carbon tetrachloride. An oil agent described below may also be used as a reaction solvent. When an oil agent is used as a reaction solvent, it is possible to directly obtain a composition consisting of an oil agent and a liquid polyhydric alcohol derivative-modified silicone having a silicon atom bonded polyhydric alcohol derivative group and having a crosslinked structure containing a carbon-silicon bond in a crosslinking part after the crosslinking reaction.

The hydrosilylation reaction can be performed as described earlier.

The component (A) is crosslinked by the component (C) as a result of the hydrosilylation reaction or the cationic polymerization reaction of the epoxy groups, and the polysiloxane chains originating from the component (A) are linked by the crosslinking portion having a carbon-silicon bond originating from the component (C). Moreover, the component (A) includes a polyhydric alcohol derivative group originating from the component (B). In this way, it is possible to obtain a polyhydric alcohol derivative-modified crosslinked silicone having a crosslinked structure.

Noted that, the polyhydric alcohol derivative-modified crosslinked silicone having a crosslinked structure essentially has a linked structure formed by the crosslinking part containing a carbon-silicon bond originating from the component (C), but it may also have a portion crosslinked by the Si—O—C bond. This is because when the structure has a condensation-reactable functional group such as a silanol group or an alkoxy group in the components (A) to (C), links can not only be formed between polysiloxane chains but can also be formed intermittently as a result of a partial reaction between the hydroxyl groups in the polyhydric alcohol derivative group originating from the component (B) and the Si—H groups of (A) when the crosslinking conditions are severe.

In the production of the polyhydric alcohol derivative-modified crosslinked silicone having a crosslinked structure, the component (C) may be further reacted with the component (A) after a reaction between the component (A) and the component (B), or the component (B) may be further reacted with the component (A) after a reaction between the component (A) and the component (C).

When the component (C) is further reacted with the component (A) after the reaction between the component (A) and the component (B), the average value of the number of silicon atom bonded hydrogen atoms per molecule of the component (A) reacting with the reactive unsaturated groups of the component (C) is preferably greater than or equal to 1.0. That is, the number of silicon atom bonded hydrogen atoms per molecule in the component (A) which constitute the crosslinking portion and react with the reactive unsaturated groups in the component (C) is, on average, greater than or equal to 1.0, preferably in a range of 0.2 to 1.5, and particularly preferably in a range of 0.6 to 1.3.

In the production of the polyhydric alcohol derivative-modified crosslinked silicone having a crosslinked structure, in addition to component (A), component (B), and component (C), a (Q) organic compound having one reactive unsaturated group per molecule (however, excluding the component (C2)) may be further reacted. One component (Q) or two or more components (Q) may be used. The reaction can be implemented successively preferably in the presence of a hydrosilylation reaction catalyst. It is noted that the definitions, types, and the like of the reactive unsaturated groups in the component (Q) are as described earlier.

For example, when the component (C) is further reacted with the component (A) after the reaction between the component (A) and the component (B), the component (Q) may be reacted with the component (A) before the reaction between the component (A) and the component (B), or the component (Q) may be reacted with the component (A) after the reaction between the component (A) and the component (B), or else, the component (Q) may be further reacted with the component (A) after the reaction of the component (C).

For example, when the component (B) is further reacted with the component (A) after the reaction between the component (A) and the component (C), the component (Q) may be reacted with the component (A) before the reaction between the component (A) and the component (C), or the component (Q) may be reacted with the component (A) after the reaction between the component (A) and the component (C), or else, the component (Q) may be further reacted with the component (A) after the reaction of the component (B).

Examples of the component (Q) include, (Q1) a siloxane dendron compound having one reactive unsaturated group per molecule, and (Q2) a hydrocarbon compound having one reactive unsaturated group per molecule, or chain organopolysiloxane having one reactive unsaturated group per molecule.

The compound represented by the above-described general formula (3') is preferable as the (Q1) siloxane dendron compound having one reactive unsaturated group per molecule.

The compound represented by the above-described general formula (2') or the above-described general formula (2'-1) is preferable as the (Q2) hydrocarbon compound having one reactive unsaturated group per molecule or chain organopolysiloxane having one reactive unsaturated group per molecule.

Example of the (Q2) hydrocarbon compound having one reactive unsaturated group per molecule include a compound similar to the above-described (e) hydrocarbon compound having one reactive unsaturated group per molecule.

In the production of a transparent or translucent liquid polyhydric alcohol derivative-modified silicone or a composition thereof according to the present invention, as desired, a water addition step may be included with the purpose of transparentization, and the like. However, it is desirable to not add water during production from the perspective of obtaining a high purity product.

Liquid Oil Agent Addition Step

The production method of a liquid high-purity polyhydric alcohol derivative-modified silicone or a composition thereof according to the present invention can further include, before and/or after and/or simultaneously with the purification-increasing treatment step, a liquid oil agent addition step of adding a liquid oil agent to the liquid polyhydric alcohol derivative-modified silicone or the composition thereof. Here, "liquid" has the same meaning as previously described.

The liquid oil agent preferably has affinity with the liquid polyhydric alcohol derivative-modified silicone. The liquid oil agent is preferably at least one oil agent selected from silicone oils, non-polar organic compounds, and low-polarity to high-polarity organic compounds that are liquid at 5 to 100° C., and the non-polar organic compounds and low-polarity to high-polarity organic compounds are preferably hydrocarbon oils, fatty acid ester oils, and liquid fatty acid triglycerides. These are components that are widely used as base materials particularly for cosmetic compositions, but it is possible to additionally use, as these oil agents, at least one or at least two compounds selected from among publicly known vegetable oils and fats, animal oils and fats, higher alcohols, fatty acid triglycerides, artificial sebum, and fluorine-based oils. Because the composition containing the polyhydric alcohol derivative-modified silicone modified by the polyhydric alcohol derivative exhibits excellent miscibility and dispersibility even in non-silicone-based oil agents when the polyhydric alcohol derivative-modified silicone has a long-chain alkyl group, hydrocarbon oils and fatty acid ester oils may be stably blended into cosmetics and the moisture retention characteristics of these non-silicone-based oil agents can be leveraged. Therefore, the composition containing the polyhydric alcohol derivative-modified silicone modified by the polyhydric alcohol derivative can improve the blending stability of these non-silicone-based oil agents in cosmetics.

By combining the hydrocarbon oil and/or the fatty acid ester oil with the silicone oil, in addition to the dry tactile sensation unique to silicone oils, moisture will be retained on the skin and a moisturizing feel whereby the skin or hair feels moisturized (also referred to as a luxurious tactile sensation) and smooth tactile sensation can be imparted to the cosmetic composition. Moreover, there is a benefit in that stability over time of the cosmetic composition will not be negatively affected. Furthermore, with a cosmetic composition comprising the hydrocarbon oil and/or the fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a non-silicone-based oil agent (e.g. a hydrocarbon oil, a fatty acid ester oil, or the like), the cosmetic composition comprising a non-silicone-based oil agent along with a silicone oil is advantageous in that a smoother, more luxurious tactile sensation is imparted.

The oil agents are the same as those disclosed by the present applicants in paragraphs [0141] to [0150] and the like of Patent Document 28 (Japanese Unexamined Patent Application Publication No. 2012-246446A).

The added amount of liquid oil agent in the liquid oil agent addition step is not particularly limited but may be from 5 to 1000 parts by mass, preferably from 10 to 500 parts by weight, and even more preferably from 50 to 200 parts by weight per 100 parts by mass of the liquid polyhydric alcohol derivative-modified silicone or composition thereof.

In the liquid oil agent addition step, the liquid polyhydric alcohol derivative-modified silicone or composition thereof and the liquid oil agent are preferably mixed to homogenize. Mixing to homogenize is preferably performed using mechanical power. For example, mixing can be performed with a paddle mixer, a propeller mixer, or in a reactor or a container equipped with mixing blades, and an emulsifier, a kneader, or the like may also be used as necessary. Furthermore, mixing to homogenize does not necessarily have to be performed at room temperature, and the temperature may be increased or decreased in accordance with the composition, fluidity, and the like. It is normally preferable to perform mixing to homogenize within a range of 0 to 70° C.

Unlike conventional polyether-modified silicone and the like, the polyhydric alcohol derivative-modified silicone composition according to the present invention is stable, inherently having little tendency to degrade due to oxidation by oxygen in the air. Therefore, there is no need for the operation of increasing oxidative stability by blending antioxidants such as phenols, hydroquinones, benzoquinones, aromatic amines, or vitamins in order to prevent oxidative degradation. However, stability further improves when such antioxidants, for example, BHT (2,6-di-t-butyl-p-cresol), vitamin E, and the like are added. In this case, the added amount of the antioxidant used is in a range (by weight (mass)) from 10 to 1000 ppm, and preferably from 50 to 500 ppm, of the polyhydric alcohol derivative-modified silicone.

The visible light transmittance of the liquid high-purity polyhydric alcohol derivative-modified silicone composition after the liquid oil agent addition step is preferably greater than or equal to 50%, more preferably greater than or equal to 70%, and even more preferably greater than or equal to 80%. Light of wavelength from 360 to 830 nm is preferred as the visible light, and light of wavelength from 400 to 760 nm is more preferred. For example, light of wavelength 750 nm may be used. An optical path length of 1 to 30 mm is preferred for transmittance measurement, and an optical path length of 5 to 20 mm is more preferred. For example, the transmittance measurement may be performed with an optical path length of 10 mm. Particularly when measured with an optical path length of 10 mm using light of wavelength 750 nm, light transmittance is greater than or equal to 50%, and more preferably greater than or equal to 70%, and even more preferably greater than or equal to 80%.

The content of polyhydric alcohol derivative-modified silicone in the liquid high-purity polyhydric alcohol derivative-modified silicone composition after the liquid oil agent addition step is not particularly limited, but is preferably from 10 to 99 wt. %, more preferably from 25 to 90 wt. %, and even more preferably from 50 to 80 wt. %, based on the total weight of the composition.

(Acid Treatment and Odor Reduction of Polyhydric Alcohol Derivative-Modified Silicone or Composition Thereof)

In the production method according to the present invention, the mixture, or the polyhydric alcohol derivative-modified silicone or the composition thereof (hereinafter, simply called the "polyhydric alcohol derivative-modified silicone or the composition thereof") is preferably treated with an acidic substance, and an odor substance and low boiling point component generated by the treatment of the acidic substance is removed by heating or decompressing. In such a case, it is possible to obtain a relatively high-quality polyhydric alcohol derivative-modified silicone or a composition thereof. While the treatment can be implemented in the presence of a non-polar solvent and/or a polar solvent and/or water, the acidic substance is preferably used by dissolving or dispersing in a polar solvent such as water, or the like, and it is more preferable to provide the treatment in a form including the acidic aqueous solution. Moreover, as described earlier, when the acid treatment step is performed before the purification-increasing treatment of the present invention, a better improvement in purity is achieved, which is preferable. Comprehensively considering the rationality and cost of the production process as well as the obtained effect, it is best to proceed with the procedure in the order of "synthesis of polyhydric alcohol derivative-modified silicone"→"acid treatment and odor reduction"→"purification-increasing treatment". However, when the need of acid treatment is low, such as in cases other than when the synthesis step involves the hydrosilylation reaction, the acid treatment step can be skipped. Also, the "liquid oil agent addition step" described earlier may be executed at any timing either before or after the three basic steps.

The acidic substance contained in the acidic aqueous solution can be selected optionally, but it is optimal to use at least one acidic inorganic salt which is solid at 25° C., is water-soluble, and has an aqueous solution pH of less than or equal to 4 at 25° C. when 50 g is dissolved in 1 L of ion exchanged water.

Furthermore, treatment using the acidic aqueous solution can be most preferably performed when the liquid polyhydric alcohol derivative-modified silicone is synthesized by a hydrosilylation reaction, and can also be preferably performed when the liquid polyhydric alcohol derivative-modified silicone is the liquid polyhydric alcohol derivative-modified crosslinked silicone. Here, for simplicity, the case of a liquid polyhydric alcohol derivative-modified silicone not including the crosslinked structure in a state of being synthesized by a hydrosilylation reaction will be described as an example of an acid treatment and odor reduction method for a polyhydric alcohol derivative-modified silicone and a mixture containing the same.

Acid treatment preferably includes:

a process (V) of synthesizing a polyhydric alcohol derivative-modified silicone or a reaction mixture containing the same as a main component by performing a hydrosilylation reaction on: a (ax) polyhydric alcohol derivative having carbon-carbon double bonds at the terminals of the molecular chain; and an (bx) organohydrogenpolysiloxane; and together with the synthesis step (V) or after the synthesis step (V), a process (W) of treating the polyhydric alcohol derivative-modified silicone or the reaction mixture containing the same as a main component in the presence of at least one (cx) acidic inorganic salt which is solid at 25° C., is water-soluble, and has an aqueous solution pH of less than or equal to 4 at 25° C. when 50 g is dissolved in 1 L of ion exchanged water.

In addition, because a treatment step using the acidic inorganic salt involves the generation of odor-causing substances, it is more preferable to include a step of removing odor-causing substances by heating or decompressing after the step (W), from the perspective of odor reduction effectiveness.

For example, in the step (V), when the hydrosilylation reaction is performed using a (ax) polyhydric alcohol derivative such as a polyhydric alcohol monoallyl ether and a (bx) straight-chain organohydrogenpolysiloxane represented by the above-described structural formula (1-1A) in amounts so that there is an excessive amount of the substance of the component (ax) with respect to silicon-bonded hydrogen atoms in the component (bx), the polyhydric alcohol derivative-modified silicone represented by the structural formula (1-1) is synthesized, and a crude product of a reaction mixture containing the polyhydric alcohol derivative-modified silicone and the unreacted component (ax) and containing the polyhydric alcohol derivative-modified silicone as a main component is obtained.

The step (W) is a step for efficiently reducing the odors of the polyhydric alcohol derivative-modified silicone or the composition thereof highly effectively and effectively suppressing the generation of odors over time by hydrolyzing the crude product using specific acidic inorganic salts, with practically no breakage of the silicon-oxygen bonds forming the main chain of polysiloxane or the carbon-oxygen bonds of side chain portions.

The step (W) specifically is a step of removing odor-causing substances from the crude product of the reaction mixture containing the polyhydric alcohol derivative-modified silicone as a main component by using hydrolysis, and it is characterized by performing treatment in the presence of at least one (cx) acidic inorganic salt which is solid at 25° C., is water-soluble, and has an aqueous solution pH of less than or equal to 4 at 25° C. when 50 g is dissolved in 1 L of ion exchanged water. It is noted that the pH of the aqueous sample solution can be measured at room temperature (25° C.) by using a pH gauge that makes use of a glass electrode, and specifically, the "HM-10P" manufactured by Toa Denpa Kogyo Co., Ltd. can be used.

The acidic inorganic salt serving as the component (cx) needs to be a solid at 25°, needs to be water-soluble, and the aqueous solution needs to have a pH of less than or equal to 4 when 50 g of the acidic inorganic salt is dissolved in 1 L of ion exchanged water. The pH is preferably less than or equal to 3.5 and particularly preferably less than or equal to 2.0. By using such a water-soluble acidic inorganic salt for hydrolysis treatment of the composition, it is possible to reduce odors in the polyhydric alcohol derivative-modified silicone or the composition thereof highly effectively and suppress odorization over time effectively, with almost no breakage of C—O bonds or Si—O bonds.

Examples that can be used as the acidic inorganic salt include acidic inorganic salts in which at least a monovalent hydrogen atom of the inorganic acid that is at least divalent is neutralized by a base. Examples of the inorganic acid that is at least divalent include sulfuric acid, sulfurous acid, and the like. Examples of the base include an alkali metal, ammonia, and the like.

More specifically, the component (cx) is preferably at least one acidic inorganic salt comprising a hydrogensulfate ion ($HSO_4^-$) or a hydrogensulfite ion ($HSO_3^-$) and a monovalent cation ($M^+$). Examples of the monovalent cation ($M^+$) include alkali metal ions or an ammonium ion. Particularly, the monovalent cation is preferably at least one selected from the group consisting of a sodium ion, a potassium ion, and an ammonium ion. Additionally, one type of the acidic inorganic salts may be used alone or at least two of the acidic inorganic salts may be combined and used. Furthermore, the acidic inorganic salts can be easily removed via filtration after the treatment because the acidic inorganic salts are solids at room temperature (25° C.). Additionally, because it is water soluble, the acidic inorganic salts can be easily rinsed off using water, even in the cleaning step after production.

On the other hand, in hydrolysis treatment based on an acetic acid salt, phosphoric acid salt, and the like that does not satisfy the conditions of the component (cx), it is impossible to sufficiently reduce the odor of the polyhydric alcohol derivative-modified silicone or the composition thereof after hydrolysis. Meanwhile in hydrolysis treatment based on a strong acid such as hydrochloric acid and the like, and in hydrolysis treatment based on a publicly known solid acid of zirconium sulfate and the like, the odor can be reduced by a certain amount, but C—O bonds and Si—O bonds of the polyhydric alcohol derivative-modified silicone break easily at the time of hydrolysis.

Specific examples of the acidic inorganic salt serving as the component (cx) are lithium hydrogensulfate, sodium hydrogensulfate, potassium hydrogensulfate, rubidium hydrogensulfate, cesium hydrogensulfate, ammonium hydrogensulfate, sodium hydrogensulfite, or hydrates thereof. The pH of aqueous solutions in which 50 g of the acidic inorganic salt is dissolved in 1 L of ion exchanged water is as shown in the table below. From the perspective of the technical benefit of reducing odor, as for the water soluble acidic inorganic salt having a pH of less than or equal to 2.0, it is most preferable to use at least one acidic inorganic salt selected from the group consisting of sodium hydrogensulfate, potassium hydrogensulfate, and ammonium hydrogensulfate.

TABLE 1

| Acidic inorganic salt | pH (50 g/L) |
| --- | --- |
| Sodium hydrogensulfate | less than or equal to 1.5 |
| Potassium hydrogensulfate | less than or equal to 2.0 |
| Ammonium hydrogensulfate | less than or equal to 1.5 |
| Sodium hydrogensulfite | 3.5 |

For example, treatment in the presence of the acidic inorganic salt refers to (1) decomposition treatment involving adding and stirring the acidic inorganic salt into the reaction system (for example, a reactor such as a flask) of the reaction mixture containing the polyhydric alcohol derivative-modified silicone synthesized by a hydrosilylation reaction as a main component, and (2) hydrolysis treatment or the like involving adding and stirring an acidic inorganic salt and water or an acidic inorganic salt, water, and a hydrophilic solvent. The treatment step using the acidic inorganic salt is preferably carried out in the presence of at least one of water and a hydrophilic solvent.

A particularly preferable hydrolysis treatment is a hydrolysis treatment whereby, after the step (V), at least an acidic inorganic salt and water are added to a reaction system containing a crude product of the reaction mixture containing the polyhydric alcohol derivative-modified silicone as a main component, and depending on the case, another hydrophilic solvent is further added with the objective of increasing the treatment efficiency by improving computability, and the solution is further stirred using a mechanical force. The hydrolysis treatment can be carried out at any temperature and treatment time, and can be carried out at a temperature from 0 to 200° C. and more preferably from 50 to 100° C. for a reaction time of from 0.1 to 24 hours and more preferably from approximately 0.5 to 10 hours. The amount of the acidic inorganic salt used can be selected appropriately in accordance with the treatment apparatus and the treatment time. However, the amount is preferably in a range of 50 to 10,000 ppm and more preferably in a range of 100 to 5,000 ppm with respect to the reaction mixture containing the polyhydric alcohol derivative-modified silicone as a main component.

After the above-described acid treatment, it is preferable to include a stripping step in which low-boiling components (propionaldehyde and the like), which are odor-causing substances, are removed. In addition, after stripping, it is possible to hydrolyze more of the propenyl ether group-containing polyhydric alcohol derivative or the like by treating again in the presence of an acidic inorganic salt, and propionaldehyde and the like, which are odor-causing substances, can be removed. At this time, there is an advantage that, because acidic inorganic salt remains, an acidic inorganic salt need not be newly added. Therefore, it is only necessary to add a hydrophilic solvent, typified by water. That is, the above-described step (W) and the stripping step can be repeated at least two times, with the purpose of increasing the degree of odor reduction, or the like.

Furthermore, the "materials with a low boiling point" which are removed by the stripping step, include not only propionaldehyde which is an odor-causing substance, but also the reaction solvents used in the hydrosilylation reaction (step (V)), the water used in the odor reduction treatment step, other hydrophilic solvents, and the like.

The stripping step (removal of materials with a low boiling point) may be performed, as a pre-step of the step (W), on the crude product of the reaction mixture containing the polyhydric alcohol derivative-modified silicone as a main component, or may be performed, as a post-step of the step (W), on the reaction mixture containing the polyhydric alcohol derivative-modified silicone as a main component. In addition, the stripping step can be respectively performed as the pre-step and post-step of the step (W). The stripping step is preferably performed after the step (W), with the purpose of removing propionaldehyde, which is an odor-causing substance generated by the hydrolysis reaction.

As the removal method, stripping under normal pressure or under reduced pressure is preferable, and stripping at a temperature of lower than or equal to 120° C. is preferable. In order to effectively perform the stripping, the stripping is preferably performed under reduced pressure or, for example, performed under a nitrogen gas or similar inert gas stream. A specific example of the operation for removing materials with a low boiling point is one in which a crude product of the reaction mixture containing the polyhydric alcohol derivative-modified silicone containing the materials with a low boiling point as a main component is placed in a flask having a refluxing cooler, a nitrogen injection port, or the like; and, while supplying nitrogen gas, the internal pressure is reduced, the internal temperature is increased, and the pressure and temperature are maintained so as to be constant. Thus, the light matter is removed. Here, typically, a decompression parameter is from 0.1 to 10.0 KPa, a heating temperature is from 40 to 120° C., and a treatment time is from 10 minutes to 24 hours.

Furthermore, after the acid treatment step, a basic substance may be used to neutralize the reaction mixture containing the polyhydric alcohol derivative-modified silicone as a main component. Examples of the basic substance include inorganic salt groups such as sodium hydroxide, potassium hydroxide, calcium hydroxide, barium hydroxide, ammonia water, and sodium hydrogen carbonate; organic bases such as various amines, and basic amino acids; and the like. The amount of the basic substance is preferably an amount needed to neutralize a reaction system comprising the reaction mixture containing the polyhydric alcohol derivative-modified silicone as a main component, but, as necessary, the amount of the basic substance may be adjusted to an amount by which weak acidity or weak alkalinity is obtained.

Noted that, an alkaline buffer may be further added in an amount corresponding to 100 ppm to 50000 ppm to the reaction mixture containing the polyhydric alcohol derivative-modified silicone obtained after the acid treatment step as a main component. A minute amount of acid may be locally dissolved in the reaction mixture containing the polyhydric alcohol derivative-modified silicone as a main component even after a neutralization or filtration step. By adding an alkaline buffer, the liquidity of the cosmetics or the like into which the polyhydric alcohol derivative-modified silicone is blended is maintained on the alkali side, which makes it possible to reduce the risk of odorization caused by the impurities of the polyhydric alcohol derivative-modified silicone. A useful alkaline buffer is not particularly limited as long as the alkaline buffer comprises a combination of a strong base and a weak acid. Examples of the alkaline buffer include trisodium phosphate, tripotassium phosphate, trisodium citrate, sodium acetate, and the like. Furthermore, these alkaline buffers may be added to a cosmetic composition starting material or the like comprising a polyhydric alcohol derivative-modified silicone or a composition thereof, or a mixture containing the same as a main component, or they may be added to a composition at the preparation stage or after the blending of a polyhydric alcohol derivative-modified silicone or cosmetic composition that contains another cosmetic composition starting material or water. By so doing, odor production during formulation or over time can be more effectively suppressed.

The polyhydric alcohol derivative-modified silicone or the mixture containing the same as a main component can also be subjected to hydrogenation treatment as a pre-step or a post-step of treatment in the presence of an acidic inorganic salt in the step (W). A deodorizing treatment using a hydrogenation reaction may be performed after treatment in the presence of the acidic inorganic salt of the step (W). On the other hand, the treatment in the presence of the acidic inorganic salt of the step (W) may be performed after deodorizing treatment using a hydrogenation reaction. However, hydrogenation treatment may generally lead to an increase in cost at the time of manufacturing the product.

A second aspect of the present invention is an external use preparation, cosmetics, or an industrial material containing the liquid high-purity polyhydric alcohol derivative-modified silicone or a composition thereof obtained by the production method of the present invention.
External Use Preparation and Cosmetics A liquid high-purity polyhydric alcohol derivative-modified silicone or a composition thereof obtained by the production method of the present invention can be suitably blended into an external use preparation or cosmetics and can form the external use preparation or cosmetics of the present invention. In addition, it is also possible to produce a starting material for external use preparations and cosmetics containing the polyhydric alcohol derivative-modified silicone or the composition thereof obtained by the production method of the present invention and to blend the starting material into an external use preparation or cosmetics.

In particular, because the liquid high-purity polyhydric alcohol derivative-modified silicone or the composition thereof obtained by the production method of the present invention has high transparency and has transparency that is stable with respect to the temperature history and even after storage over a long period of time, it can be suitably blended into external use preparations or cosmetics that require transparent or translucent appearance. In addition, the polyhydric alcohol derivative-modified silicone or the composition thereof obtained by the production method of the present invention has a low degree of odor and produces practically no odor during formulation or over time. Moreover, there is the advantage of breaking almost no silicon-oxygen bonds which may form the main chain of the polyhydric alcohol derivative-modified silicone and carbon-oxygen bonds which may form the side chains. Therefore, the polyhydric alcohol derivative-modified silicone or the composition thereof obtained by the production method of the present invention can be suitably used as a starting material for external use preparations and cosmetics used on the human body.

The proportion of the polyhydric alcohol derivative-modified silicone or the composition thereof in the starting material for external use preparations or cosmetics is preferably from 10 to 100 wt. % (mass %), more preferably from 20 to 100 wt. % (mass %), and even more preferably from 30 to 100 wt. % (mass %) relative to the total weight (mass) of the starting material. The proportion of the starting material blended into external use preparations or cosmetics is not particularly limited, but for example, can be from 0.1 to 40 wt. % (mass %), and is preferably from 1 to 30 wt. % (mass %), more preferably from 2 to 20 wt. % (mass %), and even more preferably from 3 to 10 wt. % (mass %) relative to the total weight (mass) of the external use preparations or the cosmetics.

The liquid high-purity polyhydric alcohol derivative-modified silicone or the composition thereof obtained by the production method of the present invention can be applied to applications common to the novel organopolysiloxanes described in Patent Document 25 (Japanese Unexamined Patent Application Publication No. 2011-246705A) and Patent Document 26 (Japanese Unexamined Patent Application Publication No. 2011-246706A), or the low-odor sugar alcohol-modified silicone described in Patent Document 27 (Japanese Unexamined Patent Application Publication No. 2012-246445A), or the novel liquid organopolysiloxane described in Patent Document 28 (Japanese Unexamined Patent Application Publication No. 2012-246446A), or the sugar alcohol-modified silicone described in Patent Document 29 (Japanese Unexamined Patent Application Publication No. 2012-046508A), depending on the structure and type of functional group present. In addition, the liquid high-purity polyhydric alcohol derivative-modified silicone composition obtained by the production method of the present invention can be used in the same manner as the novel organopolysiloxanes described in Patent Document 25 and Patent Document 26, the low-odor sugar alcohol-modified silicone described in Patent Document 27, the novel organopolysiloxane described in Patent Document 28, or the sugar alcohol-modified silicone described in Patent Document 29 with regard to combinations with any cosmetic starting material components, formulations, types, and formulation examples of external use preparations or particularly cosmetics, and can be blended into various cosmetics or the like.

The external use preparation according to the present invention is not particularly limited, as long as it is a composition applied to human body as cosmetics or a medicament. Specific examples of cosmetic composition products of the present invention include similar skin use cosmetic products such as skin cleansing agent products, skin care products, makeup products, antiperspirant products, and ultraviolet light blocking products; hair use cosmetic products such as hair use cleansing agent products, hair dressing products, hair use coloring products, hair growth products, hair rinsing products, hair conditioning products, and hair treatment products; and bath use cosmetic products. Examples of the medicament of the present invention include hair regrowth agents, hair growth promoters, analgesics, germicides, anti-inflammatory agents, refreshing agents, and skin anti-aging agents, but are not limited thereto.

The skin use cosmetic products can be used on any site of the entire body including the scalp, face (including lips, eyebrows, and cheeks), fingers, and fingernails. Specific examples thereof include skin cleansing agent products such as cleansing gels, cleansing creams, cleansing foams, cleansing milk, cleansing lotions, face washing creams, eye makeup removers, face washing foams, liquid soaps (body soaps), hand soaps, gel-like soaps, bar soaps, facial rinses, body rinses, shaving creams, nail polish removers, and acne treatment cosmetics; skin care products such as skin creams, scalp use treatments, skin milks, milk lotions, emulsions, toners, fluid moisturizers, beauty essence, facial packs, body powders, essences, shaving lotions, and massage lotions; makeup products such as foundations, liquid foundations, oil-based foundations, makeup bases, powders, face powders, concealers, Blemish Balm (BB) creams, Color Control (CC) creams, lipsticks, lip creams, cheek coloring, lip gloss, eye shadows, eye liners, eye creams, eyebrow powders, eyelash cosmetic products, eyebrow pencils, eyebrow brushes, mascaras, blusher, cheek use cosmetics (cheek color, cheek rouge), manicures, pedicures, nail colors, nail lacquers, enamel remover, and nail polishes; antiperspirants such as deodorants; and ultraviolet light blocking products such as sunscreen agents, and tanning use medicaments (sun tanning agent).

Examples of the hair use cosmetic products include hair use cleansing agents such as shampoos, and rinse-in shampoos; hair dressing products such as hair oils, hair waxes, hair use curl holding agents, setting agents, hair creams, hairsprays, and hair liquids; hair use coloring products such as hair dying agents, hair color sprays, hair color rinses, and hair color sticks; hair growing products such as hair tonics, hair treatment essences, and hair packs; and hair rinse or hair conditioning products such as oil rinses, cream rinses, treatment rinses, hair conditioners, and hair treatments. In addition, examples of the bath use cosmetic products include bath oils, bath salts, and bath foams.

The form of the external use preparation compositions and in particular, the cosmetics according to the present invention is not particularly limited, and these can be suitably used in the form of a liquid, W/O (water-in-oil type) emulsion, O/W (oil-in-water type) emulsion, W/O cream-like, O/W cream-like, solid (stick shape and the like), polyol-in-oil type emulsion, oil-in-polyol type emulsion, multilayer emulsion such as W/O/W or O/W/O, two layer separation type (shake mixing type before use), paste-like, gel-like, powder-like, multi-layer, mousse-like, mist-like, granule, flake, crushed stone, and the like. Particularly preferable forms are W/O emulsions, W/O creams, solids, paste-like, gel-like, and powder-like.

The container of the external use preparations, particularly the cosmetics according to the present invention is also not particularly limited, and the external use preparations and cosmetics can be filled into any container such as jars, pumps, tubes, bottles, pressure can discharge vessels, pressure-tight aerosol containers, light-resistant containers, compact containers, metal plates, stick containers, roll in/out container, spray containers, partitioned containers with liquid mixture discharge opening, and the like. Although common silicone formulations tend to separate in a tube, the external use preparation, particularly the cosmetics according to the present invention, has excellent stability, as a result they can be stored in a stable manner even when filled in a tube container, which proves to be advantageous.

The following other components generally used in external use preparations or cosmetics may be added to the external use preparation or the cosmetics of the present invention, provided that such components do not inhibit the effectiveness of the present invention: water, powders or coloring agents, hydroxy acid, wax, fibers, alcohols, water-soluble polymers, film-forming agents, oil agents, oil-soluble gelling agents, organo-modified clay minerals, surfactants, resins, UV absorbers, salts, moisturizing agents, preservatives, antimicrobial agents, perfumes, antioxidants, pH adjusting agents, chelating agents, refreshing agents, anti-inflammatory agents, skin beautifying components (skin-lightening agents, cell activating agents, agents for ameliorating skin roughness, circulation promoters, astringents, antiseborrheic agents, and the like), vitamins, amino acids, nucleic acids, hormones, clathrate compounds, and the like; bioactive substances, medicament active ingredients, and perfumes. However, the additives are not particularly limited to thereto.

The water that can be used in the cosmetics or external use preparations according to the present invention needs to be clean and free of components that are harmful to the human body, and examples thereof include tap water, purified water, mineral water, and deep sea water.

(Oil Agent)

The oil agent that can be used in the cosmetics or external use preparations according to the present invention is preferably at least one oil agent selected from silicone oils, non-polar organic compounds, and low-polarity to high-polarity organic compounds that are liquid at 5 to 100° C., and the non-polar organic compounds and low-polarity to high-polarity organic compounds are preferably hydrocarbon oils, fatty acid ester oils, and liquid fatty acid triglycerides. These are components that are widely used as base materials particularly for cosmetic compositions, but it is possible to additionally use, as these oil agents, at least one or at least two of compounds selected from among publicly known vegetable oils and fats, animal oils and fats, higher alcohols, fatty acid triglycerides, artificial sebum, and fluorine-based oils.

By combining the hydrocarbon oil and/or the fatty acid ester oil with the silicone oil, in addition to the dry tactile sensation unique to silicone oils, moisture will be retained on the skin and a moisturizing feel whereby the skin or hair feels moisturized (also referred to as a luxurious tactile sensation) and smooth tactile sensation can be imparted to the cosmetic composition. Moreover, there is a benefit in that stability over time of the cosmetic composition will not be negatively affected. Furthermore, with a cosmetic composition comprising the hydrocarbon oil and/or the fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a non-silicone-based oil agent (e.g. a hydrocarbon oil, a fatty acid ester oil, or the like), the cosmetic composition comprising a non-silicone-based oil agent along with a silicone oil is advantageous in that a smoother, more luxurious tactile sensation is imparted.

The oil agents are the same as those disclosed by the present applicants in paragraphs [0141] to [0150] and the like of Patent Document 28 (Japanese Unexamined Patent Application Publication No. 2012-246446A).

Powder or Coloring Agent

A powder or coloring agent which can be used in the cosmetics or external use preparations according to the present invention is one that is commonly used as a component of cosmetics, and includes white or coloring pigments and extender pigments. The white or coloring pigments are used to impart color and the like to cosmetics, and the extender pigments are used to improve the tactile sensation and the like of cosmetics. As for "powder" in the present invention, white or coloring pigments as well as extender pigments commonly used in cosmetics can be used without any particular limitations. In the present invention, preferably, at least one or at least two of the powders are compounded. The form (sphere, bar, needle, plate, irregular shape, spindle, cocoon, or the like), particle diameter (aerosol, micro-particle, pigment-grade particle, or the like), and particle structure (porous, nonporous, or the like) of the powder are not limited in any way, but an average primary particle diameter is preferably in a range of 1 nm to 100 μm. Particularly, when compounding the powder or coloring agent as a pigment, preferably at least one or at least two selected from an inorganic pigment powder, an organic pigment powder, and a resin powder having an average particle diameter in a range of 1 nm to 20 μm is compounded.

Examples of the powder include inorganic powders, organic powders, surfactant metal salt powders (metallic soaps), colored pigments, pearl pigments, metal powder pigments, and the like. Compounded products of these pigments can be used. Furthermore, the surfaces of these pigments may be water-repellent treated.

Specific examples thereof include the same powders or coloring agents disclosed in paragraphs [0219] to [0226] or the like of Patent Document 28.

Of the powders recited, description of a silicone elastomer powder shall be given. The silicone elastomer powder is a crosslinked product of a straight-chain diorganopolysiloxane formed principally from diorganosiloxy units (D units), and can be suitably obtained by crosslinking an organohydrogenpolysiloxane having a silicon-bonded hydrogen atom on the side chain or the terminal and a diorganopolysiloxane having an unsaturated hydrocarbon group such as an alkenyl group or the like on the side chain or the terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and smearing of makeup can be prevented. When surface treatment is performed on the polyhydric alcohol derivative-modified silicone or the composition thereof obtained by the production method of the present invention, uniform treatment can be performed with good treatment efficiency, and thus it is possible to provide a unique effect or feel corresponding to the type of the polyhydric alcohol derivative-modified silicone without diminishing the suede-like feel of the silicone elastomer powder. Furthermore, when the polyhydric alcohol derivative-modified silicone or the composition thereof is blended into cosmetics together with a silicone elastomer powder, the dispersion stability of the powder in the overall cosmetics is improved, and it is possible to obtain a cosmetic that is stable over time.

The silicone elastomer powder can be in various forms such as spherical, flat, irregular shape, or the like. The silicone elastomer powder may also be in the form of an oil dispersion. With the cosmetics of the present invention, a silicone elastomer powder having a particle shape is suitably compounded, the silicone elastomer powder has the primary particle diameter observed using an electron microscope and/or the average primary particle diameter measured by laser analysis or scattering in a range of 0.1 to 50 μm, and the primary particle of spherical shape. A silicone elastomer that constitutes the silicone elastomer powder is preferably one having a hardness, as measured using a type A durometer in the "Rubber, Vulcanized or Thermoplastic—Determination of Hardness" specified in JIS K 6253, of less than or equal to 80, and more preferably less than or equal to 65.

Of these silicone elastomer powders, specific examples of silicone elastomer spherical powders, in particular, are the same as those disclosed in paragraph [0223] of Patent Document 28 and may be silicone elastomer powders that have been subjected to various surface treatments such as water-repellent treatment, as disclosed in paragraphs [0224] and [0225] of Patent Document 28.

It is possible to further blend another surfactants in the cosmetics or external use preparations of the present invention. These other surfactants are components that function as cleansing components of the skin or the hair or, alternatively, as the oil emulsifier, and can be selected as desired depending on the type and function of the cosmetics. More specifically, the other surfactants can be selected from the group consisting of an anionic surfactant, a cationic surfactant, a nonionic surfactant, an amphoteric surfactant, and a semipolar surfactant. In particular, it is preferable to use a silicone-based nonionic surfactant in combination.

These surfactants are the same as those disclosed in paragraphs [0237] to [0242], and the like of Patent Document 28. The polyhydric alcohol derivative-modified silicone according to the present invention functions as a dispersing agent because it has polar groups and non-polar groups in the molecule. Therefore, when used in combination with a nonionic surfactant, it functions as an aid to enhance the stability of the nonionic surfactant, and may improve the overall stability of the formulation. In particular, the liquid high-purity polyhydric alcohol derivative-modified silicone or the composition thereof obtained by the production method of the present invention can be used in combination with a polyoxyalkylene-modified silicone (polyether-modified silicone), a (poly)glycerin derivative-modified silicone, a sugar derivative-modified silicone, etc. due to its enhanced compatibility and affinity with various modified silicones. Moreover, nonionic surfactants of these silicones in which an alkyl branch, a straight chain silicone branch, a siloxane dendrimer branch, or the like is provided as necessary along with the hydrophilic group can also be suitably used.

Depending on the purpose, the cosmetics or external use preparations of the present invention can contain at least one or at least two polyhydric alcohols and/or lower monohydric alcohols. These alcohols are the same as those disclosed in paragraph [0227] and the like of Patent Document 28.

Depending on the purpose, the cosmetics or the external use preparations of the present invention can contain at least one or at least two inorganic salts and/or organic salts. These salts are the same as those disclosed in paragraph [0248] and the like of Patent Document 28.

Depending on the purpose, the cosmetics or the external use preparations of the present invention can contain at least one selected from the group consisting of a crosslinking organopolysiloxane, an organopolysiloxane elastomer spherical powder, a silicone resin, an acryl silicone dendrimer copolymer, a silicone raw rubber, a polyamide-modified silicone, an alkyl-modified silicone wax, and an alkyl-modified silicone resin wax. These silicone-based components are the same as those disclosed in paragraphs [0262] to [0287] and the like of Patent Document 28.

Depending on the purpose, the cosmetics or external use preparations of the present invention can contain at least one or at least two water-soluble polymers. These water-soluble polymers are the same as those disclosed in paragraphs [0228] to [0232] and the like of Patent Document 28.

Depending on the purpose, the cosmetics or external use preparations of the present invention can contain at least one or at least two ultraviolet light blocking components. These ultraviolet light blocking components are the same as the organic and inorganic ultraviolet light blocking components disclosed in paragraphs [0243] to [0247] and the like of Patent Document 28, but specifically, an ultraviolet light blocking agent that can be suitably used is at least one selected from the group consisting of microparticulate titanium oxide, microparticulate zinc oxide, 2-ethylhexyl p-methoxycinnamate, 4-tert-butyl-4'-methoxydibenzoylmethane, diethylamino hydroxybenzoyl hexyl benzoate, benzotriazole-based UV absorbers, and 2,4,6-tris[4-(2-ethylhexyloxycarbonyl)anilino]1,3,5-triazine (INCI: octyl triazone), and 2,4-bis([4-(2-ethyl-hexyloxy)-2-hydroxy]phenyl)-6-(4-methoxyphenyl)-1,3,5-triazine (INCI: bis-ethylhexyloxyphenol methoxyphenyl triazine, trade designation: Tinosorb®S). These ultraviolet light blocking components are generally used, are easy to acquire, and have high ultraviolet light blocking effects and, thus can be suitably used. In particular, using both inorganic and organic ultraviolet light blocking components is preferable, and using a UV-A blocking component in combination with a UV-B blocking component is more preferable.

By using an ultraviolet light blocking component in combination with the polyhydric alcohol derivative-modified silicone or the composition thereof in the cosmetics or the external use preparations of the present invention, it is possible to stably disperse the ultraviolet light blocking component in the cosmetics while improving the feeling to touch and storage stability of the overall cosmetics, and thus, it is possible to impart excellent ultraviolet light blocking properties to the cosmetics.

Various components other than the above-described components can be used in the cosmetics or external use preparations of the present invention, provided that such use does not impair the purposes of the present invention. Examples of various components include hydroxy acids, waxes, fibers, oil-soluble gelling agents, organo-modified clay minerals, water swelling clay minerals, preservatives, bioactive components, skin beautifying components, pH adjusting agents, antioxidants, solvents, chelating agents, moisturizing components, and perfumes. These optional components for cosmetic products are the same as those disclosed in paragraphs [0235], [0233], [0249] to [0260] and the like of Patent Document 28.

Additionally, when the cosmetics or external use preparations according to the present invention is an antiperspirant, or depending on the purpose, the cosmetics or external use preparations can contain an anti-perspiration active component and/or a deodorant agent. These antiperspirant components and deodorant components are the same as those disclosed in paragraphs [0254] to [0263] and the like of Patent Document 27. Similarly, when the cosmetics or external use preparations according to the present invention is an antiperspirant composition, the preparation, method of use, and the like of the various antiperspirant compositions are the same as those disclosed in paragraphs [0264] to [0315] and the like of Patent Document 27.

INDUSTRIAL APPLICABILITY

The production method of a liquid high-purity polyhydric alcohol derivative-modified silicone or a composition thereof of the present invention is inexpensive and simple, produces little waste, has excellent yield or productivity, and can reasonably cope with production on a commercial scale. Further, the polyhydric alcohol derivative-modified silicone or the composition thereof obtained by the production method of the present invention poses an extremely little risk of phase separation or sedimentation of unreacted starting material and the like after production. Particularly, since the liquid polyhydric alcohol derivative-modified silicone or the composition thereof obtained by the production method of the present invention is stable with respect to the temperature history and is also stable after storage over a long period of time, an appearance with a high transparency is maintained, and therefore, the problems that originate from an opaque appearance are eliminated, and moreover, since dilution by a liquid oil agent is also possible while maintaining transparency, the polyhydric alcohol derivative-modified silicone or the composition thereof has an excellent handleability. Therefore, the present invention solves the fundamental problems of the conventional polyhydric alcohol-derived silicone.

Therefore, the liquid high-purity polyhydric alcohol derivative-modified silicone or the composition thereof according to the present invention not only can be used in cosmetics or external use preparations such as medicaments, but also can be widely used in general industrial applications, and can provide the above various applications with the surface activity, emulsification/dispersion effect, surface treatment effect, adsorption effect, coating effect, moisture retention/water retention effect, emollient effect, abrasion reduction effect, lubrication effect, penetrating capability, solubilizing/compatibilizing capability, protection effect, adhesion effect, viscosity-increasing or viscosity-adjusting effect, or maintenance of these effects, and the like that are intrinsic to polyhydric alcohol derivative-modified silicones.

Specifically, the liquid high-purity polyhydric alcohol derivative-modified silicone or the composition thereof obtained by the production method of the present invention can be suitably used not only as a starting material for external use preparations, medicaments, or cosmetics, but also, for example, as a fiber treating agent, a varnish or paint additive with excellent heat resistance, weather resistance, and electrical characteristics, a coating agent, a primer, a tackifier, a polyol main agent or a foam stabilizer or a modifier for various urethanes or foaming materials, a mold-releasing agent or peeling agent, an antifoam agent, greases or oil compounds, oils for insulation, burnishing, water repellency, heating/cooling mediums, lubrication, or the like, a modifier, additive, or surface treating agent for a rubber or resin, a compounding agent, modifier, or precursor for a silane coupling agent, a coating material or sealing material for a building/lining, a protecting agent or lubricant or buffering agent for optical fibers/electrical lines, and starting materials for general industrial materials such as electronic/electrical parts.

EXAMPLES

The present invention will be described in detail hereinafter using examples and comparative examples, but the present invention is not limited to the examples described below.

Note that in the production examples and comparative examples below, the language "production of polyhydric alcohol derivative-modified silicone No. X" is used for the sake of convenience, but the obtained products are in the form of mixtures containing a small amount of unreacted starting material and the like in addition to the main components.

In the following compositional formulae, "Me" represents a methyl ($-CH_3$) group, "M" represents a $Me_3SiO$ group (or an $Me_3Si$ group), "D" represents an $Me_2SiO$ group, "$D^H$" represents an MeHSiO group, and "$M^R$" and "$D^R$" respectively represent units in which a methyl group in "M" or "D" is modified by any substituent. Additionally, in the production examples, "IPA" represents isopropyl alcohol.

Production Example 1

Synthesis of Polyhydric Alcohol Derivative-Modified Silicone No. 1

315.2 g of methylhydrogenpolysiloxane expressed by the average composition formula $MD_{37}D^H{}_{12.7}M$, 27.7 g of vinyl tris-trimethylsiloxy silane expressed by the average composition formula: $CH_2=CH-Si(OSi(CH_3)_3)_3$, and 67.1 g of hexadecene (α-olefin purity 91.7%) were prepared in a reactor, and 0.27 mL of a hexamethyl disiloxane solution of platinum-1,3-divinyl-1,1,3,3-tetramethyl disiloxane complex (Pt concentration 4.5 wt. %) was added while stirring under a nitrogen stream, and heating was performed in an oil bath at 60° C. After 20 minutes, as a result of generation of heat, the reaction liquid reached a maximum temperature of 68° C.

Thereafter, the reaction liquid was cooled to less than or equal to 40° C., 67.1 g of the hexadecene and 0.13 mL of platinum catalyst were added, and a reaction was performed for two hours at 40 to 70° C. 2 g of the reaction liquid was sampled, and it was confirmed with an alkali decomposition gas generation method (the remaining Si—H groups are decomposed using a KOH ethanol/aqueous solution, and the reaction rate is calculated from the volume of the generated hydrogen gas) that the reaction had reached the target.

Next, 55.9 g of diglycerinmonoallyl ether (average value of number of repetitions of glycerin unit=1.7), 336 g of IPA, and 0.06 g of vitamin E were prepared as the reaction mixture, 0.27 mL of the above-described platinum catalyst solution was added at 40 to 45° C., and after performing a reaction for 2.5 hours at 40 to 60° C., the same method was used to confirm that the reaction rate had reached the target.

Finally, 67.1 g of the hexadecene and 0.40 mL of the platinum catalyst were added and a reaction was performed for five hours at 45 to 60° C., and when the same method was used for confirmation, the reaction was found to have been completed, and a polyhydric alcohol derivative-modified silicone expressed by the average composition formula: $MD_{37}D^{R*11}{}_{8.7}D^{R*21}{}_3D^{R*32}{}_1M$ was found to have been generated. In this formula, $R^{*11}$, $R^{*21}$, and $R^{*32}$ are as described below.

$R^{*11}=-C_{16}H_{33}$
$R^{*21}=-C_3H_6O-(C_3H_6O_2)_n-H$, n=1.7
$R^{*32}=C_2H_4Si(OSiMe_3)_3$

Next, after removing low-boiling components at 60 to 90° C. under reduced pressure, an aqueous solution of 0.090 g of sodium hydrogensulfate monohydrate/7.5 g of ion exchanged water was added, treatment was performed for 20 minutes at 70 to 75° C., and then, after further reducing the pressure to 20 Torr, the generated odor component and water were removed. Thereafter, 7.5 g of ion exchanged water was again added, an operation in which decompression was performed in the same manner to remove the odor component and water was repeated two times (the last decompression operation was maintained at less than or equal to 10 Torr for one hour at −60 to 70° C.), and then, the pressure was restored.

A separate solution was prepared by dissolving 0.06 g of sodium bicarbonate in 3 g of ion exchanged water. This solution was added to the reaction system, and neutralization was performed by stirring for 30 minutes at 65 to 70° C., following which the decompression-dehydration operation was performed again to obtain 593 g of a composition containing the polyhydric alcohol derivative-modified silicone No. 1 expressed by the average composition formula: $MD_{37}D^{R*11}{}_{8.7}D^{R*21}{}_3D^{R*32}{}_1M$ as a light brown opaque viscous liquid. Here, $R^{*11}$, $R^{*21}$, and $R^{*32}$ are as described above.

Production Example 2

Synthesis of Polyhydric Alcohol Derivative-Modified Silicone No. 2

313.8 g of methylhydrogenpolysiloxane expressed by the average composition formula $MD_{37}D^H{}_{12.7}M$, 27.6 g of vinyl tris-trimethylsiloxy silane expressed by the average composition formula: $CH_2=CH-Si(OSi(CH_3)_3)_3$, and 66.8 g of hexadecene (α-olefin purity 91.7%) were prepared in a reactor, and 0.27 mL of a hexamethyl disiloxane solution of platinum-1,3-divinyl-1,1,3,3-tetramethyl disiloxane complex (Pt concentration 4.5 wt. %) was added while stirring under a nitrogen stream, and heating was performed in an oil bath at 60° C. After 20 minutes, as a result of generation of heat, the reaction liquid reached a maximum temperature of 74° C.

Thereafter, the reaction liquid was cooled to less than or equal to 40° C., 66.7 g of the hexadecene and 0.13 mL of platinum catalyst were added, and a reaction was performed for 1.5 hours at 40 to 70° C. 2 g of the reaction liquid was sampled, and it was confirmed with an alkali decomposition gas generation method that the reaction had reached the target.

Next, 58.3 g of high-purity chain diglycerinmonoallyl ether (number of repetitions of glycerin unit=2), 336 g of IPA, and 0.06 g of vitamin E were prepared as the reaction mixture, 0.27 mL of the platinum catalyst solution was added at 40 to 45° C., and after performing a reaction for 2.5 hours at 40 to 60° C., the same method was used to confirm that the reaction rate had reached the target.

Finally, 66.9 g of the hexadecene and 0.40 mL of the platinum catalyst were added and a reaction was performed for five hours at 45 to 60° C., and when the same method was used for confirmation, the reaction was found to have been completed, and a polyhydric alcohol derivative-modified silicone expressed by the average composition formula:

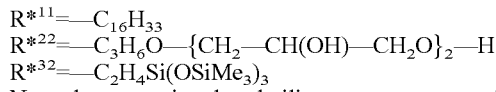
$MD_{37}D^{R*11}{}_{8.7}D^{R*22}{}_{3}D^{R*32}{}_{1}M$ was found to have been generated. In this formula, $R^{*11}$, $R^{*22}$, and $R^{*32}$ are the same as described below.

$R^{*11}$=—$C_{16}H_{33}$
$R^{*22}$=—$C_3H_6O$—{$CH_2$—$CH(OH)$—$CH_2O$}$_2$—H
$R^{*32}$=—$C_2H_4Si(OSiMe_3)_3$

Next, by removing low-boiling components under the same conditions as Production Example 1, and performing treatment by acidic substance/decompression-dehydration, odor removal, neutralization/dehydration, 595 g of a composition containing the polyhydric alcohol derivative-modified silicone No. 2 expressed by the average composition formula: $MD_{37}D^{R*11}{}_{8.7}D^{R*22}{}_{3}D^{R*32}{}_{1}M$ was obtained as a grayish brown opaque viscous liquid. Here, $R^{*11}$, $R^{*22}$, and $R^{*32}$ are as described above.

Production Example 3

Synthesis of Polyhydric Alcohol Derivative-Modified Silicone No. 3

401.1 g of methylhydrogen polysiloxane expressed by the average composition formula: $MD_{43.4}D^{H}{}_{7.4}M$, 3.5 g of vinyl tris-trimethylsiloxy silane expressed by the average composition formula: $CH_2$=$CH$—$Si(OSi(CH_3)_3)_3$, and 75.0 g of hexadecene (α-olefin purity 91.7%) were prepared in a reactor, and 0.40 mL of a hexamethyl disiloxane solution of platinum-1,3-divinyl-1,1,3,3-tetramethyl disiloxane complex (Pt concentration 4.5 wt. %) was added while stirring under a nitrogen stream. After performing a reaction for one hour at 30 to 75° C., 2 g of the reaction liquid was sampled, and it was confirmed with an alkali decomposition gas generation method that the reaction had reached the target.

Next, 45.7 g of diglycerinmonoallyl ether (average value of number of repetitions of glycerin unit=1.7), 341 g of IPA, 0.07 g of vitamin E were prepared as the reaction mixture, 0.67 mL of the platinum catalyst solution was added at 40 to 50° C., and after performing a reaction for 2.5 hours at 40 to 60° C., the same method was used to confirm that the reaction rate had reached the target.

Finally, 75.1 g of hexadecene and 0.27 mL of the platinum catalyst were added and a reaction was performed for 1.5 hours at 45 to 60° C., and when the same method was used for confirmation, the reaction was found to have been completed, and a polyhydric alcohol derivative-modified silicone expressed by the average composition formula: $MD_{43.4}D^{R*11}{}_{5.3}D^{R*21}{}_{2}D^{R*32}{}_{0.1}M$ was found to have been generated. In this formula, $R^{*11}$, $R^{*21}$, and $R^{*32}$ are as described below.

$R^{*11}$=—$C_{16}H_{33}$
$R^{*21}$=—$C_3H_6O$—$(C_3H_6O_2)_n$—H, n=1.7
$R^{*32}$=—$C_2H_4Si(OSiMe_3)_3$

Next, by removing low-boiling components under the same conditions as Production Example 1, and performing treatment by acidic substance/decompression-dehydration, odor removal, neutralization/dehydration, 596 g of a composition containing the polyhydric alcohol derivative-modified silicone No. 3 expressed by the average composition formula: $MD_{43.4}D^{R*11}{}_{5.3}D^{R*21}{}_{2}D^{R*32}{}_{0.1}M$ was obtained as a light brown opaque viscous liquid. Here, $R^{*11}$, $R^{*21}$, and $R^{*32}$ are as described above.

Production Example 4

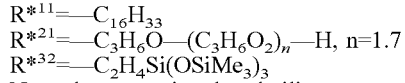
Synthesis of Polyhydric Alcohol Derivative-Modified Silicone No. 4

399.7 g of methylhydrogen polysiloxane expressed by the average composition formula: $MD_{43.4}D^{H}{}_{7.4}M$, 3.4 g of vinyl tris-trimethylsiloxy silane expressed by the average composition formula: $CH_2$=$CH$—$Si(OSi(CH_3)_3)_3$, and 74.7 g of hexadecene (α-olefin purity 91.7%) were prepared in a reactor, and 0.40 mL of hexamethyl disiloxane solution of platinum-1,3-divinyl-1,1,3,3-tetramethyl disiloxane complex (Pt concentration 4.5 wt. %) was added while stirring under a nitrogen stream. After performing a reaction for one hour at 40 to 60° C., 2 g of the reaction liquid was sampled, and it was confirmed with an alkali decomposition gas generation method that the reaction had reached the target.

Next, 47.5 g of high-purity chain diglycerinmonoallyl ether (number of repetitions of glycerin unit=2), 341 g of IPA, and 0.06 g of vitamin E were prepared as the reaction mixture, 0.27 mL of the platinum catalyst solution was added at 45 to 50° C., and after performing a reaction for one hour at 45 to 60° C., the same method was used to confirm that the reaction rate had reached the target.

Finally, 74.7 g of the hexadecene and 0.40 mL of platinum catalyst were added and a reaction was performed for one hour at 50 to 60° C., and when the same method was used for confirmation, the reaction was found to have been completed, and a polyhydric alcohol derivative-modified silicone expressed by the average composition formula: 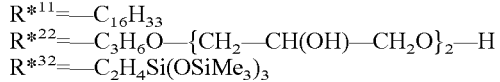 $MD_{43.4}D^{R*11}{}_{5.3}D^{R*22}{}_{2}D^{R*32}{}_{0.1}M$ was found to have been generated. In this formula, $R^{*11}$, $R^{*22}$, and $R^{*32}$ are the as described below.

$R^{*11}$=—$C_{16}H_{33}$
$R^{*22}$=—$C_3H_6O$—{$CH_2$—$CH(OH)$—$CH_2O$}$_2$—H
$R^{*32}$=—$C_2H_4Si(OSiMe_3)_3$

Next, by removing low-boiling components under the same conditions as Production Example 1, and performing treatment by acidic substance/decompression-dehydration, odor removal, neutralization/dehydration, 597 g of a composition containing the polyhydric alcohol derivative-modified silicone No. 4 expressed by the average composition formula: $MD_{43.4}D^{R*11}{}_{5.3}D^{R*22}{}_{2}D^{R*32}{}_{0.1}M$ was obtained as a grayish brown opaque viscous liquid. Here, $R^{*11}$, $R^{*22}$, and $R^{*32}$ are as described above.

In addition, the mass ratio of a main component of the composition thus obtained (polyhydric alcohol derivative-modified silicon No. 4) and an impurity glycerin derivative that is the cause of turbidity was estimated. In the Production Example 4, the molar number of a C=C group of the high-purity chain diglycerinmonoallyl ether was formulated to become 1.10 times of the molar number of a $D^H$ group with that is to react therewith. Therefore, the amount consumed by hydrosilylation out of 47.5 g used was calculated to be 47.5 g/1.10=43.2 g, and the excess was calculated to be 4.3 g. On the other hand, two hydrophobic modifiers (vinyl tris-trimethylsiloxy silane and hexadecene) were also prepared in slight excess with respect to the $D^H$ group, but were ignored for simplicity. Thus, the mass of the modified silicone that is the main component was calculated to be 582.1 g according to the molar number of the starting material methylhydrogenpolysiloxane and the molecular weight and the added molar number of each modifier. From the above, the abundance ratio of the main component and the turbidity component was found to be 582.1 g: 4.3 g=99.27:0.73 (turbidity component was 0.74% of the main component). It is understood that in this example, the hydrophilic impurities less even than 1% resulted in intense turbidity in the polyhydric alcohol derivative-modified silicon composition.

Production Example 5

Synthesis of Polyhydric Alcohol Derivative-Modified Silicone No. 5

137.7 g of methylhydrogenpolysiloxane expressed by the average composition formula: $MD_{42.9}D^{H}{}_{6.7}M$ and 14.9 g of 3-methacryloxy propyl(tris(trimethylsiloxy)silylethyl dimethylsiloxy)silane expressed by the following average composition formula:

[Chemical Formula 57]

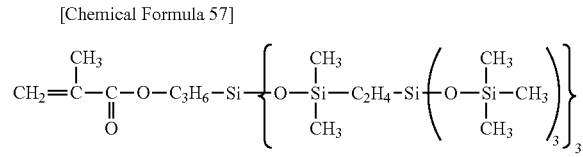

were prepared in a reactor, and heated to 80° C. while stirring under a nitrogen stream. 0.12 mL of isopropyl alcohol solution of a platinum-1,3-divinyl-1,1,3,3-tetramethyldisiloxane complex (Pt concentration 0.45 wt. %) was added, and a reaction was performed for three hours at 80 to 90° C. Then, a small amount of the reaction liquid was sampled, and it was confirmed with an alkali decomposition gas generation method that the reaction rate had reached the target.

Next, 38.4 g of hexadecene (α-olefin purity 91.7%) was added to the reaction mixture, and after performing a reaction for one hour at 85 to 105° C., the same method was used to confirm that the reaction rate had reached the target.

Thereafter, 9.3 g of diglycerinmonoallyl ether (average value of number of repetitions of glycerin unit=2.0) and 120 g of isopropyl alcohol (IPA) were added to the reaction mixture, and 0.20 mL of the platinum catalyst was added. After a reaction was performed for one hour at 70 to 85° C., the mixture was sampled. As a result of calculating the reaction rate, a modified silicone intermediate represented by the average composition formula: $MD_{42.9}D^{R*31}_{0.3}D^{R*23}_{0.8}D^{R*11}_{4.4}D^{H}_{1.2}M$ was found to have been produced. Here, $R^{*11}$, $R^{*23}$, and $R^{*31}$ are as described below.

$R^{*11}=-C_{16}H_{33}$ $R^{*23}=-C_3H_6O-(C_3H_6O_2)_n-H$, n=2.0

[Chemical Formula 58]

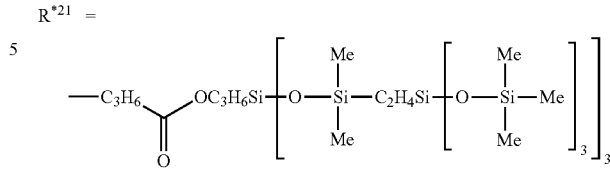

The reaction liquid was cooled to 50° C., and after 2.1 g of 1,5-hexadiene was added thereto, a reaction was performed for four hours at 50 to 75° C. Here, the Vi/H molar ratio upon crosslinking was 1.17. The mixture was sampled, and when the reaction rate was calculated, the reaction has been almost completed. Next, by removing the low-boiling components at a reduced pressure at 80 to 90° C., 190 g of light brown to grayish white viscous liquid was obtained.

66.5 g out of the obtained light brown to grayish white viscous liquid was prepared in another reactor, treatment was performed for 30 minutes at 60 to 70° C. by adding 66.5 g of caprylyl methicone (FZ-3196 manufactured by Dow Corning Toray Co., Ltd., average composition formula: $MD^{R*12}_1M$, 2.9 cst (25° C.)) and an aqueous solution of 0.010 g of sodium hydrogensulfate monohydrate/1.0 g of ion exchanged water, and furthermore, after reducing the pressure to less than or equal to 10 Torr, the generated odor component and water were removed. Thereafter, 1.0 g of ion exchanged water was again added, an operation in which decompression was performed in the same manner to remove the odor component and water was repeated two times (the last decompression operation was maintained at less than or equal to 5 Torr for 45 minutes at −60 to 70° C.), and thus, 132 g of a polyhydric alcohol derivative-modified silicone No. 5 (composition comprising a composition containing the polyhydric alcohol derivative-modified silicone No. 5 as a main component and caprylyl methicone (diluent)) was obtained as a white opaque liquid. Here, the weight (mass) ratio of the silicone composition to the diluent was 1:1.

The polyhydric alcohol derivative-modified silicone (liquid polyhydric alcohol derivative-modified crosslinked silicone) No. 5 obtained by Production Example 5 is indicated in the following average structural formula (schematic diagram).

[Chemical Formula 59]

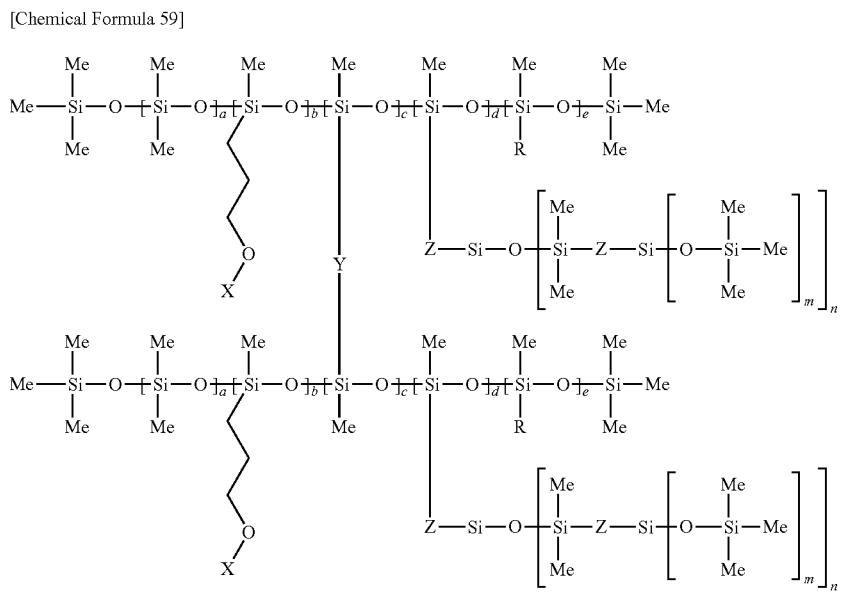

(wherein, Me=methyl group; within [ ]n, Z=—CH$_2$CH$_2$—; outside of [ ]n, Z=—C$_3$H$_6$—COO—C$_3$H$_6$—; R=—C$_{16}$H$_{33}$; Y=—(CH$_2$)$_6$—; a=42.9; b=0.8; c=1.2; d=0.3; e=4.4; m=3; n=3), and X=(C$_3$H$_6$O$_2$)$_2$H Production Example 6

Synthesis of Polyhydric Alcohol Derivative-Modified Silicone No. 6

110.3 g of methylhydrogenpolysiloxane expressed by the average composition formula: MD$_{330}$D$^H{}_{80}$M and 12.1 g of vinyl tris-trimethylsiloxy silane expressed by the average composition formula: CH$_2$=CH—Si(OSiMe$_3$)$_3$ were prepared in a reactor, and 0.25 g of IPA solution of platinum-1,3-divinyl-1,1,3,3-tetramethyldisiloxane complex (Pt concentration 0.4 wt. %) was added at 35° C. while stirring under a nitrogen stream. After the temperature rise caused by generated heat leveled off, 12.1 g of the vinyl tris-trimethylsiloxy silane (second addition) was added and the mixture was reacted in the same way. After the temperature rise caused by generated heat leveled off, 12.1 g of the vinyl tris-trimethylsiloxy silane (third addition) was added and the mixture was reacted in the same way. Then, 2 g of the reaction liquid was sampled, and it was confirmed with an alkali decomposition gas generation method that the reaction rate was not in error.

8.0 g of polyglycerinmonoallyl ether (average number of repetitions of glycerin unit=4.0), 0.02 g of natural vitamin E, and 60 g of IPA were added to the reaction liquid. Then, 0.25 g of the same platinum catalyst solution described above was added. After the temperature rise caused by generated heat leveled off, a reaction was performed for two hours at from 65 to 80° C. and, thereafter, the same method was used to confirm that the reaction rate was not in error.

15.1 g of hexadecene (a olefin purity=91.7%) was added to the reaction liquid at approximately 65° C. After the temperature rise caused by generated heat leveled off, 15.1 g of the hexadecene (second addition) was added and the mixture was reacted in the same way. After the temperature rise caused by generated heat leveled off, 15.2 g of the hexadecene (third addition) and 0.25 g of platinum catalyst solution were added, and a reaction was performed for three hours at from 65 to 80° C. When 2 g of the reaction liquid was sampled and confirmed with an alkali decomposition gas generation method, the reaction had been completed.

After adding 200 g of diluent capryryl methicone (SS-3408) and dissolving it by mixing, IPA and low-boiling components were removed by heating at a reduced pressure, and thus, 380 g of 50:50 (wt. ratio) mixture of a composition containing the polyhydric alcohol derivative-modified silicone expressed by the average composition formula: MD$_{330}$D$^{R*11}{}_{45}$D$^{R*32}{}_{30}$D$^{R*24}{}_5$M and capryryl methicone was obtained. This mixture was milky white uniform gummy at room temperature.

In the formula,
R*$^{11}$=—C$_{16}$H$_{33}$
R*$^{32}$=—C$_2$H$_4$Si(OSiMe$_3$)$_3$
R*$^{24}$=—C$_3$H$_6$O—(C$_3$H$_6$O$_2$)$_n$—H, n=4.0

200 g out of the obtained milky white uniform gummy mixture was prepared in another reactor, to which 60 g of IPA and an aqueous solution prepared by dissolving 0.21 g of sodium hydrogensulfate monohydrate in 20 g of purified water was added, and acid treatment was performed for one hour at 70 to 80° C. while stirring under a nitrogen stream. Thereafter, the IPA and low-boiling components were removed at 70° C. under reduced pressure, then the pressure was restored when water droplets in the system had disappeared (first acid treatment). Next, after 60 g of IPA and 20 g of water were added and treatment was performed for one hour in the same manner, the IPA and low-boiling components were removed, then the pressure was restored when water droplets in the system had disappeared (second acid treatment). The same operation was repeated again (third acid treatment), and thus, 194 g of polyhydric alcohol derivative-modified silicone No. 6 (composition comprising a composition containing the polyhydric alcohol derivative-modified silicone No. 6 as a main component and caprylyl methicone (diluent)) expressed by the average composition formula: MD$_{330}$D$^{R*11}{}_{45}$D$^{R*32}{}_{30}$D$^{R*24}{}_5$M was obtained as a milky white uniform gummy liquid. Here, the weight (mass) ratio of the silicone composition to the diluent was 1:1. In this formula, R*$^{11}$, R*$^{32}$, R*$^{24}$ are as described above.

Production Example 7

Synthesis of Polyhydric Alcohol Derivative-Modified Silicone No. 7

124.1 g of methylhydrogenpolysiloxane expressed by the average composition formula: MD$_{45}$D$^H{}_2$M, 60.2 g of 3-methacryloxy propyl(tris(trimethylsiloxy)silylethyl dimethylsiloxy)silane expressed by the following average composition formula:

[Chemical Formula 60]

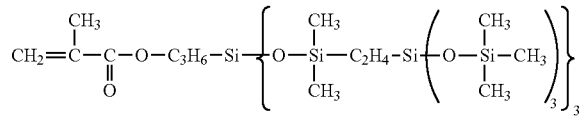

15.9 g of polyglycerinmonoallyl ether, and 193 g of IPA were prepared in a reactor, and heated to 30° C. while stirring under a nitrogen stream. 0.117 mL of IPA solution of platinum-1,3-divinyl-1,1,3,3-tetramethyldisiloxane complex (Pt concentration 4.5 wt. %) was added, and a reaction was performed for seven hours at 75 to 90° C.

When 2 g of the reaction liquid was sampled to confirm with an alkali decomposition gas generation method, the reaction was found to have been completed, indicating that a polyhydric alcohol derivative-modified silicone expressed by the average composition formula: MD$_{45}$D$^{R*31}{}_1$D$^{R*24}{}_1$M was found to have been generated. In addition, by heating the reaction liquid at a reduced pressure and removing low-boiling components, 195 g of milky white uniform viscous liquid was obtained. In this formula, R*$^{31}$ and R*$^{24}$ are as described below.

[Chemical Formula 61]

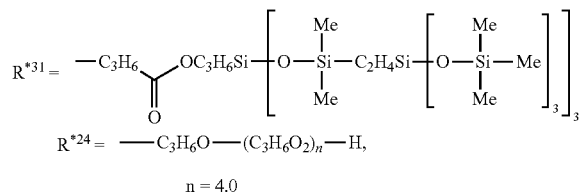

Next, 160 g out of the obtained milky white uniform viscous liquid was prepared in another reactor, to which an aqueous solution prepared by dissolving 0.024 g of sodium hydrogensulfate monohydrate in 2.4 g of purified water was added, and acid treatment was performed for 30 minutes at 70 to 80° C. while stirring under a nitrogen stream. Thereafter, the low-boiling components was removed at 70° C. under reduced pressure, then the pressure was restored when water droplets in the system had disappeared (first acid treatment). Next, after 2.4 g of water was added and treatment was performed for 30 minutes in the same manner, the low-boiling components was removed, then the pressure was restored when water droplets in the system had disappeared (second acid treatment). The same operation was repeated again (third acid treatment), and thus, 156 g of a composition consisting the polyhydric alcohol derivative-modified silicone No. 7 expressed by the average composition formula: $MD_{45}D^{R*31}{}_{1}D^{R*24}{}_{1}M$ was obtained as a milky white viscous liquid. Here, $R^{*31}$ and $R^{*24}$ are as described above.

Production Example 8

Synthesis of Polyhydric Alcohol Derivative-Modified Silicone No. 8

879.5 g of methylhydrogenpolysiloxane represented by the average composition formula: $MD_{44.7}D^{H}{}_{2}M$, 131.0 g of high-purity chain diglycerinmonoallyl ether, 0.10 g of natural vitamin E, and 703 g of IPA were prepared in a reactor, and heated. According to a conventional method, the IPA solution of platinum-1,3-divinyl-1,1,3,3-tetramethyldisiloxane complex (Pt concentration 4.5 wt. %) was added, and a reaction was performed at 60 to 85° C. When the reaction liquid was sampled to confirm with an alkali decomposition gas generation method, the reaction was found to be almost completed, indicating that a polyhydric alcohol derivative-modified silicone expressed by the average composition formula: $MD_{44.7}D^{R*22}{}_{2}M$ was found to have been generated. In addition, by heating the reaction liquid at a reduced pressure and removing low-boiling components, a dark brown liquid was obtained. In this formula, $R^{*22}$ is as described below.

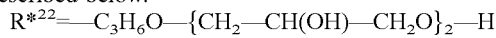
$R^{*22}$=—$C_3H_6O$—{$CH_2$—$CH(OH)$—$CH_2O$}$_2$—H

Next, after the low-boiling components were removed under a reduced pressure at 50 to 95° C., treatment was performed for 25 minutes at 65 to 85° C. by adding an aqueous solution comprising 0.15 g of sodium hydrogensulfate monohydrate/15 g of ion exchanged water, and furthermore, after reducing the pressure to less than or equal to 10 Torr, the generated odor component and water were removed. Thereafter, 15 g of ion exchanged water was again added, an operation in which the odor component and water is removed by the treatment and decompression under the almost similar conditions was repeated two times (the last decompression operation was maintained for one hour), and thus, 1000 g of a composition containing the polyhydric alcohol derivative-modified silicone No. 8 expressed by the average composition formula: $MD_{44.7}D^{R*22}{}_{2}M$ was obtained as an ash-brown opaque viscous liquid. Here, $R^{*22}$ is as described above.

In addition, the mass ratio of a main component of the composition thus obtained (polyhydric alcohol derivative-modified silicon No. 8) and an impurity glycerin derivative that is the cause of turbidity was estimated. In the Production Example 8, the molar number of a C=C group of 131.0 g was formulated to become 1.30 times of the molar number of a $D^H$ group that is to react therewith. Therefore, the amount consumed by hydrosilylation out of 131.0 g used was calculated to be 131.0 g/1.30=100.8 g, and the excess was calculated to be 30.2 g. Thus, the mass of the modified silicone that is the main component was calculated to be 980.3 g according to the molar number of the starting material methylhydrogenpolysiloxane and the molecular weight and the added molar number of each modifier. From the above, the abundance ratio of the main component and the turbid component was found to be 980.3 g:30.2 g=97.0: 3.0 (impurities were equivalent to 3.1% of the main component). It is understood that in this case, hydrophilic impurities that were in excess of 3% remained in the polyhydric alcohol derivative-modified silicone composition, and the hydrophilic impurities resulted in intense turbidity.

Production Example 9

Synthesis of Polyhydric Alcohol Derivative-Modified Silicone No. 9

951.4 g of methylhydrogenpolysiloxane expressed by the average composition formula: $^{H}MD_{187}M^{H}$ and 19.8 g of allyl glycidyl ether were prepared in a reactor, and heated to 65° C. while stirring under a nitrogen stream. 0.07 mL of IPA solution of platinum-1,3-divinyl-1,1,3,3-tetramethyldisiloxane complex (Pt concentration 4.5 wt. %) was added, and a reaction was performed for three hours at 65 to 85° C.

When 2 g of the reaction liquid was sampled to confirm with an alkali decomposition gas generation method, the reaction was found to have been completed, indicating that a modified silicone having an epoxy group (glycidyl oxypropyl group) at both terminals of the molecular chain was found to have been generated. In addition, by heating the reaction liquid under reduced pressure and removing the remaining allyl glycidyl ether at 160° C., a light yellow uniform liquid was obtained.

Next, after cooling the contents in the reactor down to lower than or equal to 100° C., 33.9 g of 85 wt. % of diisopropanolamine (DIPA) aqueous solution was added, and a reaction was performed for 4.5 hours while performing dehydration at 100 to 110° C. under reduced pressure of less than or equal to 10 Torr. Thus, 991 g of composition containing a polyhydric alcohol derivative-modified silicone No. 9 expressed by the average composition formula: $^{R*25}MD_{187}M^{R*25}$ was obtained as a pale yellow liquid (while most of the portion is transparent, a small white turbid haze portion was also included). Here, $R^{*25}$ is as described below.

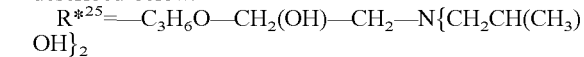
$R^{*25}$=—$C_3H_6O$—$CH_2(OH)$—$CH_2$—$N${$CH_2CH(CH_3)$ $OH$}$_2$

In the Production Example 9, 1.5 times moles of diisopropanolamine (DIPA) were formulated with respect to an epoxy group of the modified silicone having an epoxy group that is an intermediate. When back calculating on the basis of this, the abundance ratio of the polyhydric alcohol derivative-modified silicone No. 9 as the main component and the excess DIPA can be estimated to be 99.0:1.0.

Comparative Example 1

Comparative Composition RE-1 Containing Polyhydric Alcohol Derivative-Modified Silicone No. 1

The light brown opaque viscous liquid obtained in Production Example 1 (composition containing the polyhydric alcohol derivative-modified silicone No. 1 as the main component) was used as a sample without further changes.

Comparative Example 1-2

Comparative Composition RE-1(-2) Containing Polyhydric Alcohol Derivative-Modified Silicone No. 1

200 g of the light brown opaque viscous liquid obtained in Production Example 1 (composition containing the polyhydric alcohol derivative-modified silicone No. 1 as the main component) was prepared in a reactor, thereto was added 18.0 g of an aqueous solution prepared by dissolving 6.0 g of trehalose dihydrate (crystalline powder, white) in 12.0 g of purified water, and the mixture was stirred for 50 minutes at 50° C. Next, when dewatering was carried out for 40 minutes by decompressing until the group was less than or equal to 10 Torr, water droplets disappeared from the group. Pressure was recovered during cooling to 40° C. while stirring. The contents of the reactor was an opaque liquid having strong white turbidness.

An edge of ADVANTEC No. 424 filter paper (retained particle diameter: 4 μm) with a diameter of 110 mm (slightly larger than the inner diameter of the pressure filter) was folded evenly on a plate of the pressure filter, and was tightly spread, then the filter was set as a base. At this time, the filter stands vertically, a receiver is installed below a filtrate outlet having a narrow diameter below the position of the plate.

100 g of the white turbid dispersion was collected in a cup, thereto was added 10 g of diatomaceous earth powder with a median particle size 30.6 μm, and the mixture was stirred and mixed well with a spatula to form a slurry state. The slurry was poured onto the filter paper set in the pressure filter, then nitrogen pressure was applied from an upper portion after covering the filter with a lid, thereby forming a filter layer composed mainly of diatomaceous earth powder with a median particle size of 30.6 μm.

Next, when the remaining portion of the white turbid dispersion and the filtrate collected during filter layer formation were poured onto the filter again, and nitrogen pressure was applied from the upper portion after covering the filter with a lid, 177 g of an opaque liquid having strong white turbidness was obtained. The turbidity of the appearance was further increased in comparison to prior to treatment (that is, a sample of Comparative Example 1). The result was used as the sample of comparative composition RE-1(-2).

Comparative Example 2

Preparation of Comparative Composition RE-2 Containing Polyhydric Alcohol Derivative-Modified Silicone No. 2

The grayish brown opaque viscous liquid obtained in Production Example 2 (composition containing the polyhydric alcohol derivative-modified silicone No. 2 as the main component) was used as a sample without further changes.

Comparative Example 3

Preparation of Comparative Composition RE-3 Containing Polyhydric Alcohol Derivative-Modified Silicone No. 3

The light brown opaque viscous liquid obtained in Production Example 3 (composition containing the polyhydric alcohol derivative-modified silicone No. 3 as the main component) was used as a sample without further changes.

Comparative Example 4

Preparation of Comparative Composition RE-4 Containing Polyhydric Alcohol Derivative-Modified Silicone No. 4

The grayish brown opaque viscous liquid obtained in Production Example 4 (composition containing the polyhydric alcohol derivative-modified silicone No. 4 as the main component) was used as a sample without further changes.

Comparative Example 5

Preparation of Comparative Composition RE-5 Containing Polyhydric Alcohol Derivative-Modified Silicone No. 5

The white opaque liquid obtained in Production Example 5 (composition comprising a composition containing the polyhydric alcohol derivative-modified silicone No. 5 as the main component, and caprylyl methicone (diluent)) was used as a sample without further changes.

Comparative Example 6

Preparation of Comparative Composition RE-6 Containing Polyhydric Alcohol Derivative-Modified Silicone No. 6

The milky white uniform gummy liquid obtained in Production Example 6 (composition comprising a composition containing the polyhydric alcohol derivative-modified silicone No. 6 as the main component, and caprylyl methicone (diluent)) was used as a sample without further changes.

Comparative Example 7

Preparation of Comparative Composition RE-7 Containing Polyhydric Alcohol Derivative-Modified Silicone No. 7

The milky white viscous liquid obtained in Production Example 7 (composition containing the polyhydric alcohol derivative-modified silicone No. 7 as the main component) was used as a sample without further changes.

Comparative Example 8

Preparation of Comparative Composition RE-8 Containing Polyhydric Alcohol Derivative-Modified Silicone No. 8

The ash-brown opaque viscous liquid obtained in Production Example 8 (composition containing the polyhydric alcohol derivative-modified silicone No. 8 as the main component) was used as a sample without further changes.

Comparative Example 8-2

Preparation of Comparative Composition RE-8(-2) Containing Polyhydric Alcohol Derivative-Modified Silicone No. 8

A glass fiber filter paper GC-90 with a diameter of 90 mm (retained particle diameter: 0.5 μm) was set in a stainless steel holder with tank ADVANTEC KST-90, and a tank unit and a base plate (O-ring, filter paper, part placing a support screen) were fastened by a dedicated bolt, washer, and nut and fixed such that there was no leakage. Thereby, there was a structure in which the entire edge of the filter paper was fastened vertically and leakage was prevented.

150 g of the ash-brown opaque viscous liquid obtained in Production Example 8 (composition containing the polyhydric alcohol derivative-modified silicone No. 8 as the main component) was introduced from an opening at an upper part of the tank, then the opening was closed using a tank cap, and filtration was performed by applying nitrogen pressure at 0.4 MPa. As a result, 144 g of an ash-brown opaque viscous liquid was obtained, but turbidity of the appearance was not reduced at all in comparison to prior to filtration. The result was used as the sample of comparative composition RE-8(-2).

Noted that, when the stainless steel holder with tank was disassembled after filtration ends and the presence or absence of leakage from the base plate was confirmed, it was found that there was no leakage and the whole amount of the filtrate passed through only the filter paper center portion.

Comparative Example 9

Preparation of Comparative Composition RE-9 Containing Polyhydric Alcohol Derivative-Modified Silicone No. 9

The pale yellow liquid obtained in Production Example 9 (composition containing the polyhydric alcohol derivative-modified silicone No. 9 as the main component) in which most of the portion was transparent, but a small white turbid haze portion was also included was homogenized by shaking, and used as a sample without further changes.

Example 1

Preparation of Liquid High-Purity Polyhydric Alcohol Derivative-Modified Silicone No. 1

150 g of the light brown opaque viscous liquid obtained in Production Example 1 (composition containing the polyhydric alcohol derivative-modified silicone No. 1 as the main component), 151 g toluene, and 4.5 g of trehalose dihydrate (crystalline powder, white) were prepared in a reactor, and the mixture was stirred for 40 minutes at 50 to 60° C., and thus, a light brown to white turbid dispersion was obtained. The mixture was cooled to room temperature.

An edge of ADVANTEC No. 424 filter paper (retained particle diameter: 4 µm) with a diameter of 110 mm (slightly larger than the inner diameter of the pressure filter) was folded evenly on a plate of the pressure filter, and was tightly spread, then the filter was set as a base. At this time, the filter stands vertically, a receiver is installed below a filtrate outlet having a narrow diameter below the position of the plate.

100 g of the white turbid dispersion was collected in a cup, thereto was added 10 g of diatomaceous earth powder with a median particle size 30.6 µm, and the mixture was stirred and mixed well with a spatula to form a slurry state. The slurry was poured onto the filter paper set in the pressure filter, then nitrogen pressure of 0.02 MPa was applied from an upper portion after covering the filter with a lid, thereby forming a filter layer composed mainly of diatomaceous earth powder with a median particle size of 30.6 µm.

Next, when the remaining portion of the light brown to white turbid dispersion and filtrate collected during filter layer formation were poured onto the filter again, and nitrogen pressure was applied from the upper portion after covering the filter with a lid, surprisingly, the whole amount of the filtrate was translucent uniform liquid with light yellow color, and the weight was 228 g.

Due to the filtrate being prepared in a clean flask and the toluene under nitrogen gas stream being removed under reduced pressure from 80 to 100° C., a liquid high purity polyhydric alcohol derivative-modified silicone No. 1 expressed by the average composition formula: $MD_{37}D^{R*11}{}_{8.7}D^{R*21}{}_{3}D^{R*32}{}_{1}M$ was obtained as light yellowish-brown translucent viscous liquid. (Collected amount of 132 g) In the formula, $R^{*11}$, $R^{*21}$, and $R^{*32}$ are as described below.

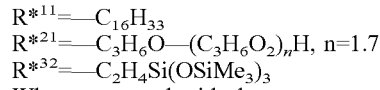

When compared with the appearance before performing the treatment shown in Example 1, the transparency had improved by far, but when compared with the samples obtained in the following other examples, the haze was still found to be large.

Example 1-2

Preparation of Liquid High-Purity Polyhydric Alcohol Derivative-Modified Silicone No. 1

When 150 g of the light brown opaque viscous liquid obtained in Production Example 1 (composition containing the polyhydric alcohol derivative-modified silicone No. 1 as the main component), 156 g of n-heptane, and 4.5 g of guanine (pale yellowish white powder) were prepared in a reactor, and the mixture was stirred, the mixture was a whitish yellow turbid liquid. After heating to 45 to 60° C. and stirring for 110 minutes, the mixture was cooled to room temperature under stirring.

In the same manner as the case of Example 1, the pressure filter, plate, filter paper, and receiver were set.

100 g of the turbid liquid obtained by the treatment described above was collected in a cup, thereto was added 5 g of diatomaceous earth fine powder with a median particle size of 10.9 µm, and the mixture was stirred and mixed well with a spatula to form a slurry state. The slurry was poured onto a filter paper set in the pressure filter, then nitrogen pressure of 0.1 to 0.2 MPa was applied from an upper portion after covering the filter with a lid, thereby forming a filter layer composed mainly of diatomaceous earth fine powder with a median particle size of 10.9 µm.

Next, when the remaining portion of the turbid liquid (containing pale yellow white powder) and filtrate collected during filter layer formation were poured onto the filter layer again, and nitrogen pressure of 0.2 to 0.3 MPa was applied from the upper portion after covering the filter with a lid, surprisingly, the whole amount of the filtrate was fairly transparent liquid with pale yellow color.

Due to the filtrate being prepared in a clean flask and the n-heptane under nitrogen gas stream being removed under reduced pressure from 68 to 100° C., a liquid high purity polyhydric alcohol derivative-modified silicone No. 1 expressed by the average composition formula: $MD_{37}D^{R*11}{}_{8.7}D^{R*21}{}_{3}D^{R*32}{}_{1}M$ was obtained as pale yellow translucent uniform viscous liquid. (Collected amount of 140 g) In the formula, $R^{*11}$, $R^{*21}$, and $R^{*32}$ are as described earlier.

Example 2

Preparation of Liquid High-Purity Polyhydric Alcohol Derivative-Modified Silicone No. 2

When 150 g of the grayish brown opaque viscous liquid obtained in Production Example 2 (composition containing the polyhydric alcohol derivative-modified silicone No. 2 as the main component), 152 g of toluene, and 4.5 g of trehalose dihydrate (crystalline powder, white) were prepared in a reactor, and the mixture was heated to 50 to 60° C. and stirred for 55 minutes, then a white crystal block was found to be in a state of moving around in light brown turbid liquid. (Surprisingly, the size of the solid particles grew up to Japanese style breadcrumbs) The mixture was cooled to lower than or equal to 40° C. while stirring and then stirring was stopped. When observed the next day, it was found to have separated into a supernatant liquid and crystal precipitate.

In the same manner as the case of Example 1, the pressure filter, plate, filter paper, and receiver were set.

100 g of the supernatant liquid obtained by the treatment described above was collected in a cup, thereto was added 5 g of diatomaceous earth fine powder with a median particle size of 10.9 µm, and the mixture was stirred and mixed well with a spatula to form a slurry state. The slurry was poured onto the filter paper set in the pressure filter, then nitrogen pressure of 0.2 MPa was applied from an upper portion after covering the filter with a lid, thereby forming a filter layer composed mainly of diatomaceous earth fine powder with a median particle size of 10.9 µm.

Next, when the remaining portion of the supernatant liquid as well as the crystal precipitate and filtrate collected during filter layer formation were poured onto the filter layer again, and nitrogen pressure of 0.2 MPa was applied from the upper portion after covering the filter with a lid, surprisingly, the whole amount of the filtrate was transparent uniform liquid with light brown color, and the weight was 267 g.

Due to the filtrate being prepared in a clean flask and the toluene under nitrogen gas stream being removed under reduced pressure from 80 to 100° C., a liquid high purity polyhydric alcohol derivative-modified silicone No. 2 expressed by the average composition formula: $MD_{37}D^{R*11}{}_{8.7}D^{R*22}{}_3D^{R*32}{}_1M$ was obtained as light yellowish-brown translucent to fairly transparent uniform viscous liquid. (Collected amount of 138 g) In the formula, $R^{*11}$, $R^{*22}$, and $R^{*32}$ are as described below.

$R^{*11}=\!\!-\!\!C_{16}H_{33}$
$R^{*22}=\!\!-\!\!C_3H_6O\!\!-\!\!\{CH_2\!\!-\!\!CH(OH)\!\!-\!\!CH_2O\}_2\!\!-\!\!H$
$R^{*32}=\!\!-\!\!C_2H_4Si(OSiMe_3)_3$

Example 2-2

Preparation of Liquid High-Purity Polyhydric Alcohol Derivative-Modified Silicone No. 2

150 g of the grayish brown opaque viscous liquid obtained in Production Example 2 (composition containing the polyhydric alcohol derivative-modified silicone No. 2 as the main component), 151 g of n-heptane, and 4.5 g of gallic acid monohydrate (crystalline fine powder, whitish yellow) were prepared in a reactor, and the mixture was heated to 50 to 60° C. and stirred for 40 minutes, following which the mixture was cooled to room temperature.

In the same manner as the case of Example 2, the pressure filter, plate, filter paper, and receiver were set, and with the same technique, a filter layer was formed mainly from 5 g of diatomaceous earth powder with a median particle size of 10.9 µm, and the turbid liquid mixture obtained by the treatment described earlier was passed through the filter layer to obtain 269 g of translucent uniform filtrate.

Next, with the same technique as in Example 2, n-heptane was distilled off from the filtrate, and the mixture was again passed through the filter layer formed of 5 g of the diatomaceous earth powder with a median particle size of 10.9 µm to obtain a light yellowish-brown color transparent uniform liquid mixture of the liquid high-purity polyhydric alcohol derivative-modified silicone No. 2 expressed by the average composition formula: $MD_{37}D^{R*11}{}_{8.7}D^{R*22}{}_3D^{R*32}{}_1M$. (Collected amount of 115 g) In the formula, $R^{*11}$, $R^{*22}$, and $R^{*32}$ are as described earlier.

Example 3

Preparation of Liquid High-Purity Polyhydric Alcohol Derivative-Modified Silicone No. 3

150 g of the light brown opaque viscous liquid obtained in Production Example 3 (composition containing the polyhydric alcohol derivative-modified silicone No. 3 as the main component), 150 g of toluene, and 4.5 g of glycine (white powdered crystal) were prepared in a reactor, and the mixture was heated to 45 to 65° C. and stirred for 50 minutes, following which the mixture was cooled to room temperature.

In the same manner as the case of Example 1, the pressure filter, plate, filter paper, and receiver were set.

100 g of the turbid liquid obtained by the treatment described above was collected in a cup, thereto was added 3 g of diatomaceous earth fine powder with a median particle size of 10.9 µm, and the mixture was stirred and mixed well with a spatula to form a slurry state. The slurry was poured onto the filter paper set in the pressure filter, then nitrogen pressure of 0.06 MPa was applied from an upper portion after covering the filter with a lid, thereby forming a filter layer composed mainly of diatomaceous earth fine powder with a median particle size of 10.9 µm.

Next, when the remaining portion of the turbid liquid (containing white powder) and filtrate collected during filter layer formation were poured onto the filter layer again, and nitrogen pressure of 0.06 MPa was applied from the upper portion after covering the filter with a lid, surprisingly, the whole amount of the obtained filtrate was transparent uniform liquid with pale to light yellow color.

Due to the filtrate being prepared in a clean flask and toluene under nitrogen gas stream being removed under reduced pressure from 80 to 100° C., a liquid high-purity polyhydric alcohol derivative-modified silicone No. 3 expressed by the average composition formula: $MD_{43.4}D^{R*11}{}_{5.3}D^{R*21}{}_2D^{R*32}{}_{0.1}M$ was obtained as light yellow almost transparent uniform viscous liquid. (Collected amount of 140 g) In the formula, $R^{*11}$, $R^{*21}$, and $R^{*32}$ are as described below.

$R^{*11}=\!\!-\!\!C_{16}H_{33}$
$R^{*21}=\!\!-\!\!C_3H_6O\!\!-\!\!(C_3H_6O_2)_n\!\!-\!\!H$, n=1.7
$R^{*32}=\!\!-\!\!C_2H_4Si(OSiMe_3)_3$

Example 3-2

Preparation of Liquid High-Purity Polyhydric Alcohol Derivative-Modified Silicone No. 3

When 150 g of the light brown opaque viscous liquid obtained in Production Example 3 (composition containing the polyhydric alcohol derivative-modified silicone No. 3 as the main component), 150 g of toluene, and 4.5 g of anhydrous sodium sulfate (white powdered crystal) were prepared in a reactor, and the mixture was heated to 45 to 60° C. and stirred for 40 minutes, then the mixture was grayish white turbid liquid. Stirring was stopped and the mixture was cooled to room temperature.

In the same manner as the case of Example 3, the pressure filter, plate, filter paper, and receiver were set, and with the same technique, a filter layer was formed mainly from 3 g of diatomaceous earth powder with a median particle size of 10.9 µm, and the turbid liquid mixture obtained by the treatment described earlier was passed through the filter layer to obtain light yellow transparent uniform filtrate.

Next, by removing toluene from the filtrate with the same technique as in Example 3, the liquid high-purity polyhydric alcohol derivative-modified silicone No. 3 expressed by the average composition formula: $MD_{43.4}D^{R*11}{}_{5.3}D^{R*21}{}_2D^{R*32}{}_{0.1}M$ was obtained as light yellow almost transparent uniform viscous liquid. (Collected amount of 141 g) In the formula, $R^{*11}$, $R^{*21}$, and $R^{*32}$ are as described earlier.

Example 3-3

Preparation of Liquid High-Purity Polyhydric Alcohol Derivative-Modified Silicone No. 3

134 g of the light brown opaque viscous liquid obtained in Production Example 3 (composition containing the polyhydric alcohol derivative-modified silicone No. 3 as the main component), 134 g of toluene, and 4 g of diatomaceous earth powder with a median particle size of 10.9 µm were prepared in a reactor, and the mixture was heated to 45 to 60° C. and stirred for 40 minutes, following which the mixture was cooled to room temperature.

In the same manner as the case of Example 1, the pressure filter, plate, filter paper, and receiver were set.

The entire amount of turbid liquid obtained by the treatment described earlier was poured onto the filter paper set in the pressure filter, then nitrogen pressure of 0.02 MPa was applied from an upper portion after covering the filter with a lid, thereby forming a filter layer composed mainly of diatomaceous earth fine powder with a median particle size of 10.9 μm. Next, when the filtrate collected during filter layer formation was poured onto the filter layer again, and passed therethrough in the same manner, surprisingly, the whole amount of the obtained filtrate was almost transparent uniform liquid with pale yellow color.

Next, by removing toluene from the filtrate with the same technique as in Example 3, the liquid high-purity polyhydric alcohol derivative-modified silicone No. 3 expressed by the average composition formula: $MD_{43.4}D^{R*11}{}_{5.3}D^{R*21}{}_2D^{R*32}{}_{0.1}M$ was obtained as pale yellow fairly transparent uniform viscous liquid. (Collected amount of 123 g) In the formula, $R^{*11}$, $R^{*21}$, and $R^{*32}$ are as described earlier.

Example 4

Preparation of Liquid High-Purity Polyhydric Alcohol Derivative-Modified Silicone No. 4

150 g of the grayish brown opaque viscous liquid obtained in Production Example 4 (composition containing the polyhydric alcohol derivative-modified silicone No. 4 as the main component), 149 g of toluene, and 4.5 g of polyvinyl alcohol (degree of polymerization: 1500, white granular powder) were prepared in the reactor, the mixture was heated to 45 to 60° C. and stirred for 55 minutes, following which the mixture was cooled to room temperature.

In the same manner as the case of Example 1, the pressure filter, plate, filter paper, and receiver were set.

100 g of the turbid liquid obtained by the treatment described above was collected in a cup, thereto was added 5.5 g of diatomaceous earth fine powder with a median particle size of 10.9 μm, and the mixture was stirred and mixed well with a spatula to form a slurry state. The slurry was poured onto the filter paper set in the pressure filter, then nitrogen pressure of 0.03 to 0.1 MPa was applied from an upper portion after covering the filter with a lid, thereby forming a filter layer composed mainly of diatomaceous earth fine powder with a median particle size of 10.9 μm.

Next, when the remaining portion of the turbid liquid (containing white precipitate) and filtrate collected during filter layer formation were poured onto the filter layer again, and nitrogen pressure of 0.03 to 0.1 MPa was applied from the upper portion after covering the filter with a lid, surprisingly, the whole amount of the obtained filtrate was transparent uniform liquid with light brown color.

Due to the filtrate being prepared in a clean flask and toluene under nitrogen gas stream being removed under reduced pressure from 80 to 100° C., a liquid high-purity polyhydric alcohol derivative-modified silicone No. 4 expressed by the average composition formula: $MD_{43.4}D^{R*11}{}_{5.3}D^{R*22}{}_2D^{R*32}{}_{0.1}M$ was obtained as pale yellow almost transparent to translucent uniform viscous liquid. (Collected amount of 140 g) In the formula, $R^{*11}$, $R^{*22}$, and $R^{*32}$ are as described below.

$R^{*11}$=—$C_{16}H_{33}$
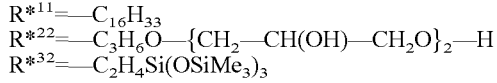
$R^{*32}$=—$C_2H_4Si(OSiMe_3)_3$

Example 4-2

Preparation of Liquid High-Purity Polyhydric Alcohol Derivative-Modified Silicone No. 4

150 g of the grayish brown opaque viscous liquid obtained in Production Example 4 (composition containing the polyhydric alcohol derivative-modified silicone No. 4 as the main component), 165 g of toluene, and 4.5 g of malonic acid (white granular powder) were prepared in a reactor, and the mixture was heated to 50 to 70° C. and stirred for one hour, following which the mixture was cooled to room temperature.

In the same manner as the case of Example 4, the pressure filter, plate, filter paper, and receiver were set, and with the same technique, a filter layer was formed mainly from 5.3 g of diatomaceous earth powder with a median particle size of 10.9 μm, and the turbid liquid mixture obtained by the treatment described earlier was passed through the filter layer to obtain pale yellow transparent uniform filtrate.

Next, by removing toluene from the filtrate with the same technique as in Example 4, the liquid high-purity polyhydric alcohol derivative-modified silicone No. 4 expressed by the average composition formula: $MD_{43.4}D^{R*11}{}_{5.3}D^{R*22}{}_2D^{R*32}{}_{0.1}M$ was obtained as light yellow almost transparent uniform viscous liquid. (Collected amount of 142 g) In the formula, $R^{*11}$, $R^{*22}$, and $R^{*32}$ are as described earlier.

Example 4-3

Preparation of Liquid High-Purity Polyhydric Alcohol Derivative-Modified Silicone No. 4

150 g of the grayish brown opaque viscous liquid obtained in Production Example 4 (composition containing the polyhydric alcohol derivative-modified silicone No. 4 as the main component), 150 g of toluene, and 4.5 g of trisodium citrate dihydrate (colorless granular crystal) were prepared in a reactor, and the mixture was heated to 50 to 65° C. and stirred for 40 minutes, following which the mixture was cooled to room temperature.

In the same manner as the case of Example 4, the pressure filter, plate, filter paper, and receiver were set, and with the same technique, a filter layer was formed mainly from 5 g of diatomaceous earth powder with a median particle size of 10.9 μm, and the turbid liquid mixture obtained by the treatment described earlier was passed through the filter layer to obtain light brown transparent uniform filtrate.

Next, by removing toluene from the filtrate with the same technique as in Example 4, the liquid high-purity polyhydric alcohol derivative-modified silicone No. 4 expressed by the average composition formula: $MD_{43.4}D^{R*11}{}_{5.3}D^{R*22}{}_2D^{R*32}{}_{0.1}M$ was obtained as light yellow almost transparent uniform viscous liquid. (Collected amount of 140 g) In the formula, $R^{*11}$, $R^{*22}$, and $R^{*32}$ are as described earlier.

Following this, when the filter layer of the diatomaceous earth was observed, it was found that the trisodium citrate which was in the shape of almost 0.5-mm rectangular crystals before use had coagulated to become large masses with a diameter of approximately a few mm, and had remained behind. From the above, it is understood that the hydrophilic impurities (in this case, mainly diglycerin), which is the substance causing turbidity, is separated after integrating with trisodium citrate.

Example 5

Preparation of Composition Containing Liquid High-Purity Polyhydric Alcohol Derivative-Modified Silicone No. 5

126 g of the white opaque liquid obtained in Production Example 5 (composition comprising a composition containing the polyhydric alcohol derivative-modified silicone No. 5 as the main component, and caprylyl methicone (diluent)) and 1.23 g of diatomaceous earth powder with a median particle size of 10.9 μm were prepared, and the mixture was stirred and mixed well with a spatula to form a slurry state.

In the same manner as the case of Example 1 (however, here, the pressure filter and filter paper were changed to a small type with an internal diameter or diameter of 95 mm), after setting the pressure filter, plate, filter paper, and receiver, the entire amount of the above-described slurry was poured onto the filter paper set in the pressure filter, the filter was covered with a lid, and nitrogen pressure of 0.3 MPa was applied from an upper portion, thereby forming a filter layer composed mainly of diatomaceous earth fine powder with a median particle size of 10.9 µm. Next, the filtrate collected during filter layer formation was poured onto the filter layer again, and passed therethrough in the same manner, and thus, "composition containing the liquid high-purity polyhydric alcohol derivative-modified silicone No. 5 indicated in the following average structural formula (schematic diagram) and caprylyl methicone (diluent)" (weight (mass) ratio of the above silicone No. 5 to the diluent was 1:1) was obtained as fairly transparent to translucent uniform liquid. (Collected amount of 112 g)

3 g of diatomaceous earth fine powder with a median particle size of 10.9 µm, and the mixture was stirred and mixed well with a spatula to form a slurry state. The slurry was poured onto a filter paper set in the pressure filter, then nitrogen pressure of 0.1 to 0.2 MPa was applied from an upper portion after covering the filter with a lid, thereby forming a filter layer composed mainly of diatomaceous earth fine powder with a median particle size of 10.9 µm.

Next, when the remaining portion of the turbid liquid (containing white precipitate) and filtrate collected during filter layer formation were poured onto the filter layer again, and nitrogen pressure of 0.05 to 0.1 MPa was applied from the upper portion after covering the filter with a lid, surprisingly, the whole amount of the obtained filtrate was almost transparent uniform liquid with pale yellow color, and the weight was 248 g.

Next, with the same technique as in Example 1, toluene was removed from the filtrate, and thus, a composition comprising the liquid high-purity polyhydric alcohol deriva-

[Chemical Formula 62]

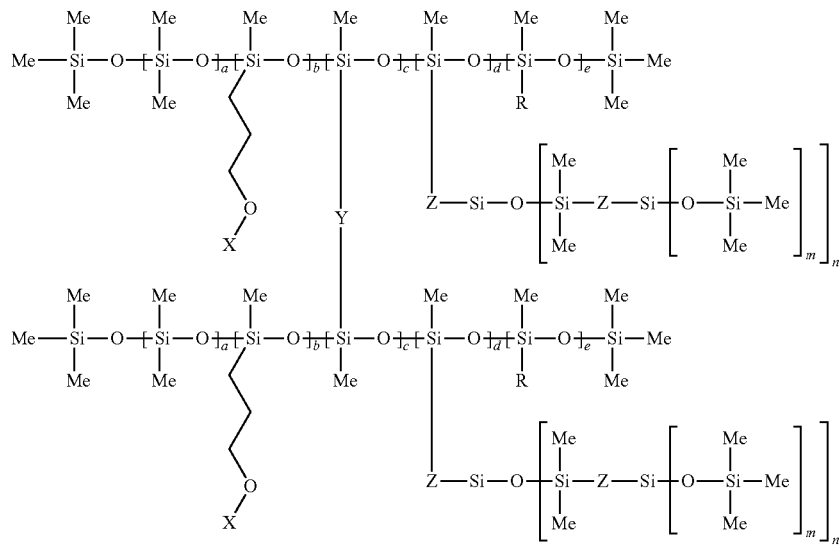

(wherein, Me=methyl group; within [ ]n, Z=—CH$_2$CH$_2$—; outside of [ ]n, Z=—C$_3$H$_6$—COO—C$_3$H$_6$—; R=—C$_{16}$H$_{33}$; Y=—(CH$_2$)$_6$—; a=42.9; b=1.1; c=1.3; d=0.3; e=4.0; m=3; n=3), and X=(C$_3$H$_6$O$_2$)$_2$H Example 6

Preparation of Composition Containing Liquid High-Purity Polyhydric Alcohol Derivative-Modified Silicone No. 6

130 g of the milky white uniform gummy liquid obtained in Production Example 6 (composition comprising a composition containing the polyhydric alcohol derivative-modified silicone No. 6 as the main component, and caprylyl methicone (diluent)), 142 g of toluene, and 2.0 g of carboxyvinyl polymer (also known as Carbomer, white fine powder) were prepared in a reactor, and the mixture was heated to 65 to 80° C. and stirred for 40 minutes, following which the mixture was cooled to room temperature.

In the same manner as the case of Example 5, the pressure filter, plate, filter paper, and receiver were set.

100 g of the turbid liquid obtained by the treatment described above was collected in a cup, thereto was added tive-modified silicone No. 6 expressed by the average composition formula: MD$_{330}$D$^{R*11}_{45}$D$^{R*32}_{30}$D$^{R*24}_{5}$M and caprylyl methicone was obtained as extremely viscous and uniform liquid with whitish yellow color. (Collected amount of 123 g) In the formula, R*$^{11}$, R*$^{32}$, and R*$^{24}$ are as described below.

R*$^{11}$=—C$_{16}$H$_{33}$
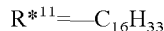
R*$^{32}$=—C$_2$H$_4$Si(OSiMe$_3$)$_3$
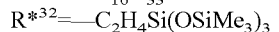
R*$^{24}$=—C$_3$H$_6$O—(C$_3$H$_6$O$_2$)$_n$—H, n=4.0
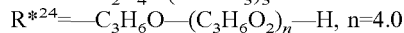

Example 7

Preparation of Composition Containing Liquid High-Purity Polyhydric Alcohol Derivative-Modified Silicone No. 7

150 g of the milky white viscous liquid obtained in Production Example 7 (composition containing the polyhydric alcohol derivative-modified silicone No. 7 as the main component), 120 g of toluene, and 4.5 g of polyvinyl alcohol (PVA, degree of polymerization: 1500, white granular powder) were prepared in a reactor, and the mixture was heated to 70 to 80° C. and stirred for 40 minutes, following which the mixture was cooled to room temperature.

In the same manner as the case of Example 6, the pressure filter, plate, filter paper, and receiver were set, and with the same technique, a filter layer was formed mainly from 3 g of diatomaceous earth powder with a median particle size of 10.9 µm, and the turbid liquid mixture obtained by the treatment described earlier was passed through the filter layer to obtain light yellow translucent uniform filtrate. Accordingly, this composition was considered as a composition comprising a liquid high-purity polyhydric alcohol derivative-modified silicone No. 7 expressed by the average composition formula: $MD_{45}D^{R*31}{}_1D^{R*24}{}_1M$ and toluene (diluent). The weight (mass) ratio of the modified silicone No. 7 to the diluent was 5:4, and in the formula, $R^{*31}$ and $R^{*24}$ are as described below.

[Chemical Formula 63]

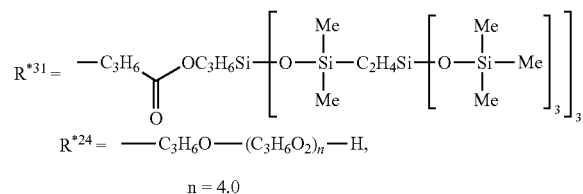

n = 4.0

Example 8

Preparation of Liquid High-Purity Polyhydric Alcohol Derivative-Modified Silicone No. 8

180 g of the ash-brown opaque viscous liquid obtained in Production Example 8 (composition containing the polyhydric alcohol derivative-modified silicone No. 8 as the main component), and 5.4 g of carboxyvinyl polymer (also known as Carbomer, white fine powder) were prepared in a reactor, and the mixture was heated to 60 to 85° C. and stirred for one hour. Thereafter, the mixture was cooled to 35° C. under stirring to obtain milky-turbid viscous liquid.

A glass fiber filter paper GC-90 with a diameter of 90 mm (retained particle diameter: 0.5 µm) was set in a stainless steel holder with tank ADVANTEC KST-90, and a tank unit and a base plate (O-ring, filter paper, part placing a support screen) were fastened by a dedicated bolt, washer, and nut and fixed such that there was no leakage. Thereby, there was a structure in which the entire edge of the filter paper was fastened vertically and leakage was prevented.

The turbid liquid obtained by the treatment described above was introduced from an opening at an upper part of the tank, then the opening was closed using a tank cap, and filtration was performed by applying nitrogen pressure at 0.4 MPa. Unlike the case of Comparative Example 8-2, brown almost transparent filtrate was obtained, but when there was 5 g of filtrate, clogging was generated and dropping of the amount of the filtrate was stopped. It is understood that this phenomenon was attributed to the fact that the hydrophilic impurities of liquid that is a turbid component was solidified by being incorporated into solid particles (here, Carbomer powder) capable of capturing the hydrophilic impurities of the present invention, and as a result, the solids were densely accumulated on the filter to cause the clogging. The liquid of the separated main component had an almost transparent appearance with turbidity substantially reduced from the initial turbidity. Accordingly, it was considered that an operating principle of the present invention was proven. In contrast to this, in Comparative Example 8-2, filtration was carried out under the completely same conditions as Example 8 except that the treatment by solid particles capable of capturing hydrophilic impurities in the present invention was not performed, but the turbidity was not reduced at all prior to and after the filtration. This means that the turbid component passes through the fine pores (less than 0.5 µm) of the filter without any clogging at all, and indicates that the turbid component in the composition exists as liquid.

Example 8-2

Preparation of Liquid High-Purity Polyhydric Alcohol Derivative-Modified Silicone No. 8

180 g of the ash-brown opaque viscous liquid obtained in Production Example 8 (composition containing the polyhydric alcohol derivative-modified silicone No. 8 as the main component), and 5.4 g of carboxyvinyl polymer (also known as Carbomer, white fine powder) were prepared in a reactor, and the mixture was heated to 60 to 85° C. and stirred for one hour. Thereafter, the mixture was cooled to 35° C. under stirring to obtain milky-turbid viscous liquid.

In the same manner as the case of Example 8, a glass fiber filter paper GC-90 with a diameter of 90 mm (retained particle diameter: 0.5 µm) was set in a stainless steel holder with tank ADVANTEC KST-90, and a tank unit and a base plate (O-ring, filter paper, part placing a support screen) were fastened by a dedicated bolt, washer, and nut and fixed such that there was no leakage.

5 g of diatomaceous earth powder with a median particle size of 46.5 µm was added to the milky-turbid viscous liquid obtained in the treatment described above with the object of suppressing clogging during filtration, and was stirred and mixed well with a spatula to form a slurry state.

The slurry was introduced from an opening at an upper part of the tank, then the opening was closed using a tank cap, and filtration was performed by applying nitrogen pressure at 0.4 MPa. As a result, a liquid high-purity polyhydric alcohol derivative-modified silicone No. 8 expressed by the average composition formula: $MD_{44.7}D^{R*22}{}_2M$ was obtained as dark brown almost transparent uniform viscous liquid. (Collected amount of 149 g) Here, in the above-described formula, $R^{*22}$ is as described below.

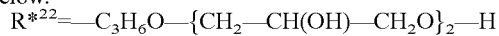

Example 8-3

Preparation of Liquid High-Purity Polyhydric Alcohol Derivative-Modified Silicone No. 8

157 g of the ash-brown opaque viscous liquid obtained in Production Example 8 (composition containing the polyhydric alcohol derivative-modified silicone No. 8 as the main component), 3.8 g of corn starch (white fine powder), and 0.9 g of carboxyvinyl polymer (also known as Carbomer, white fine powder) were prepared in a reactor, and the mixture was heated to 60 to 85° C. and stirred for one hour. Thereafter, the mixture was cooled to 35° C. under stirring to obtain milky-turbid viscous liquid. 5 g of diatomaceous earth powder with a median particle size of 46.5 µm was added with the object of suppressing clogging during filtration, and the mixture was stirred and mixed well with a spatula to form a slurry state.

In the same manner as in the Example 8, a glass fiber filter paper GC-90 with a diameter of 90 mm (retained particle diameter: 0.5 µm) was set in a stainless holder with tank, and a tank unit and a base plate were fastened and fixed. The slurry was introduced from an opening at an upper part of the tank, then the opening was closed using a tank cap, and filtration was performed by applying nitrogen pressure at 0.4 MPa. As a result, 139 g of dark brown almost translucent viscous liquid was obtained.

Example 9

Preparation of Liquid High-Purity Polyhydric Alcohol Derivative-Modified Silicone No. 9

180 g of the pale yellow liquid obtained in Production Example 9 (composition containing the polyhydric alcohol derivative-modified silicone No. 9 as the main component), and 5.4 g of alginic acid (whitish yellow fine powder) were prepared in a reactor, and the mixture was heated to 60 to 80° C. and stirred for 50 minutes. Thereafter, the mixture was cooled to lower than or equal to 50° C. under stirring, and when it was returned to room temperature after stopping stirring, it was separated into yellowish white precipitate and whitish yellow haze supernatant liquid. 5 g of diatomaceous earth powder with a median particle size of 30.6 μm was added with the object of suppressing clogging during filtration, and the mixture was stirred and mixed well with a spatula to form a slurry state.

In the same manner as in Example 8, a glass fiber filter paper GC-90 with a diameter of 90 mm (retained particle diameter: 0.5 μm) was set in a stainless holder with tank, and a tank unit and a base plate were fastened and fixed. The slurry was introduced from an opening at an upper part of the tank, then the opening was closed using a tank cap, and filtration was performed by applying nitrogen pressure at 0.4 MPa. As a result, a polyhydric alcohol derivative-modified silicone No. 9 expressed by the average composition formula: $^{R*25}MD_{187}M^{R*25}$ was obtained as colorless transparent uniform liquid. (Collected amount of 161 g) Here, $R^{*25}$ is as described below.

$R^{*25}$=—$C_3H_6O$—$CH_2(OH)$—$CH_2$—$N\{CH_2CH(CH_3)OH\}_2$

Example 9-2

Preparation of Liquid High-Purity Polyhydric Alcohol Derivative-Modified Silicone No. 9

180 g of the pale yellow liquid obtained in Production Example 9 (composition containing the polyhydric alcohol derivative-modified silicone No. 9 as the main component), and 1.1 g of catechin hydrate (brownish white fine powder) were prepared in a reactor, and the mixture was heated to 70 to 80° C. and stirred for 55 minutes. Thereafter, when the mixture was cooled to lower than or equal to 40° C. under stirring and the contents were checked, vermilion powder was dispersed in liquid that seemed transparent. 3 g of diatomaceous earth powder with a median particle size of 10.9 μm was added with the object of suppressing clogging during filtration, and the mixture was stirred and mixed well with a spatula to form a slurry state.

In the same manner as in Example 8, a glass fiber filter paper GC-90 with a diameter of 90 mm (retained particle diameter: 0.5 μm) was set in a stainless holder with tank, and a tank unit and a base plate were fastened and fixed. The slurry was introduced from an opening at an upper part of the tank, then the opening was closed using a tank cap, and filtration was performed by applying nitrogen pressure at 0.4 MPa. As a result, a polyhydric alcohol derivative-modified silicone No. 9 expressed by the average composition formula: $^{R*25}MD_{187}M^{R*25}$ was obtained as pale yellow transparent uniform liquid. (Collected amount of 166 g) Here, $R^{*25}$ is as described below.

$R^{*25}$=—$C_3H_6O$—$CH_2(OH)$—$CH_2$—$N\{CH_2CH(CH_3)OH\}_2$

The details of the "polyhydric alcohol derivative-modified silicones Nos. 1 to 4 and Nos. 7 to 9" which are the liquid high-purity polyhydric alcohol derivative-modified silicones according to the present invention, "composition containing the polyhydric alcohol derivative-modified silicones No. 5 or No. 6" which are the compositions containing the liquid high-purity polyhydric alcohol derivative-modified silicones according to the present invention, and "comparative compositions RE-1 to RE-9 containing the polyhydric alcohol derivative-modified silicones Nos. 1 to 9" according to the comparative examples prepared by the methods described above are shown in the following Table 2 (2A and 2B).

TABLE 2A

| No. | Test example number Treatment agent | Appearance (transparency) | Dilute oil agent | Chemical structure of main component[*1)] |
|---|---|---|---|---|
| 1 | Example 1 Trehalose Diatomaceous earth | Translucent | None | $MD_{37}D^{R*11}_{8.7}D^{R*21}_{3}D^{R*32}_{1}M$ |
|  | Example 1-2 Guanine Diatomaceous earth | Translucent |  |  |
| RE-1 | Comparative Example 1 Example 1-2 Trehalose aqueous solution Diatomaceous earth | Opaque (great turbidity) Opaque, strong turbidity | None |  |
| 2 | Example 2 Trehalose Diatomaceous earth | Translucent to fairly transparent | None | $MD_{37}D^{R*11}_{8.7}D^{R*22}_{3}D^{R*32}_{1}M$ |
|  | Example 2-2 Gallic acid Diatomaceous earth | Transparent |  |  |
| RE-2 | Comparative Example 2 | Opaque (great turbidity) | None |  |
| 3 | Example 3 Glycine Diatomaceous earth | Almost transparent | None | $MD_{43.4}D^{R*11}_{5.3}D^{R*21}_{2}D^{R*32}_{0.1}M$ |
|  | Example 3-2 $Na_2SO_4$ Diatomaceous earth | Almost transparent |  |  |
|  | Example 3-3 Diatomaceous earth | Fairly transparent |  |  |
| RE-3 | Comparative Example 3 | Opaque (great turbidity) | None |  |

TABLE 2A-continued

| No. | Test example number Treatment agent | Appearance (transparency) | Dilute oil agent | Chemical structure of main component*[1] |
|---|---|---|---|---|
| 4 | Example 4 PVA Diatomaceous earth | Almost transparent to translucent | None | $MD_{43.4}D^{R*11}{}_{5.3}D^{R*22}{}_{2}D^{R*32}{}_{0.1}M$ |
|   | Example 4-2 Malonic acid Diatomaceous earth | Almost transparent |  |  |
|   | Example 4-3 Trisodium citrate Diatomaceous earth | Almost transparent |  |  |
| RE-4 | Comparative Example 4 | Opaque (great turbidity) | None |  |
| 5 | Example 5 Diatomaceous earth | Fairly transparent to translucent | FZ-3196* | Crosslink $MD_{42.9}D^{R*31}{}_{0.3}D^{R*23}{}_{0.8}D^{R*11}{}_{4.4}D^{H}{}_{1.2}M$ with 1,5-hexadiene |
| RE-5 | Comparative Example 5 | White, opaque | FZ-3196* |  |

*FZ-3196: Caprylyl methicone (manufactured by Dow Corning Toray Co., Ltd.)
Note
*[1] The chemical structure of the polyhydric alcohol derivative-modified silicone serving as the main component is represented by an average composition formula.

TABLE 2B

| No. | Test example number Treatment agent | Appearance (transparency) | Dilute oil agent | Chemical structure of main component*[1] |
|---|---|---|---|---|
| 6 | Example 6 Carbomer Diatomaceous earth | Translucent | FZ-3196* | $MD_{330}D^{R*11}{}_{45}D^{R*32}{}_{30}D^{R*24}{}_{5}M$ |
| RE-6 | Comparative Example 6 | Milky white, opaque | FZ-3196* |  |
| 7 | Example 7 PVA Diatomaceous earth | Translucent | Toluene | $MD_{45}D^{R*31}{}_{1}D^{R*24}{}_{1}M$ |
| RE-7 | Comparative Example 7 | Milky white Opaque (great turbidity) | None |  |
| 8 | Example 8 Carbomer | Almost transparent | None | $MD_{44.7}D^{R*22}{}_{2}M$ |
|   | Example 8-2 Carbomer | Almost transparent |  |  |
|   | Example 8-3 Corn starch/ Carbomer | Somewhat translucent |  |  |
| RE-8 | Comparative Example 8 | Opaque (strong turbidity) | None |  |
| 9 | Example 9 Alginic acid Diatomaceous earth | Transparent | None | $R^{*25}MD_{187}M^{R*25}$ |
|   | Example 9-2 Catechin Diatomaceous earth | Transparent |  |  |
| RE-9 | Comparative Example 9 | Most of the portion is transparent, but a small white turbid haze portion is also mixed | None |  |

*FZ-3196: Caprylyl methicone (manufactured by Dow Corning Toray Co., Ltd.)
Note
*[1] The chemical structure of the polyhydric alcohol derivative-modified silicone serving as the main component is represented by an average composition formula.

In the table, the structures and types of the functional groups are as follows.
Siloxane Dendron Structure Group: $R^{*3}$

[Chemical Formula 64]

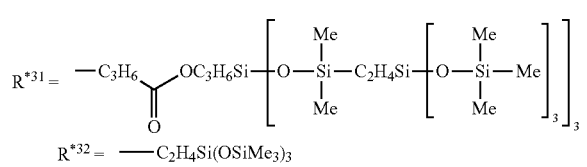

$$R^{*32} = {-}C_2H_4Si(OSiMe_3)_3$$

Polyhydric Alcohol Derivative Group: $R^{*2}$
$R^{*21} = {-}C_3H_6O{-}(C_3H_6O_2)_n{-}H$, n=1.7
$R^{*22} = {-}C_3H_6O{-}\{CH_2{-}CH(OH){-}CH_2O\}_2{-}H$
$R^{*23} = {-}C_3H_6O{-}(C_3H_6O_2)_n{-}H$, n=2.0
$R^{*24} = {-}C_3H_6O{-}(C_3H_6O_2)_n{-}H$, n=4.0
$R^{*25} = {-}C_3H_6O{-}CH_2(OH){-}CH_2{-}N\{CH_2CH(CH_3)OH\}_2$
Other Organic Groups: $R^{*1}$
$R^{*11} = {-}C_{16}H_{33}$ Light Transmittance Measurement
Light transmittance T % (wavelength 750 nm, and cell thickness 10 mm) at 20 to 25° C. was measured concerning samples of Example 1, Example 2-2, Example 3-3, Example 4, Example 4-3, Example 6, Example 8-2, and Comparative Example 1-2, Comparative Example 2, Comparative Example 3, Comparative Example 4, Comparative Example 6, and Comparative Example 8-2. The results are shown in Table 3.

TABLE 3

| Test example | Treatment agent | Appearance (color tone and transparency) | Light transmittance T % |
|---|---|---|---|
| Example 1 | Trehalose Diatomaceous earth | Light yellow translucent | 40 |
| Comparative Example 1-2 | Trehalose aqueous solution Diatomaceous earth | Opaque with strong white turbidity | 0.02 |
| Example 2-2 | Gallic acid Diatomaceous earth | Light yellow, transparent, uniform | 94.5 |
| Comparative Example 2 | None | Grayish brown, opaque (great turbidity) | 0.2 |
| Example 3-3 | Diatomaceous earth | Pale yellow, fairly transparent, uniform | 92.8 |
| Comparative Example 3 | None | Light brown, opaque (great turbidity) | 0.3 |
| Example 4 | PVA Diatomaceous earth | Pale yellow, almost transparent to Translucent, uniform | 88.6 |
| Example 4-3 | Trisodium citrate Diatomaceous earth | Light yellow, almost transparent, uniform | 85.3 |
| Comparative Example 4 | None | Grayish brown, opaque (great turbidity) | 0.3 |
| Example 6 | Carbomer Diatomaceous earth | Whitish yellow, translucent, uniform | 64.5 |
| Comparative Example 6 | None | Milky white, uniform (opaque) | 9.5 |
| Example 8-2 | Carbomer | Dark brown, almost transparent, uniform | 62.5 |
| Comparative Example 8-2 | None (filtration by filter paper) | Ash-brown, opaque (strong turbidity) | 0.02 |

It was found that, from the above, all of the samples of the comparative examples were opaque since a large amount of hydrophilic impurities not compatible with the polyhydric alcohol derivative-modified silicone that is the main component are contained, thereby appearing as turbidity; however, on the other hand, all of the examples to which the purification-increasing treatment of the present invention was performed showed a great improve in transparency of the appearance and uniformity. This fact indicated that a large part of hydrophilic impurities causing turbidity was effectively removed by the purification-increasing treatment of the present invention. In addition, the increase in purification according to the present invention was accomplished by treatment using solid particles, and depending on a technique of performing treatment in which solid particles are turned into solution, it is extremely difficult to increase the purity even after the solution was removed.

GPC Composition Distribution Measurement

Concerning the samples of Example 4-3 and Comparative Example 4, and the samples of Example 8-2 and Comparative Example 8-2, and also the samples of Example 9, Working Example 9-2, and Comparative Example 9, a hydroxyl group was capped with trimethylsilylation (TMS) by pretreatment, then toluene was set as an eluent and GPC measurement was performed. Thereby, an area ratio of a peak derived from the main component polyhydric alcohol derivative-modified silicone and a peak derived from residual hydrophilic impurities was obtained.

However, since the samples of Example 9, Example 9-2, and Comparative Example 9 are likely to contain an active amino group (adsorbed to the GPC column), after TMS capping of the hydroxyl group, ethoxycarbonylation capping of the amino group was further performed, and then, the samples were subjected to the GPC measurement.

Referencing position determination of the peak derived from the hydrophilic impurities at this time, the GPC measurement was similarly performed, by similarly capping the hydroxyl group from the high-purity chain diglycerinmonoallyl ether (number of repetitions of glycerin unit=2) that is the starting material. The conditions for pretreatment and GPC measurement are indicated below. The results are shown in Table 4.

Pretreatment

Approximately 0.5 g of the sample (approximately 0.1 g of high-purity chain diglycerinmonoallyl ether) was precisely weighed in a test tube and 1 mL of reagent-grade toluene was diluted.

N,O-bis(trimethylsilyl)acetamide equivalent to three times the molar number of the hydroxyl group included in the sample was added and mixed by gentle shaking. At this stage, the mixed liquid had white turbidity and was heterogeneous.

A cooling pipe was attached to the test tube and treatment was performed for one hour under a toluene environment. When the appearance of the reaction liquid was confirmed, the reaction liquid was changed to mostly transparent uniform liquid.

An appropriate volume of the reaction liquid in the test tube was precisely weighed in a vial bottle, and reagent-grade toluene was added and diluted. Thereby, a sample solution for GPC measurement with sample concentration of 1 wt. % was obtained upon calculation.

Diethylpyrocarbonate was added in an amount equivalent to 6 times the molar number of the amino group included in the sample with respect to the sample solution for GPC measurement corresponding to Example 9, Example 9-2 and Comparative Example 9, and the uniformly stirred solution was used as the sample solution for GPC measurement.

GPC Measurement Conditions

Eluent: toluene (reagent grade)

Measured temperature: 40° C.

Detector: refractometer (peak detection at the negative side)

Flow speed: 1.0 mL/min

Calibration: implemented with standard polystyrene

Injection amount of sample solution: 15 µL (sample concentration of 1 wt. %)

Peak Area Ratio of Main Component and Hydrophilic Impurities

Samples prior to and after the purification-increasing treatment according to the present invention (Untreated: Comparative Example 4; Comparative Example 8-2; Comparative Example 9, Post-treatment: Example 4-3; Example 8-2; Example 9; and Example 9-2) were subjected to GPC measurement as described above, and a ratio of the peak area derived from residual hydrophilic impurities with respect to the peak area derived from the polyhydric alcohol derivative-modified silicone serving as the main component was obtained by analysis of the obtained molecular weight distribution curvature, and the result thereof is summarized in Table 4 below.

TABLE 4

| Sample | Treatment agent | Number of peaks and shape of main component | Peak top molecular weight of main component | Peak area ratio (%) of hydrophilic impurities with respect to main component |
|---|---|---|---|---|
| Example 4-3 (Purification-increasing treatment) | Trisodium citrate Diatomaceous earth | One mountain-shaped peak | 12,300 | 0.41 |
| Comparative Example 4 (Untreated) | None | One mountain-shaped peak | 12,100 | 2.4 |
| Example 8-2 (Purification-increasing treatment) | Carbomer | One mountain-shaped peak | 10,100 | 1.4 |
| Comparative Example 8-2 (Untreated) | None (filtration by filter paper) | One mountain-shaped peak | 10,100 | 5.9 |
| Example 9 (Purification-increasing treatment) | Alginic acid Diatomaceous earth | One mountain-shaped peak | 22,700 | 0.27 |
| Example 9-2 (Purification-increasing treatment) | Catechin Diatomaceous earth | One mountain-shaped peak | 22,800 | 0.33 |
| Comparative Example 9 (Untreated) | None | One mountain-shaped peak | 23,000 | 1.10 |

As a result of the GPC analysis above, it was found that hydrophilic impurities were certainly contained in the sample of Comparative Example 4 (according to calculation from content, the impurities were equivalent to strength of 0.7 mass % of the main component). It was further found that hydrophilic impurities were effectively reduced in the sample of Example 4-3 obtained by applying the purification-increasing treatment of the present invention to the sample of Comparative Example 4. That is, when estimated from the peak area ratio in Table 4, it was found that the hydrophilic impurities were reduced to "⅙" of prior to treatment by the purification-increasing treatment of the present invention.

In addition, it was found that the sample of Comparative Example 8-2 obtained by filtering the composition obtained in Production Example 8 simply using filter paper certainly contain a large amount of hydrophilic impurities (according to calculation from content, the impurities were equivalent to 3.1 mass % of the main component). Meanwhile, it was found that the content of the hydrophilic impurities was significantly reduced in the sample of Example 8-2 obtained by applying the purification-increasing treatment of the present invention to the composition obtained in Production Example 8. That is, when estimated from the peak area ratio in Table 4, it was found that the hydrophilic impurities were reduced to less than or equal to "¼" of that before treatment (untreated product) by the purification-increasing treatment of the present invention. In this case, a reduction rate of impurities was a small numerical value in comparison to the case of Example 4, but from a viewpoint of being able to lower the impurities contained in an originally large quantity at once at 2 mass % or a nearby value is useful from the perspective of application to mass production on an industrial scale.

Moreover, it is believed that the sample of the Comparative Example 9 contains excess hydrophilic impurities at 1.0 mass % when calculating from content, but based on the comparison of the peak area in the GPC measurement, it was found that the content of hydrophilic impurities in the samples of Example 9 and Example 9-2 to which the purification-increasing treatment of the present invention had been performed was reduced to less than or equal to "⅓ to ¼" of that before the treatment (untreated product).

As above, the purification-increasing treatment of the present invention was found to have an excellent effect in a wide range for removal or reduction of hydrophilic impurities derived from a polyhydric alcohol derivative that are hydrophilic modifiers of each type of the polyhydric alcohol derivative-modified silicone, and be able to produce a high-purity polyhydric alcohol derivative-modified silicone in which the amount of impurities was cut by nearly 70% by treatment one time. Accordingly, when the purification-increasing treatment was repeated two times, it was considered to be possible to obtain an ultrahigh-purity polyhydric alcohol derivative-modified silicone not containing the impurities.

Stability Test 1

The samples of Example 1, Example 1-2, Example 2, Example 2-2, Example 3, Example 3-2, Example 3-3, Example 4, Example 4-2, Example 4-3, and Comparative Examples 1 to 4 placed in a 200 mL glass bottle were left to stand for one year at room temperature (changes from around 30° C. in the summer to around 15° C. in the winter), then appearance change of each sample was observed. The results are shown in Table 5.

TABLE 5

| No. | Test example | Initial appearance (transparency) | Room temperature, appearance change after one year |
|---|---|---|---|
| 1 | Example 1 | Light yellow translucent | No change |
|  | Example 1-2 | Pale yellow, translucent, uniform |  |
| RE-1 | Comparative Example 1 | Light brown, opaque (great turbidity) | Generation of white precipitate |
| 2 | Example 2 | Light yellow, translucent to fairly transparent and uniform | No change |
|  | Example 2-2 | Light yellow, transparent, uniform |  |
| RE-2 | Comparative Example 2 | Grayish brown, opaque (great turbidity) | No change |
| 3 | Example 3 | Light yellow, almost transparent, uniform | No change |
|  | Example 3-2 | Light yellow, almost transparent, uniform |  |
|  | Example 3-3 | Pale yellow, fairly transparent, uniform |  |
| RE-3 | Comparative Example 3 | Light brown, opaque (great turbidity) | Slight generation of white precipitate |
| 4 | Example 4 | Pale yellow, almost transparent to Translucent, uniform | No change |
|  | Example 4-2 | Light yellow, almost transparent, uniform |  |
|  | Example 4-3 | Light yellow, almost transparent, uniform |  |
| RE-4 | Comparative Example 4 | Light brown, opaque (great turbidity) | No change |

Stability Test 2

In order to confirm appearance stability (influence on transparency) with respect to more extreme temperature change, the samples of Example 3-3, Example 4, Example 2-2, Example 6, Example 8-2, Example 9, Example 9-2, and Comparative Example 9 were placed in a thermostatic chamber at 50° C. and allowed to stand overnight. Meanwhile, the samples of Example 2-2, Example 4-3, Example 6, Example 8-2, Example 9, Example 9-2, and Comparative Example 9 were placed in a refrigerator at 0° C. and allowed to stand overnight. The results are shown in Table 6.

TABLE 6

| Test example | Initial appearance | 50° C. | 0° C. |
|---|---|---|---|
| Example 3-3 | Pale yellow, fairly transparent, uniform | Maintained transparency and uniformity | No data |
| Example 4 | Pale yellow, almost transparent to translucent and uniform | Maintained transparency and uniformity | No data |
| Example 2-2 | Light yellow, transparent, uniform | Maintained transparency and uniformity | Opacified at 0° C., but returns to light yellowish-brown, transparent, and uniform when returned to room temperature |
| Example 4-3 | Light yellow, almost transparent, uniform | No data | Maintained transparency and uniformity |
| Example 6 | Whitish yellow, translucent, uniform | Maintained transparency and uniformity | Maintained transparency and uniformity |
| Example 8-2 | Dark brown, almost transparent, uniform | Maintained transparency and uniformity | Maintained transparency and uniformity |
| Example 9 | Colorless, transparent, uniform | Maintained transparency and uniformity | Maintained transparency and uniformity |
| Example 9-2 | Pale yellow, transparent, uniform | Maintained transparency and uniformity | Maintained transparency and uniformity |
| Comparative Example 9 | Light yellow, almost transparent, uniform | Maintained transparency and uniformity | White needle-like crystals are deposited. Crystals remained even after restoring to room temperature |

From the above results, it was confirmed that when compared with the samples of Comparative Examples, the samples of Examples had far higher purity from a viewpoint of less content of hydrophilic impurities, and they were also superior from the viewpoint of homogeneity and transparency of appearance, and this superiority was unchanged at high temperature, at low temperature, or under storage over a long period of time.

The purification-increasing treatment method of the present invention is easy, low energy consumption, and highly efficient, and solved, with a new viewpoint, the dilemma of the conventional method represented by an inefficient method such as a high temperature stripping method and an irrational process such as simply repeating filtration of the liquid impurities to remove them. Accordingly, contribution to an economic and social development is extremely great.

Hereinafter, formulation examples of the cosmetics and external use preparations according to the present invention are described, but the cosmetics and external use preparations according to the present invention are not limited to the types and compositions recited in these formulation examples.

The liquid high-purity polyhydric alcohol derivative-modified silicone according to the present invention can be used for various external use preparations and cosmetics. A specific formulation example thereof include one in which components corresponding to "silicone compound No. 1 to No. 16" in the formulation examples of various cosmetics and external use preparations disclosed in the examples and the like of Patent Document 14 (WO/2011/049248) are substituted with the above-described liquid high-purity polyhydric alcohol derivative-modified silicone No. 1 to No. 9 according to the present invention. A specific formulation example thereof also include one in which components corresponding to "silicone compound No. 1" in Formulation Examples 1 to 62 of various cosmetics and external preparations described in Patent Document 15 (Japanese Unexamined Patent Application Publication No. 2013-151660A) are substituted with the above-described liquid high-purity polyhydric alcohol derivative-modified silicone No. 1 to No. 9 according to the present invention.

The high-purity polyhydric alcohol derivative-modified silicone of the present invention has the advantage that, since a residual amount of hydrophilic modifier having a polarity extremely different from the modified silicone is reduced, problems related to poor compatibility at the time of blending various starting materials are unlikely to occur when designing a formulation for cosmetics or external use preparations, so that the scope of formulation design widens. At the same time, it is also possible to reduce the risk or concerns related to the stability of the final product. Since the composition has high purity, it is advantageous from the perspectives of the tactile feel improving effect, moisturizing effect, minimal degradation phenomena such as odorization over time, surface active effect, emulsification performance, powder dispersion stability, powder surface treatment effect, or the duration of these effects in comparison to typical polyhydric alcohol derivative-modified silicone compounds with great impurity content. In particular, in a formulation containing a powder or a formulation containing a small amount of water, the characteristics of the high-purity polyhydric alcohol derivative-modified silicone obtained by the present invention make it possible to finely disperse medicinal components or powders into cosmetics or external use preparations more stably than with conventional methods. As a result, a substantial advantage arises in that the original effects of the formulation are amplified, such as an improvement in evenness in application, in cosmetic duration or coloring or an improvement in a skin care or UV filter effect. In addition, in a formulation not containing a powder, the characteristics of the high-purity polyhydric alcohol derivative-modified silicone obtained by the present invention make it possible to easily obtain a product with excellent transparency and stability even if the composition has low viscosity.

The following can also be listed as formulation examples of the cosmetics and external use preparations according to the present invention. Furthermore, when all of the following polyether-modified silicone is substituted by the liquid high-purity polyhydric alcohol derivative-modified silicone according to the present invention (for example, No. 1), it is also possible to design PEG-FREE formulations. In the list below, "parts" indicates parts by (weight) mass.

Formulation Example: Liquid Foundation (W/O) Mainly Based on Hydrocarbon-Based Cosmetic Base Materials (Components)

| | | |
|---|---|---|
| 1. | Isododecane | 20 parts |
| 2. | Isohexadecane | 10 parts |
| 3. | Isotridecyl isononanoate | 3 parts |
| 4. | Glyceryl tricapryl-caprate | 2 parts |
| 5. | Polyether-modified silicone (note 1) | 0.5 parts |
| 6. | High-purity polyhydric alcohol derivative-modified silicone No. 5 | 1.5 parts |

-continued

|  |  |  |
|---|---|---|
| 7. | Organo-modified clay mineral (Benton 38V) | 1.5 parts |
| 8. | Octyl methoxycinnamate | 5 parts |
| 9. | Octyl silane-treated titanium oxide | 8.5 parts |
| 10. | Octyl silane-treated iron oxide red | 0.4 parts |
| 11. | Octyl silane-treated iron oxide yellow | 1 part |
| 12. | Octyl silane-treated iron oxide black | 0.1 parts |
| 13. | Dimethicone, dimethicone crosspolymer (note 2) | 2 parts |
| 14. | Isododecane/(acrylate/polytrimethylsiloxy methacrylate) copolymer (note 3) | 1 part |
| 15. | Trimethylsiloxysilicate | 1 part |
| 16. | 1,3-butylene glycol | 5 parts |
| 17. | Glycerin | 3 parts |
| 18. | Sodium chloride | 0.5 parts |
| 19. | Preservative | as appropriate |
| 20. | Purified water | remainder |
| 21. | Fragrance | as appropriate |

(note 1)
ES-5300, manufactured by Dow Corning Toray Co., Ltd.
(note 2)
DC9045, manufactured by Dow Corning Corp.
(note 3)
FA-4002ID, manufactured by Dow Corning Toray Co., Ltd.

Production Method

Step 1: Components 1, 2, 5, 6, 7, 8, 13, 14, and 15 are stirred to mix.

Step 2: Components 3, 4, and 9 to 12 are kneaded to mix with three rollers.

Step 3: The mixture of step 2 is added to the mixture obtained in step 1 while stirring, and they are further stirred to mix.

Step 4: The water phase in which components 16 to 21 were uniformly dissolved is added under stirring to the mixture obtained in step 3 and emulsified (by using an emulsifier), and a container is filled with the mixture to obtain a product.

The obtained W/O liquid foundation has no unpleasant odor, and when used, has excellent emulsification stability, water resistance, and cosmetic durability, and makes skin texture and wrinkles less noticeable. Despite being mainly composed of a hydrocarbon-based cosmetic base material, the mixture has a tactile sensation with excellent luxurious moisturizing feel, and is also excellent in adhesion.

Formulation Example: W/O Emulsion-Type Sunscreen Emulsion (Components) (Wt. %)

|  |  |  |
|---|---|---|
| 1. | D5 (decamethylcyclopentasiloxane) | 26.6 |
| 2. | Caprylyl methicone (Note 4) | 5.0 |
| 3. | BY 11-018 (Note 5) | 5.0 |
| 4. | Octyldodecyl myristate | 10.0 |
| 5. | Castor oil hydrogenated triisostearic acid PEG-20 | 0.3 |
| 6. | Polyether-modified silicone (Note 6) | 1.2 |
| 7. | High-purity polyhydric alcohol derivative-modified silicone No. 4 according to the present invention | 0.8 |
| 8. | Disteardimonium hectorite | 0.3 |
| 9. | Dimethicone/methicone polymer-treated zinc oxide | 15.0 |
| 10. | Aluminum stearate-treated titanium oxide | 13.0 |
| 11. | Methylparaben | 0.1 |
| 12. | 95% ethanol | 5.0 |
| 13. | Magnesium sulfate | 0.7 |
| 14. | Fragrance | as appropriate |
| 15. | Purified water | 17.0 |

(Note 4)
FZ-3196, manufactured by Dow Corning Toray Co., Ltd.
(Note 5)
D5 dilution containing 30% trimethylsiloxy silicic acid, manufactured by Dow Corning Toray Co., Ltd.
(Note 6)
ES-5300, manufactured by Dow Corning Toray Co., Ltd.

Production Method

A: Thoroughly blend components 1 to 11 to make a uniform dispersion.

B: Blend components 12 to 15 to make a uniform solution.

C: While stirring A, gradually add B and emulsify (by using an emulsifier).

Effects

The sunscreen emulsion is free of stickiness and friction, and spreads very lightly and well. A skin sensation of discomfort was slight while having extremely excellent adhesiveness, and a smooth silicone soft feeling was obtained. The emulsion has excellent stability, with minimal change in viscosity, such as increased viscosity, relative to either temperature or time. It also has an excellent sun-cutting effect and its durability.

Formulation Example: Bilayered (Shake Before Use to Mix Type) Sun Cut Lotion (Components) (Wt. %)

|  |  |  |
|---|---|---|
| 1. | D5 (decamethylcyclopentasiloxane) | 23.6 |
| 2. | Caprylyl methicone (Note 4) | 7.5 |
| 3. | DC 670 Fluid (Note 7) | 5.0 |
| 4. | Liquid paraffin | 3.0 |
| 5. | Ethylhexyl methoxycinnamate | 7.5 |
| 6. | Polyether-modified silicone (Note 6) | 1.0 |
| 7. | High-purity polyhydric alcohol derivative-modified silicone No. 3 according to the present invention | 1.0 |
| 8. | Organo-modified bentonite (Benton 38) | 0.2 |
| 9. | Methyl hydrogen polysiloxane-treated zinc oxide | 22.5 |
| 10. | 95% ethanol | 5.0 |
| 11. | 1,3-butylene glycol | 3.0 |
| 12. | Sodium citrate | 0.2 |
| 13. | Sodium chloride | 0.5 |
| 14. | Fragrance | as appropriate |
| 15. | Purified water | 20.0 |

(Note 4)
FZ-3196, manufactured by Dow Corning Toray Co., Ltd.
(Note 6)
ES-5300, manufactured by Dow Corning Toray Co., Ltd.
(Note 7)
D5 dilution containing 50% polypropyl silsesquioxane, manufactured by Dow Corning Corp.

Production Method

A: Thoroughly blend components 1 to 9 to make a uniform dispersion.

B: Blend components 10 to 15 to make a uniform solution.

C: While stirring A, gradually add B and emulsify (by using an emulsifier).

Effects

The sun cut lotion has the refreshing feel of water, and spreads very lightly and well. Additionally, because the zinc oxide microparticles can be stably microdispersed due to the excellent particle dispersing effect of the product of the present invention, there is the advantage of not being likely to leave a white residue on the skin after application. Furthermore, there is no discomfort, such as tense feeling, and ultraviolet protection effect is excellent.

Formulation Example: W/O Emulsion-Type Sun Cut Cream (Components) (Wt. %)

|  |  |  |
|---|---|---|
| 1. | EL-8040 ID (Note 8) | 5.0 |
| 2. | MQ-1640 Flake Resin (Note 9) | 1.0 |
| 3. | High-purity polyhydric alcohol derivative-modified silicone No. 2 according to the present invention | 1.0 |

-continued

| | | |
|---|---|---|
| 4. | Isotridecyl isononanate | 2.0 |
| 5. | Isohexadecane | 1.7 |
| 6. | Powder-in-oil dispersion (high-purity polyhydric alcohol derivative-modified silicone No. 4 according to the present invention/D5/fine particulate titanium oxide = 3/15/12 weight ratio mixture) | 22.5 |
| 7. | Powder-in-oil dispersion (high-purity polyhydric alcohol derivative-modified silicone No. 4 according to the present invention/D5/fine particulate zinc oxide = 1.5/10.5/18 weight ratio mixture) | 31.5 |
| 8. | 1,3-butylene glycol | 2.0 |
| 9. | Common salt | 0.5 |
| 10. | Purified water | 32.8 |

(Note 8)
Isododecane dilution containing 16% dimethicone crosspolymer, manufactured by Dow Corning Corp.
(Note 9)
Blend of trimethylsiloxysilicic acid and polypropyl silsesquioxane, manufactured by Dow Corning Corp.

Production Method

A: After blending components 2 to 5 to make a uniform solution, add component 1 and thoroughly blend to make a homogenous dispersion.

B: Blend components 8 to 10 to make a uniform solution.

C: After adding B to A and emulsifying while stirring A, add components 6 and 7 and blend to yield a uniform cream.

Effects

A unique, velvety, thick, and smooth application feel can be obtained. The sun cut cream has an excellent moisture-retaining effect, ultraviolet protection effect, and antiperspirant effect, with a natural use feel that is not sticky or greasy.

Formulation Example: Polyol/O Emulsified Vitamin C Compounded Skin Care Cream (Components) (Wt. %)

| | | |
|---|---|---|
| 1. | D5 (decamethylcyclopentasiloxane) | 17.9 |
| 2. | Dimethicone (5 cst) | 5.0 |
| 3. | High-purity polyhydric alcohol derivative-modified silicone No. 8 according to the present invention | 4.0 |
| 4. | 9040 silicone elastomer blend (Note 10) | 10.0 |
| 5. | Propylene glycol | 7.6 |
| 6. | Glycerin | 45.0 |
| 7. | Vitamin C | 10.5 |

(Note 10)
D5 dilution containing 12% dimethicone crosspolymer, manufactured by Dow Corning Corp.

Production Method

A: Thoroughly blend components 1 to 4 to make a uniform dispersion.

B: Blend components 5 to 7 to make a uniform solution by heating and stirring at 70° C.

C: While stirring A, gradually add B and emulsify (by using an emulsifier) to obtain a homogeneous cream.

Effects

Since a stable non-water-based emulsion is obtained, vitamin C was stably and favorably held. As a result, it was anticipated that the inherent effect of vitamin C which is a bioactive substance would be mild and sustained on the skin or in the skin.

Formulation Example: Polyol/O Emulsified Vitamin C Compounded External Use Preparation for Skin (Components) (Wt. %)

| | | |
|---|---|---|
| 1. | Caprylyl methicone (Note 4) | 3.0 |
| 2. | Mineral oil | 3.0 |
| 3. | Glyceryl tri(caprylate/caprate) | 3.0 |
| 4. | High-purity polyhydric alcohol derivative-modified silicone No. 5 according to the present invention | 1.0 |
| 5. | Polyether-modified silicone (Note 6) | 1.0 |
| 6. | EL-8050 ID Silicone Organic Elastomer Blend (Note 11) | 8.0 |
| 7. | Dipropylene glycol | 3.0 |
| 8. | Glycerin | 60.0 |
| 9. | Vitamin C | 15.0 |

(Note 4)
FZ-3196, manufactured by Dow Corning Toray Co., Ltd.
(Note 6)
ES-5300, manufactured by Dow Corning Toray Co., Ltd.
(Note 11)
Isododecane dilution containing 15% (dimethicone/bis-isobutyl PPG-20) crosspolymer, manufactured by Dow Corning Corp.

Production Method

A: Thoroughly blend components 1 to 6 to make a uniform dispersion.

B: Blend components 7 to 9 to make a uniform solution by heating and stirring at 70° C.

C: While stirring A, gradually add B and emulsify (by using an emulsifier) to obtain a homogeneous cream.

Effects

Since a stable non-water-based emulsion is obtained, vitamin C was stably and favorably held. As a result, it was anticipated that the inherent effect of vitamin C which is a bioactive substance would be mild and would sustained on the skin or in the skin.

The invention claimed is:

1. A production method of a liquid high-purity polyhydric alcohol derivative-modified silicone or a composition of the silicone, the method comprising:
   I) contacting i) an impurity-containing composition containing a liquid polyhydric alcohol derivative-modified silicone and hydrophilic impurities originating from a polyhydric alcohol derivative and ii) solid particles capable of capturing the hydrophilic impurities thereby capturing the hydrophilic impurities with the solid particles; and
   II) separating the polyhydric alcohol derivative-modified silicone and the solid particles;
   wherein the polyhydric alcohol derivative is a hydrophilic modifier of the polyhydric alcohol derivative-modified silicone;
   wherein the polyhydric alcohol derivative group is bonded to a silicon atom via a divalent linking group and is a glycerin derivative group comprising at least one unit having an average number of repetitions in a range of 1 to 10, the unit being selected from hydrophilic units of the structural formulae (4-1) to (4-3):

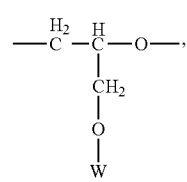

(4-1)

wherein W is a hydrogen atom or an alkyl group having from 1 to 20 carbons;

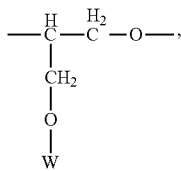

(4-2)

wherein W is as described above;

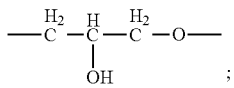

(4-3)

and wherein the polyhydric alcohol derivative group does not have an oxyalkylene structure having an average value of a number of repetitions of oxyalkylene unit of at least 2 as a hydrophilic group, has only a glycerin derivative group having an average value of a number of repetitions of glycerin unit in a range of 1 to 5, and does not have other hydrophilic groups.

2. The production method according to claim 1, wherein the polyhydric alcohol derivative-modified silicone is a polyhydric alcohol derivative-modified silicone other than a sugar derivative-modified silicone.

3. The production method according to claim 1, wherein the solid particles include at least one substance selected from a low molecular organic compound not containing a silicon atom, an uncrosslinked hydrophilic high molecular organic compound not containing a silicon atom, a crosslinked hydrophilic high molecular organic compound not containing a silicon atom, salts, materials derived from minerals, and activated carbon.

4. The production method according to claim 1, wherein the solid particles include a crosslinked hydrophilic high molecular organic compound not containing a silicon atom.

5. The production method according to claim 1, wherein the solid particles are porous.

6. The production method according to claim 1, wherein the solid particles include silicon dioxide.

7. The production method according to claim 1, wherein the solid particles include at least one hydrogen bond-forming substance and/or at least one ionic bond-forming substance and/or a hydrate of the hydrogen bond-forming substance and of the ionic bond-forming substance.

8. The production method according to claim 1, wherein the separating step includes a filtering step using a filtering material.

9. The production method according to claim 1, wherein the impurity-containing composition is brought into contact with the solid particles in the capturing step after diluting with a solvent, the solvent being a good solvent of the polyhydric alcohol derivative-modified silicone and a poor solvent of the hydrophilic impurities.

10. The production method according to claim 9, further comprising a step of removing the solvent by at least one of heating and decompressing the composition after the separating step.

11. The production method according to claim 1, wherein the polyhydric alcohol derivative-modified silicone is a polyhydric alcohol derivative-modified silicone of the general formula (1):

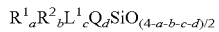

(1)

wherein $R^1$ is a monovalent organic group (however, excluding $R^2$, L, and Q), a hydrogen atom or a hydroxyl group; $R^2$ is a substituted or unsubstituted, straight or branched monovalent hydrocarbon group having from 9 to 60 carbons, or a chain organosiloxane group of the general formula (2-1):

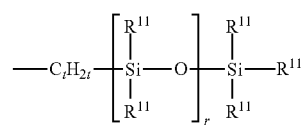

(2-1)

wherein $R^{11}$ are each independently a substituted or unsubstituted monovalent hydrocarbon group having from 1 to 30 carbons, a hydroxyl group, or a hydrogen atom, and at least one of $R^{11}$ is the monovalent hydrocarbon group; t is a number in a range of 2 to 10; and r is a number in a range of 1 to 500, or the general formula (2-2):

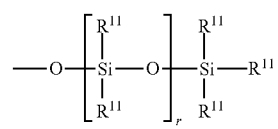

(2-2)

wherein $R^{11}$ and r are as described above; $L^1$ is a silylalkyl group having a siloxane dendron structure of the general formula (3) when i=1:

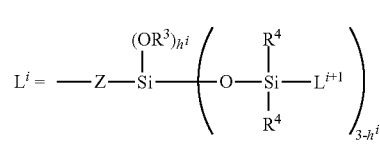

(3)

wherein $R^3$ are each independently a substituted or unsubstituted, straight or branched monovalent hydrocarbon group having from 1 to 30 carbons; $R^4$ are each independently an alkyl group or phenyl group having from 1 to 6 carbons; Z is a divalent organic group; i is a generation of a silylalkyl group ($L^i$) and is an integer of 1 to k when k is a number of generations that is a number of repetitions of the silylalkyl group; a number of generations k is an integer from 1 to 10; $L^{i+1}$ is the silylalkyl group when i is less than k, and $R^4$ when i=k; and $h^i$ is a number in a range of 0 to 3; Q is a polyhydric alcohol derivative group; and a, b, c, and d are numbers in ranges of $1.0 \le a \le 2.5$, $0 \le b \le 1.5$, $0 \le c \le 1.5$, and $0.0001 \le d \le 1.5$, respectively.

12. The production method according to claim 11, wherein the polyhydric alcohol derivative group is a glycerin derivative group.

13. The production method according to claim 11, wherein the polyhydric alcohol derivative group is a diglycerin derivative group of the general formula (5-1):

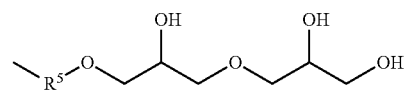

(5-1)

wherein $R^5$ is a divalent organic group not having an oxyalkylene structure with an average value of a number of repetitions of oxyalkylene unit of at least 2, or the general formula (5-2):

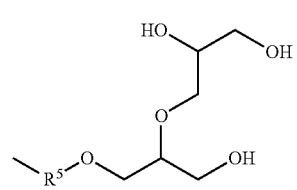 (5-2)
wherein R⁵ is as described above.
14. The production method according to claim 1, wherein the polyhydric alcohol derivative-modified silicone is a polyhydric alcohol derivative-modified crosslinked silicone.
* * * * *